US011219670B2

(12) United States Patent
Kim et al.

(10) Patent No.: US 11,219,670 B2
(45) Date of Patent: Jan. 11, 2022

(54) TARGETING CAPN9/CAPNS2 ACTIVITY AS A THERAPEUTIC STRATEGY FOR THE TREATMENT OF MYOFIBROBLAST DIFFERENTIATION AND ASSOCIATED PATHOLOGIES

(71) Applicant: The Johns Hopkins University, Baltimore, MD (US)

(72) Inventors: David Kim, San Jose, CA (US); Harry C. Dietz, Towson, MD (US)

(73) Assignee: The Johns Hopkins University, Baltimore, MD (US)

( * ) Notice: Subject to any disclaimer, the term of this patent is extended or adjusted under 35 U.S.C. 154(b) by 395 days.

(21) Appl. No.: 15/508,675

(22) PCT Filed: Sep. 5, 2015

(86) PCT No.: PCT/US2015/048739
§ 371 (c)(1),
(2) Date: Mar. 3, 2017

(87) PCT Pub. No.: WO2016/037157
PCT Pub. Date: Mar. 10, 2016

(65) Prior Publication Data
US 2018/0318405 A1    Nov. 8, 2018

Related U.S. Application Data

(60) Provisional application No. 62/167,426, filed on May 28, 2015, provisional application No. 62/046,383, filed on Sep. 5, 2014.

(51) Int. Cl.
| | |
|---|---|
| *A61K 38/55* | (2006.01) |
| *A61K 38/17* | (2006.01) |
| *A61K 31/33* | (2006.01) |
| *A61K 38/05* | (2006.01) |
| *A61K 31/713* | (2006.01) |
| *A61K 48/00* | (2006.01) |
| *A61P 35/00* | (2006.01) |
| *C07K 14/495* | (2006.01) |
| *G01N 33/50* | (2006.01) |

(52) U.S. Cl.
CPC .............. *A61K 38/55* (2013.01); *A61K 31/33* (2013.01); *A61K 31/713* (2013.01); *A61K 38/05* (2013.01); *A61K 38/1767* (2013.01); *A61K 48/005* (2013.01); *A61P 35/00* (2018.01); *C07K 14/495* (2013.01); *G01N 33/5008* (2013.01); *G01N 2333/96466* (2013.01); *G01N 2500/10* (2013.01); *G01N 2800/7028* (2013.01); *G01N 2800/7052* (2013.01)

(58) Field of Classification Search
CPC ........ A61K 38/55; A61K 38/17; A61K 31/33; A61K 31/00
See application file for complete search history.

(56) References Cited

U.S. PATENT DOCUMENTS

| | | |
|---|---|---|
| 4,708,871 A | 11/1987 | Geysen |
| 4,833,092 A | 5/1989 | Geysen |
| 5,223,409 A | 6/1993 | Ladner et al. |
| 5,331,573 A | 7/1994 | Balaji et al. |
| 5,403,484 A | 4/1995 | Ladner et al. |
| 5,500,807 A | 3/1996 | Lavin et al. |
| 5,556,762 A | 9/1996 | Pinilla et al. |
| 5,571,689 A | 11/1996 | Heuckeroth et al. |
| 5,644,048 A | 7/1997 | Yau |
| 5,663,143 A | 9/1997 | Ley et al. |
| 5,750,373 A | 5/1998 | Garrard et al. |
| 6,506,559 B1 | 1/2003 | Fire et al. |
| 6,573,099 B2 | 6/2003 | Graham |
| 6,656,687 B1 | 12/2003 | Hyldig-Nielsen |
| 2003/0153519 A1 | 8/2003 | Kay et al. |
| 2003/0167490 A1 | 9/2003 | Hunter et al. |
| 2005/0222043 A1* | 10/2005 | Stangl .................... A61K 31/00 424/130.1 |
| 2011/0117106 A1* | 5/2011 | Prince ..................... A61P 11/08 424/158.1 |
| 2011/0245150 A1 | 10/2011 | Heuer et al. |

FOREIGN PATENT DOCUMENTS

| | | |
|---|---|---|
| JP | 2008127322 A | 6/2008 |
| WO | 84/03506 A1 | 9/1984 |
| WO | 84/03564 A1 | 9/1984 |
| WO | 00/00823 A1 | 1/2000 |
| WO | 00/39585 A1 | 7/2000 |

OTHER PUBLICATIONS

Chen, C-J., et al. Role of calpain-9 and PKC-delta in the apoptotic mechanism of lumen formation in CEACAM1 transfected breast epithelial cells. Exp. Cell Res., 2010, 316(4):638-648.*
Donkor, I.O. Calpain inhibitors: A survey of compounds reported in the patent and scientific litature. Exp. Opin. Ther. Patents, 2011, 21(5):601-636.*
Donkor, I.O. An updated patent review of calpain inhibitors (2012-2014). Exp. Opin. Ther. Patents, 2015, 25(1):17-31.*
Tabata, C., et al. The calpain inhbitor calpeptin prevents bleomycin-induced pulmonary fibrosis in mice. Clin. Exp. Immunol., 2010, 162:560-567.*
Kim, D.H., et al. Calpain 9 as a therapeutic target in TGFb-induced mesenchymal transition and fibrosis. Sci. Transl. Med., 2019, 11:eaau2814, p. 1-15.*
Ono, Y., et al. Calpain research for drug discovery: challenges and potential. Nat. Rev. Drug Discov., 2016, 15(12):854-876.*
Ravulapalli, R., et al. Distinguishing between calpain heterodimerization and homodimerization. FEBS J., 2009, 276, 973-982.*

(Continued)

*Primary Examiner* — Xiaozhen Xie
(74) *Attorney, Agent, or Firm* — Mintz Levin Cohn Ferris Glovsky and Popeo, P.C.; Peter F. Corless

(57) ABSTRACT

Provided herein are, inter alia, compositions and methods for identifying and using agents capable of inhibiting myofibroblast transition as well as methods for treating diseases associated with the same in a subject in need thereof.

8 Claims, 36 Drawing Sheets

(56) References Cited

OTHER PUBLICATIONS

C. Tabata et al., "The calpain inhibitor calpeptin prevents bleomycin-induced pulmonary fibrosis in mice: Calpeptin prevents lung fibrosis", Clinical and Experimental Immunology, vol. 162, No. 3, Dec. 1, 2010 (Dec. 1, 2010), pp. 560-567.
Arumugam Ramachandran Muralidharan et al., "Virtual screening based on pharmacophoric features of known calpain inhibitors to identify potent inhibitors of calpain", Medicinal Chemistry Research., vol. 23, No. 5, Oct. 22, 2013 (Oct. 22, 2013), pp. 2445-2455.
International Search Report issued in corresponding International Application No. PCT/US2015/048739, dated Feb. 12, 2016, 5 pages.
Written Opinion of the International Searching Authority issued in corresponding International Application No. PCT/US2015/048739, dated Feb. 12, 2016, 5 pages.
EP Communication dated May 29, 2020 cited in counterpart EP application No. 15 837 830.7-1112.
Response filed with EPO dated Feb. 3, 2020 in corresponding EP application No. 15 837 830.7-1112.
EP Communication dated Jul. 22, 2019 cited in counterpart EP application No. 15 837 830.7-1112.
Response filed with EPO dated Nov. 5, 2018 in counterpart EP application No. 15 837 830.7-1112.
EP Communication dated Apr. 25, 2018 cited in counterpart EP application No. 15 837 830.7-1112.
Beaucage (1993) "Oligodeoxyribonucleotides Synthesis", Methods in Molecular Biology, 20:33-61.
Boyer et al. (2000) "Induction and Regulation of Epithelial-Mesenchymal transitions", Biochemical Pharmacology, 60:1091-1099.
Branton et al. (1999) "TGF-beta and fibrosis", Microbes and Infection, 1:1349-1365.
Brooks et al. (1983) "CHARMM: A Program for Macromolecular Energy, Minimization, and Dynamics Calculations", Journal of Computational Chemistry, 4(2):187-217.
Burkert (1982) "Pitfalls in the Use of the Torsion Angle Driving Method for the Calculation of Conformational Interconversions", Journal of Computational Chemistry, 3(1):40-46.
Capaldi et al. (2000) "Signal amplification through nucleotide extension and excision on a dendritic DNA platform", Nucleic Acid Research, 28(7):8 pages.
Carragher (Jan. 2006) "Calpain Inhibition: a Therapeutic Strategy Targeting Multiple Disease States", Current Pharmaceutical Design, 12(5):615-638.
Chen et al. (Feb. 15, 2010) "Role of Calpain-9 and PKC-Delta in the Apoptotic Mechanism of Lumen Formation in CEACAM1 Transfected Breast Epithelial Cells", Experimental Cell Research, 316(4):638-648.
Chubanov et al. (2012) "Natural and synthetic modulators of SK (Kca2) potassium channels inhibit magnesium-dependent activity of the kinase-coupled cation channel TRPM7", British Journal of Pharmacology, 166:1357-1376.
Clackson et al. (Aug. 15, 1991) "Making Antibody Fragments Using Phage Display Libraries", Nature, 352(6336):624-628.
Coburn et al. (Sep. 2002) "Potent and Specific Inhibition of Human Immunodeficiency Virus Type 1 Replication by RNA Interference", Journal of Virology, 76(18):9225-9231.
Cohen et al. (Mar. 1990) "Molecular Modeling Software and Met hods for Medicinal Chemistry", Journal of Medicinal Chemistry, 33(3):883-894.
Connolly (Aug. 19, 1983) "Solvent-Accessible Surfaces of Proteins and Nucleic Acids", Science, 221(4612):709-713.
Cwirla et al. (Aug. 1990) "Peptides on Phage: A Vast Library of Peptides for Identifying Ligands", Proceedings of the National Academy of Sciences, 87(16):6378-6382.
Davis et al. (2007) "The Crystal Structures of Human Calpains 1 and 9 Imply Diverse Mechanisms of Action and Auto-inhibition", Journal of Molecular Biology, 366:216-229.
De Maria et al. (May 15, 2009) "Calpain Expression and Activity during Lens Fiber Cell Differentiation", Journal for Biological Chemistry, 284(20):13542-13550.
Dunbrack et al. (Apr. 1, 1997) "Meeting review: the Second Meeting on the Critical Assessment of Techniques for Protein Structure Prediction (CASP2), Asilomar, California, Dec. 13-16, 1996", Folding & Design, 1:R27-R42.
Egholm et al. (Oct. 7, 1993) "PNA Hybridizes to Complementary Oligonucleotides Obeying the Watson-Crick Hydrogen-Bonding Rules", Nature, 365:566-568.
Friedman et al. (Jan. 9, 2013) "Therapy for Fibrotic Diseases: Nearing the Starting Line", Science Translational Medicine, 5(167):17 pages.
Geysen et al. (Jan. 1985) "Small peptides induce antibodies with a sequence and structural requirement for binding antigen comparable to antibodies raised against the native protein", PNAS, 82:178-182.
Geysen et al. (1987) "Strategies for epitope analysis using peptide synthesis", Journal of Immunological Methods, 102:259-274.
Geysen et al. (Jul. 1984) "Use of peptide synthesis to probe viral antigens for epitopes to a resolution of a single amino acid", PNAS, 81:3998-4002.
Gooch et al. (Apr. 9, 2004) "Involvement of Calcineurin in Transforming Growth Factor-beta-mediated Regulation of Extracellular Matrix Accumulation", The Journal of Biological Chemistry, 279(15):15561-15570.
Goodford et al. (1985) "A Computational Procedure for Determining Energetically Favorable Binding Sites on Biologically Important Macromolecules", Journal of Medicinal Chemistry, 28(7):849-857.
Goodsell et al. (1990) "Automated Docking of Substrates to Proteins by Simulated Annealing", Proteins Structure, Function, and Genetics, 8:195-202.
Hata et al. (Jul. 2010) "Calpain 8/nCL-2 and Calpain 9/nCL-4 Constitute an Active Protease Complex, G-Calpain, Involved in Gastric Mucosal Defense", Plos Genetics, e1001040, 6(7):14 pages.
Hyrup et al. (1996) "Peptide Nucleic Acids (PNA): Synthesis, Properties and Potential Applications", Bioorganic & Medicinal Chemistry, 4(1):5-23.
Iwano et al. (Aug. 2002) "Evidence that fibroblasts derive from epithelium during tissue fibrosis", The Journal of Clinical Investigation, 110(3):341-350.
Janda et al. (Jan. 21, 2002) "Ras and TGF-beta cooperatively regulate epithelial cell plasticity and metastasis: dissection of Ras signaling pathways", The Journal of Cell Biology, 156(2):299-313.
Jones et al. (1991) "Improved Methods for Building Protein Models in Electron Density Maps and the Location of Errors in these Models", Acta Crystallographica, A47:110-119.
Kalluri et al. (2003) "Epithelial-Msenchymal Transition and its Implications for Fibrosis", Journal of Clinical Investigation, 112(12):1776-1784.
Kang et al. (Dec. 1991) "Antibody Redesign by Chain Shuffling from Random Combinatorial Immunoglobulin Libraries", PNAS, 88:11120-11123.
Kiemer et al. (2001) "Identifcation of Genes Involved in Epithelial-mesenchymal Transition and Tumor Progression", Oncogene, 20:6679-6688.
Kraulis (1991) "MOLSCRIPT: A Program to Produce Both Detailed and Schematic Plots of Protein Structures", Journal of Applied Crystallography, 24:946-950.
Kuntz et al. (1982) "A Geometric Approach to Macromolecule-Ligand Interactions", Journal of Molecular Biology, 161:269-288.
Kuntz (Aug. 21, 1992) "Structure-Based Strategies for Drug Design and Discovery", Science, 257:1078-1082.
Lamouille et al. (Mar. 2014) "Molecular mechanisms of epithelial-mesenchymal transition", Nature Reviews, 15:178-196.
Leask et al. (Jun. 2017) "TGF-beta signaling and the fibrotic response", The FASEB Journal, 18(7):816-827.
Leblue et al. (Jun. 30, 2013) "Origin and function of myofibroblasts in kidney fibrosis", Nature Medicine, 19(8):1047-1053.
Lee et al. (Feb. 28, 2014) "Bleomycin delivery by osmotic minipump: similarity to human scleroderma interstitial lung disease", American Journal of Physiology—Lung Cellular and Molecular Physiology, 306:L736-L748.

(56) References Cited

OTHER PUBLICATIONS

Lee et al. (1998) "Molecular Cloning and Characterization of a Novel Tissue-Specific Calpain Predominantly Expressed in the Digestive Tract", Journal of Biological Chemistry, 379:175-183.
Letavernier et al. (Jan. 2012) "The Role of Calpains in Myocardial Remodelling and Heart Failure", Cardiovascular Research, 96(1):38-45.
Li et al. (2006) "Suppression of atherogenesis by delivery of TGF-beta1 ACT using adeno-associated virus type 2 in LDLR knockout mice", Biochemical and Biophysical Research Communications, 344:701-707.
Li et al. (Nov. 2011) "Targeted Inhibition of Calpain Reduces Myocardial Hypertrophy and Fibrosis in Mouse Models of Type 1 Diabetes", Diabetes, 60(11):2985-2994.
Lowman et al. (Nov. 12, 1991) "Selecting High-Affinity Binding Proteins by Monovalent Phage Display", Biochemistry, 30(45):10832-10838.
Ma et al. (2004) "Expression of calpain small subunit 2 in mammalian tissues", Current Eye Research, 29(4-5):337-347.
Mag et al. (1991) "Synthesis and selective cleavage of an oligodeoxynucleotide containing a bridged internucleotide 5'-phosphorothioate linkage", Nucleic Acids Research, 19(7):1437-1441.
Mani et al. (May 16, 2008) "The Epithelial-Mesenchymal Transition Generates Cells with Properties of Stem Cells", Cell, 133:704-715.
Marks et al. (Dec. 5, 1991) "By-Passing Immunization: Human Antibodies from V-Gene Libraries Displayed on Phage", Journal of Molecular Biology, 222(3):581-597.
McKay et al. (Jan. 15, 1999) "Characterization of a Potent and Specific Class of Antisense Oligonucleotide Inhibitor of Human Protein Kinase C-a Expression", The Journal of Biological Chemistry, 274(3):1715-1722.
Miranker et al. (1991) "Functionality Maps of Binding Sites: A Multiple Copy Simultaneous Search Method", Proteins: Structure, Function, and Genetics, 11:29-34.
Miyazono (2009) "Transforming Growth Factor-b signaling in Epithelial-mesenchymal Transition and Progression of Cancer", Proceedings of the Japan Academy, Ser. B, Physical and Biological Sciences, 85(8):314-323.
Navia et al. (1992) "Use of Structural Information in Drug Design", Current Opinion in Structural Biology, 2:202-210.
Nielsen (1993) "Peptide Nucleic Acid (PNA): A Model Structure for the Primordial Genetic Material?", Origins of Life and Evolution of the Biosphere, 23(5-6):323-327.
Nieto (Mar. 2002) "The Snail Superfamily of Zinc-finger Transcription Factors", Nature Reviews Molecular Cell Biology, 3:155-166.
Nishibata et al. (1991) "Automatic Creatibn of Drug Candidate Structures Based on Receptor Structure—Starting Point for Artificial Lead Generation", Tetrahedron, 47(43):8985-8990.
Padua et al. (Dec. 2, 2008) "Roles of TGFβ in metastasis", Cell Research, 19:89-102.
Peng et al. (Apr. 2, 2013) "Bleomycin Induces Molecular Changes Directly Relevant to Idiopathic Pulmonary Fibrosis: A Model for "Active" Disease", Plos One, 8(4):15 pages.
Piccirillo et al. (1998) "TGF-b1 Somatic Gene Therapy Prevents Autoimmune Disease in Nonobese Diabetic Mice", Journal of Immunology, 161:3950-3956.
Prud'Homme et al. (Sep. 3, 1999) "The Inhibitory Effects of Transforming Growth Factor-Beta-1 (TGF-beta1) in Autoimmune Diseases", Journal of Autoimmunity, 14:23-42.
Savary et al. (2011) "Role of TGF-beta Signaling in EMT, Cancer Progression and Metastasis", Drug Discovery Today:Disease Models, 8(2-3):121-126.
Schad et al. (2002) "A Novel Human Small Subunit of Calpains", Biochemical Journal, 362:383-388.
Schoofs et al. (Jan. 15, 1988) "Epitopes of an Influenza Viral Peptide Recognized by Antibody at Single Amino Acid Resolution", Journal of Immunology, 140(2):611-616.
Singh et al. (2010) "EMT, Cancer Stem Cells and Drug Resistance: An Emerging Axis of Evil in the War on Cancer", Oncogene, 29:4741-4751.
Smith (1991) "Surface Presentation of Protein Epitopes Using Bacteriophage Expression Systems", Current Opinion in Biotechnology, 2:668-673.
Stewart et al. (2003) "Lentivirus-delivered Stable Gene Silencing by RNAi in Primary Cells", RNA, 9:493-501.
Strutz et al. (Jul. 1995) "Identification and Characterization of a Fibroblast Marker: FSP1", The Journal of Cell Biology, 130(2):393-405.
Summerton (1999) "Morpholino Antisense Oligomers: The Case for an RNase H-independent Structural Type", Biochimica et Biophysica Acta, 1489:141-158.
Suzuki et al. (Feb. 2004) "Structure, Activation, and Biology of Calpain", Diabetes, 53(1):S12-S18.
Verlinde et al. (Jul. 15, 1994) "Structure-based drug design: progress, results and challenges", Structure, 2:577-587.
Wahlestedt et al. (May 9, 2000) "Potent and Nontoxic Antisense Oligonucleotides Containing Locked Nucleic Acids", PNAS, 97(10):5633-5638.
Weiner et al. (1984) "A New Force Field for Molecular Mechanical Simulation of Nucleic Acids and Proteins", Journal of the American Chemical Society, 106:765-784.
Wu et al. (Jan. 7, 2007) "Detection of Epithelial to Mesenchymal Transition in Airways of a Bleomycin Induced Pulmonary Fibrosis Model Derived from an α-smooth Muscle Actin-Cre Transgenic Mouse", Respiratory Research, 8:11 pages.
Wynn (2008) "Cellular and Molecular Mechanisms of Fibrosis", Journal of Pathology, 214:199-210.
Xue et al. (Jun. 15, 2003) "The Gatekeeper Effect of Epithelial-Mesenchymal Transition Regulates the Frequency of Breast Cancer Metastasis", Cancer Research, 63:3386-3394.
Yang et al. (2001) "Dissection of Key Events in Tubular Epithelial to Myofibroblast Transition and Its Implications in Renal Interstitial Fibrosis", American Journal of Pathology, 159(4):1465-1475.
Yoshikawa et al. (May 2000) "Isolation of Two Novel Genes, Down-regulated in Gastric Cancer", Japanese Journal of Cancer Research, 91:459-463.
Zeisberg et al. (Oct. 2001) "Collagen Composition and Assembly Regulates Epithelial-Mesenchymal Transdifferentiation", American Journal of Pathology, 159(4):1313-1321.
Zeisberg et al. (Jun. 6, 2002) "Renal Fibrosis: Extracellular Matrix Microenvironment Regulates Migratory Behavior of Activated Tubular Epithelial Cells", American Journal of Pathology, 160(6):2001-2008.
Zimmerman et al. (2000) "The Calpain Small Subunit Gene is Essential: Its Inactivation Results in Embryonic Lethality", IUBMB Life, 50(1):63-68.

* cited by examiner

TARGETING CAPN9/CAPNS2 ACTIVITY AS A THERAPEUTIC STRATEGY FOR THE TREATMENT OF MYOFIBROBLAST DIFFERENTIATION AND ASSOCIATED PATHOLOGIES

CROSS-REFERENCE TO RELATED APPLICATIONS

This application is the U.S. national phase, pursuant to 35 U.S.C. § 371, of international application Ser. No. PCT/US2015/048739, filed Sep. 5, 201, designating the United States and published in English on Mar. 10, 2016 as publication No. WO 2016/037157 A2, which claims priority to U.S. Provisional Patent Application No. 62/046,383, filed Sep. 5, 2014 and to U.S. Provisional Patent Application No. 62/167,426, filed May 28, 2015, the disclosures of each of which are incorporated by reference herein in their entireties.

FIELD OF INVENTION

This invention relates generally to the field of identification and use of CAPN9 and/or CAPNS2 inhibitors for the treatment of diseases associated with myofibroblast differentiation.

BACKGROUND

Fibrotic diseases account for an estimated 45% of deaths in the developed world but the development of therapies for such diseases is still in its infancy. Current treatments for fibrotic diseases, such as idiopathic lung fibrosis, renal fibrosis, systemic sclerosis, and liver cirrhosis, are few in number, can only alleviate symptoms, and fail to treat the underlying cause. Despite the current limited understanding of the diverse etiologies responsible for these conditions, similarities in the phenotype of the affected organs, across fibrotic diseases, strongly support the existence of common pathogenic pathways. At present, it is recognized that a primary driver of fibrotic disease is high transforming growth factor-beta (TGFβ) signaling, which can promote the transformation of normally functioning cells into fibrosis-promoting cells. Termed "myofibroblasts," these transformed cells can secrete large amounts of extracellular matrix proteins and matrix degrading enzymes, resulting in the formation of scar tissue and eventual organ failure. This transformative process, termed "myofibroblast differentiation" (which includes Epithelial-to-Mesenchymal Transition (EpMT) and its variations like Endothelial-to-Mesenchymal Transition (EnMT) and Fibroblast-to-Myofibroblast Transition (FMT)), is a major target for the treatment of fibrotic diseases. Myofibroblast differentiation has also been shown to occur within cancer cells that have been chronically exposed to high TGFβ, causing stationary epithelial cells to become motile, invasive, and metastasize. This transformative process, within the context of cancer, has been documented to associate with the acquisition of drug resistance, immune system evasion, and development of stem cell properties.

Despite the tremendous potential of myofibroblast differentiation-inhibiting drugs and the numerous attempts to develop a working treatment, the data gathered thus far has yet to translate into practical therapy partly due to lack of an ideal target protein. Initial strategies to target myofibroblast differentiation focused on proximal inhibition of the TGFβ signaling pathway by various methods, including targeting ligand activators (e.g., alpha-v integrins), ligand-receptor interactions (e.g., using neutralizing antibodies), or TGFβ receptor kinase activity (e.g., small molecule chemical compound drugs to block signal transduction). Unfortunately, TGFβ is a pleiotropic cytokine with many physiological functions such that global suppression of TGFβ signaling was also associated with severe side effects. Additionally, current data suggests that such proximal inhibition may be vulnerable to pathologic workaround strategies (i.e., due to redundancy or compensation), that would limit the utility of such drugs. Further complicating matters is that in cancer, TGFβ signaling early on functions as an anti-tumorigenic growth inhibitor but later becomes tumor promoting and is another reason why selective inhibition of pathogenic elements of signaling is so strongly desired. In light of these inherent limitations, current treatment strategies have refocused on identification and inhibition of critical distal events in TGFβ signaling, which in theory would preferentially target the pathologic, but not physiological functions of TGFβ signaling.

SUMMARY

The presently disclosed subject matter advances existing calpain research that has linked increased expression and/or activity of calpain proteases to the development of tissue fibrosis in various models, for example, by elucidating previously undefined underlying mechanisms of such diseases. Whereas the strong majority of previous calpain research focused on the ubiquitously expressed CAPN1, CAPN2, and CAPNS1 isoforms as the main drivers of disease rather than tissue-specific isoforms with more limited expression, the presently disclosed subject matter identifies specific isoforms with more limited expression that are more suitable targets for fibrotic diseases. Further, in contrast to various prior in vivo experiments and potential therapies that have utilized non-isoform specific pan-calpain inhibitors, in some embodiments the work described herein demonstrates the use of isoform-specific calpain inhibitors that are useful for the treatment of diseases associated with myofibroblast differentiation (such as TGFβ-mediated diseases associated with myofibroblast transition and associated pathologies).

The presently disclosed subject matter provides the targeting of CAPN9/CAPNS2 activity as a strategy towards the treatment of diseases associated with myofibroblast differentiation and addresses a major need for severely afflicted patients with currently limited options. Accordingly, methods of inhibiting myofibroblast differentiation (e.g., Epithelial/Endothelial-to-Mesenchymal Transition (EpMT/EnMT)) are provided. In certain aspects, methods of inhibiting myofibroblast differentiation (e.g., Epithelial/Endothelial-to-Mesenchymal Transition (EpMT/EnMT)) comprise contacting a cell with at least one agent that decreases the expression level and/or activity of a calpain. In other aspects, methods of inhibiting myofibroblast differentiation (e.g., EpMT) comprise contacting a cell with at least one calpain inhibitor that inhibits (such as, specifically inhibits) CAPN9 and/or CAPNS2. In some aspects, the cell is in a fibrotic tissue, a cancerous tissue, and/or tissue with high TGFβ signaling. In other aspects, the calpain inhibitor that inhibits (such as, specifically inhibits) CAPN9 and/or CAPNS2 is a small molecule chemical compound, antibody, peptide, peptidomimetic, protein or an RNA interfering agent such as, for example, an inhibitory nucleic acid, such as a short interfering RNA (siRNA).

Methods of treating a disease associated with myofibroblast differentiation (such as an EpMT or an EnMT-associated disease) in a subject in need thereof are also provided. In certain aspects, the methods include administering a therapeutically effective amount of at least one calpain inhibitor that inhibits (such as, specifically inhibits) CAPN9 and/or CAPNS2 to a subject having a disease associated with myofibroblast differentiation (such as an EpMT or an EnMT-associated disease). In some aspects, the disease associated with myofibroblast differentiation is a fibrotic disease or a secondary disease state or condition thereof, including liver fibrosis, renal fibrosis, lung fibrosis, hypersensitivity pneumonitis, interstitial fibrosis, systemic scleroderma, chronic allograft vasculopathy and/or chronic rejection in transplanted organs, ischemic-reperfusion injury associated fibrosis, macular degeneration, pancreatic fibrosis, fibrosis of the spleen, cardiac fibrosis, mediastinal fibrosis, myelofibrosis, endomyocardial fibrosis, retroperitoneal fibrosis, progressive massive fibrosis, nephrogenic systemic fibrosis, fibrotic complications of surgery, injection fibrosis, cirrhosis, diffuse parenchymal lung disease, post-vasectomy pain syndrome, stiff skin syndrome, and rheumatoid arthritis. In further aspects, the disease associated with myofibroblast differentiation is a cancer, particularly a cancer of epithelial origin, including breast cancer, basal cell carcinoma, adenocarcinoma, gastrointestinal cancer, lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body. In other aspects, the calpain inhibitor that inhibits (such as, specifically inhibits) CAPN9 and/or CAPNS2 is a small molecule chemical compound, antibody, peptide, peptidomimetic, protein or an inhibitory nucleic acid, such as an RNA interfering agent such as, for example, siRNA.

Methods of using a three-dimensional structure of a CAPN9/CAPNS2 heterodimer in a drug screening assay are also provided. In certain aspects the methods include: (a) selecting a potential drug by performing rational drug design with the three-dimensional structure of the CAPN9/CAPNS2 heterodimer determined from one or more sets of atomic coordinates, wherein the selection is performed in conjunction with computer modeling; (b) contacting the potential drug with the CAPN9/CAPNS2 heterodimer; (c) detecting the binding of the potential drug with the CAPN9/CAPNS2 heterodimer; and (d) detecting the inhibition of CAPN9/CAPNS2 heterodimer activity by the potential drug; wherein a potential drug is selected as a drug if the potential drug binds to and inhibits the CAPN9/CAPNS2 heterodimer. In another aspect, the CAPN9/CAPNS2 heterodimer includes a functional variant of CAPN9/CAPNS2, and detecting the binding of the inhibition of CAPN9/CAPNS2 heterodimer activity by the potential drug includes the use of a fluorescent calpain reporter substrate. In a further aspect, the selected drug that binds to and inhibits the CAPN9/CAPNS2 heterodimer is further counter-screened using CAPN1/CAPNS1 and/or CAPN2/CAPNS1 and/or CAPN1 and/or mini-CAPN1 and/or CAPN2 and/or mini-CAPN2 and/or functional variants thereof, wherein a drug that does not bind to and inhibit CAPN1/CAPNS1 and/or CAPN2/CAPNS1 and/or functional variants thereof is selected as a CAPN9/CAPNS2 inhibitor (such as a CAPN9/CAPNS2 specific inhibitor).

Methods of using a three-dimensional structure of CAPN9 and/or mini-CAPN9 in a drug screening assay are also provided. In certain aspects the methods include: (a) selecting a potential drug by performing rational drug design with the three-dimensional structure of CAPN9 and/or mini-CAPN9 determined from one or more sets of atomic coordinates, wherein the selection is performed in conjunction with computer modeling; (b) contacting the potential drug with CAPN9 and/or mini-CAPN9; (c) detecting the binding of the potential drug with CAPN9 and/or mini-CAPN9; and (d) detecting the stability of CAPN9 and/or mini-CAPN9; wherein a potential drug is selected as a drug if the potential drug binds to and stabilizes CAPN9 and/or mini-CAPN9.

Methods of using a three-dimensional structure of CAPNS2 in a drug screening assay are also provided. In certain aspects the methods include: (a) selecting a potential drug by performing rational drug design with the three-dimensional structure of CAPNS2 determined from one or more sets of atomic coordinates, wherein the selection is performed in conjunction with computer modeling; (b) contacting the potential drug with CAPNS2; (c) detecting the binding of the potential drug with CAPNS2; and (d) detecting the stability of CAPNS2; wherein a potential drug is selected as a drug if the potential drug binds to and stabilizes CAPNS2.

In another aspect, also provided herein are methods for identifying an agent capable of modulating the activity of CAPN9 and/or CAPNS2 in a cell that has yet to undergo, is undergoing, or has undergone myofibroblast differentiation, the method comprising: contacting the cell with the agent, wherein the cell expresses CAPN9 and/or CAPNS2; and identifying whether the agent modulates the activity of CAPN9 and/or CAPNS2. In some embodiments, myofibroblast differentiation comprises Epithelial-to-Mesenchymal Transition, Endothelial-to-Mesenchymal Transition, or Fibroblast-to-Myofibroblast Transition (FMT). In some embodiments of any of the embodiments provided herein, the agent is selected from the group consisting of an antibody or functional fragment thereof, a small molecule chemical compound, a non-antibody peptide, and an inhibitory nucleic acid. In some embodiments, the inhibitory nucleic acid is an antisense nucleic acid, a ribozyme, a small interfering RNA (siRNA), a short hairpin RNA or small hairpin RNA (shRNA), a microRNA (miRNA), a post-transcriptional gene silencing RNA (ptgsRNA), an antisense nucleotides, an aptamer, or a CRISPR RNA. In some embodiments, the inhibitory nucleic acid comprises at least one modified backbone and/or a non-natural internucleoside linkage. In some embodiments of any of the embodiments provided herein, modulating the activity of CAPN9 and/or CAPNS2 comprises decreasing the expression of a CAPN9 and/or CAPNS2 mRNA or a CAPN9 and/or CAPNS2 protein. In some embodiments, decreased CAPN9 and/or CAPNS2 mRNA expression is determined by Northern Blot, in situ hybridization, SAGE, RT-PCR, or another PCR-based method. In some embodiments, decreased CAPN9 and/or CAPNS2 protein expression is determined by immunohistochemistry, immunocytochemistry, ELISA, RIA, Western Blot, or another antibody-based method. In some embodiments of any of the embodiments provided herein, modulating the activity of CAPN9 and/or CAPNS2 comprises modulating the activity or expression levels of a protein selected from the group consisting of smooth muscle actin (α-SMA), calcineurin, calpastatin, E-cadherin, collagen, and one or more matrix metalloproteinases. In some embodiments, modulating the activity of CAPN9 and/or CAPNS2 decreases the activity or expression levels of one or more of α-SMA, calcineurin, collagen, and/or one or more matrix metalloproteinases. In some embodiments, modulating the activity of CAPN9 and/or CAPNS2 prevents or decreases cleavage of calcineurin into a constitutively active form. In some embodiments, modulating the activity of CAPN9 and/or CAPNS2 increases or maintains the activity or expression level of calpastatin and/or E-cadherin. In some embodiments of any of the embodiments provided herein, the agent inhibits the activity or expression of TRPM7. In some embodiments of any of the embodiments provided herein, modulating the activity of CAPN9 and/or CAPNS2 comprises disrupting an interaction between the CAPN9 and CAPNS2 proteins. In some embodiments of any of the embodiments provided herein, the cell is an endothelial cell, an epithelial cell, a fibroblast, or a myofibroblast. In some embodiments of any of the embodiments provided herein, the cell is an NMuMG cell. In some embodiments of any of the embodiments provided herein, the agent suppresses bleomycin-induced lung fibrosis carbon tetrachloride-induced liver fibrosis, thioacetamide-induced liver fibrosis, dimethylnitrosamine-induced liver fibrosis, bile duct ligation-induced liver fibrosis, unilateral ureter obstruction induced liver fibrosis, 5/6 nephrectomy induced kidney fibrosis, diabetes-induced kidney and liver fibrosis, streptozotocin-induced kidney fibrosis, western high fat induced kidney and liver fibrosis, combined western high fat diet and streptozotocin-induced liver and kidney fibrosis.

In further aspects, provided herein are methods for identifying a subject who would benefit from treatment with a CAPN9 and/or CAPNS2 inhibitor, the method comprising: assaying for the presence of a CAPN9 and/or CAPNS2 mRNA or protein in a biological sample obtained from the subject, wherein the presence of CAPN9 and/or CAPNS2 mRNA or protein in the biological sample identifies the subject as benefiting from treatment with a CAPN9 and/or CAPNS2 inhibitor. In some embodiments, the sample comprises at least one epithelial cell, at least one endothelial cell, and/or at least one fibroblast. In some embodiments, the sample comprises at least one myofibroblast. In some embodiments of any of the embodiments provided herein, the biological sample is fixed, paraffin embedded, fresh, or frozen. In some embodiments, the biological sample is obtained by needle, surgical, or core biopsy, PBMC, ascites, bile, urine, feces, sputum, induced sputum, fine needle aspiration, tumor resection, BAL fluid, or isolated from whole blood, platelet rich plasma, plasma, and/or serum. In some embodiments of any of the embodiments provided herein, the subject is diagnosed with or suspected of having one or more diseases associated with myofibroblast differentiation, wherein the disease associated with myofibroblast differentiation is a fibrotic disease selected from the group consisting of liver fibrosis, renal fibrosis, lung fibrosis, hypersensitivity pneumonitis, ischemic-reperfusion injury, interstitial fibrosis, systemic scleroderma, chronic allograft vasculopathy and/or chronic rejection in transplanted organs, ischemic-reperfusion injury associated fibrosis, macular degeneration, pancreatic fibrosis, fibrosis of organ transplant recipients, fibrosis of the spleen, cardiac fibrosis, mediastinal fibrosis, myelofibrosis, endomyocardial fibrosis, retroperitoneal fibrosis, progressive massive fibrosis, nephrogenic systemic fibrosis, fibrotic complications of surgery, injection fibrosis, cirrhosis, diffuse parenchymal lung disease, post-vasectomy pain syndrome, stiff skin syndrome, and rheumatoid arthritis. In some embodiments of any of the embodiments provided herein, the subject is diagnosed with one or more diseases associated with myofibroblast differentiation, wherein the disease associated with myofibroblast differentiation is a cancer of epithelial origin selected from the group consisting of breast cancer, basal cell carcinoma, adenocarcinoma, gastrointestinal cancer, lip cancer, mouth cancer, esophageal cancer, small bowel cancer, stomach cancer, colon cancer, liver cancer, brain, bladder cancer, pancreas cancer, ovary cancer, cervical cancer, lung cancer, skin cancer, prostate cancer, and renal cell carcinoma.

In yet other aspects, provided herein are methods for determining if a subject diagnosed with one or more diseases associated with myofibroblast differentiation is responding to treatment with a CAPN9 and/or CAPNS2 inhibitor, the method comprising: determining if the expression or activity of CAPN9 and/or CAPNS2 is modulated in a biological sample obtained from the subject following administration of the CAPN9 and/or CAPNS2 inhibitor, wherein the subject is responding to treatment if the activity of CAPN9 and/or CAPNS2 in the biological sample is modulated. In some embodiments, modulating the activity of CAPN9 and/or CAPNS2 comprises decreasing the expression of a CAPN9 and/or CAPNS2 mRNA or a CAPN9 and/or CAPNS2 protein. In some embodiments of any of the embodiments provided herein, modulating the activity of CAPN9 and/or CAPNS2 comprises modulating the activity or expression levels of a protein selected from the group consisting of smooth muscle actin ($\alpha$-SMA), vimentin, calcineurin, calpastatin, E-cadherin, collagen, and one or more matrix metalloproteinases. In some embodiments, modulating the activity of CAPN9 and/or CAPNS2 decreases the activity or expression level of one or more of $\alpha$-SMA, vimentin, calcineurin, collagen, and/or one or more matrix metalloproteinases. In some embodiments, modulating the activity of CAPN9 and/or CAPNS2 prevents or decreases cleavage of calcineurin into a constitutively active form. In some embodiments, modulating the activity of CAPN9 and/or CAPNS2 increases or maintains the activity or expression level of calpastatin and/or E-cadherin. In some embodiments, the inhibitor inhibits the activity or expression of TRPM7. In some embodiments, modulating the activity of CAPN9 and/or CAPNS2 comprises disrupting an interaction between the CAPN9 and CAPNS2 proteins. In some embodiments of any of the embodiments provided herein, the sample comprises at least one epithelial cell, at least one endothelial cell, and/or at least one fibroblast. In some embodiments of any of the embodiments provided herein, the sample comprises at least one myofibroblast. In some embodiments of any of the embodiments provided herein, the biological sample is fixed, paraffin embedded, fresh, or frozen. In some embodiments, the biological sample is obtained by needle or core biopsy, fine needle aspiration, tumor resection, or isolated from serum.

In another aspect, provided herein are methods for identifying whether a subject diagnosed with one or more diseases associated with myofibroblast differentiation will benefit from treatment with a calcineurin inhibitor, the method comprising: assaying for the presence of a CAPN9 and/or CAPNS2 mRNA or protein in a biological sample obtained from the subject, wherein the presence of CAPN9 and/or CAPNS2 mRNA or protein in the biological sample identifies the subject as benefiting from treatment with a calcineurin inhibitor. In some embodiments, the sample comprises at least one epithelial cell, at least one endothelial cell, and/or at least one fibroblast. In some embodiments, the sample comprises at least one myofibroblast. In some embodiments of any of the embodiments provided herein, the biological sample is fixed, paraffin embedded, fresh, or frozen. In some embodiments, the biological sample is obtained by needle surgical, or core biopsy, PBMC, ascites, bile, urine, feces, sputum, induced sputum, fine needle aspiration, tumor resection, BAL fluid, or isolated from whole blood, platelet rich plasma, plasma, and/or serum. In some embodiments of any of the embodiments provided herein, the subject is diagnosed with one or more diseases associated with myofibroblast differentiation, wherein the disease associated with myofibroblast differentiation is a fibrotic disease selected from the group consisting of liver fibrosis, renal fibrosis, lung fibrosis, hypersensitivity pneumonitis, ischemic-reperfusion injury, interstitial fibrosis, systemic scleroderma, chronic allograft vasculopathy and/or chronic rejection in transplanted organs, ischemic-reperfusion injury associated fibrosis, macular degeneration, pancreatic fibrosis, fibrosis of organ transplant recipients, fibrosis of the spleen, cardiac fibrosis, mediastinal fibrosis, myelofibrosis, endomyocardial fibrosis, retroperitoneal fibrosis, progressive massive fibrosis, nephrogenic systemic fibrosis, fibrotic complications of surgery, injection fibrosis, cirrhosis, diffuse parenchymal lung disease, post-vasectomy pain syndrome, stiff skin syndrome, and rheumatoid arthritis. In some embodiments of any of the embodiments provided herein, the subject is diagnosed with one or more diseases associated with myofibroblast differentiation, wherein the disease associated with myofibroblast differentiation is a cancer of epithelial origin selected from the group consisting of breast cancer, basal cell carcinoma, adenocarcinoma, gastrointestinal cancer, lip cancer, mouth cancer, esophageal cancer, small bowel cancer, stomach cancer, colon cancer, liver cancer, brain, bladder cancer, pancreas cancer, ovary cancer, cervical cancer, lung cancer, skin cancer, prostate cancer, and renal cell carcinoma.

In still further aspects, provided herein are methods of treating a subject diagnosed with or suspected of having one or more diseases associated with myofibroblast differentiation, the method comprising: assaying for the presence of a CAPN9 and/or CAPNS2 mRNA or protein in a biological sample obtained from the subject; and administering a CAPN9 and/or CAPNS2 inhibitor to the subject. In some embodiments, the CAPN9 and/or CAPNS2 inhibitor is administered in combination with at least one anti-cancer agent.

In another aspect, provided herein are methods for identifying an agent capable of inhibiting of a TRP calcium channel, wherein inhibition of the TRP calcium channel prevents myofibroblast differentiation, the method comprising: contacting a cell with the agent, wherein the cell expresses (i) CAPN9 and/or CAPNS2 and (ii) a TRP calcium channel; and identifying whether the agent prevents myofibroblast differentiation. In some embodiments, the agent prevents calcium influx into the cell. In some embodiments of any of the embodiments provided herein, myofibroblast differentiation comprises Epithelial-to-Mesenchymal Transition, Endothelial-to-Mesenchymal Transition, or Fibroblast-to-Myofibroblast Transition (FMT). In some embodiments of any of the embodiments provided herein, the agent is selected from the group consisting of an antibody or fragment thereof, a small molecule chemical compound, a non-antibody peptide, and an inhibitory nucleic acid. In some embodiments of any of the embodiments provided herein, preventing myofibroblast differentiation comprises altering the activity or expression levels of a protein selected from the group consisting of smooth muscle actin (α-SMA), vimentin, calcineurin, calpastatin, E-cadherin, collagen, and one or more matrix metalloproteinases. In some embodiments of any of the embodiments provided herein, preventing myofibroblast differentiation comprises decreasing the activity or expression level of one or more of α-SMA, vimentin, calcineurin, collagen, and/or one or more matrix metalloproteinases. In some embodiments, preventing myofibroblast differentiation comprises preventing or decreasing cleavage of calcineurin into a constitutively active form. In some embodiments, preventing myofibroblast differentiation comprises increasing or maintaining the activity or expression level of calpastatin and/or E-cadherin. In some embodiments of any of the embodiments provided herein, preventing myofibroblast differentiation comprises disrupting the interaction between CAPN9 and CAPNS2. In some embodiments of any of the embodiments provided herein, the cell is an endothelial cell, an epithelial cell, a fibroblast, or a myofibroblast. In some embodiments of any of the embodiments provided herein, myofibroblast differentiation is TGFβ-mediated myofibroblast differentiation.

In another aspect, provided herein are methods for treating a fibrotic disease associated with myofibroblast differentiation in a subject in need thereof comprising administering to the subject a therapeutically effective amount of at least one agent that decreases the level and/or activity of CAPN9 and/or CAPNS2. In some embodiments, the at least one agent specifically inhibits CAPN9 and/or CAPNS2. In some embodiments, the at least one agent decreases TRPM7-mediated calcium influx. In some embodiments, the at least one agent specifically inhibits TRPM7. In some embodiments, the at least one agent inhibits Fibroblast-to-Myofibroblast Transition (FMT). In some embodiments, the fibrotic disease associated with myofibroblast differentiation is a TGFβ-mediated disease. In some embodiments, the fibrotic disease is liver fibrosis. In some embodiments, the fibrotic disease is lung fibrosis. In some embodiments, the fibrotic disease is systemic scleroderma. In some embodiments of any of the embodiments described herein, the at least one agent is a small molecule chemical compound. In some embodiments, the at least one agent is MDL-28170. In some embodiments of any of the embodiments described herein, the at least one agent is an RNA interfering agent. In some embodiments, the RNA interfering agent is an siRNA. In some embodiments of any of the embodiments described herein, the subject is a human subject. In some embodiments, the method further comprises the step of diagnosing the subject as having a pathological level and/or activity of CAPN9 and/or CAPNS2.

In further aspects, also provided herein are methods for screening potential compounds or agents to identify a compound or agent that decreases the level and/or activity of CAPN9 and/or CAPNS2, the method comprising: contacting a population of cells or an extract thereof with at least one potential compound or agent, wherein the population of cells or an extract thereof express CAPN9 and/or CAPNS2; and assessing the ability of the at least one potential compound or agent to decrease level and/or activity of CAPN9 and/or CAPNS2 in the cells or extract thereof of the population, wherein if contact with the at least one potential compound or agent decreases the level and/or activity of CAPN9 and/or CAPNS2 relative to contact with a control compound or agent, the at least one potential compound or agent is identified as a compound or an agent that decreases the level and/or activity of CAPN9 and/or CAPNS2. In some embodiments, the population of cells is isolated from a subject with a fibrotic disease.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

All patents, patent applications, and other publications (e.g., scientific articles, books, websites, and databases)

mentioned herein are incorporated by reference in their entirety. In case of a conflict between the specification and any of the incorporated references, the specification (including any amendments thereof, which may be based on an incorporated reference), shall control. Standard art-accepted meanings of teems are used herein unless indicated otherwise. Standard abbreviations for various terms are used herein.

BRIEF DESCRIPTION OF THE DRAWINGS

Figure 1A:
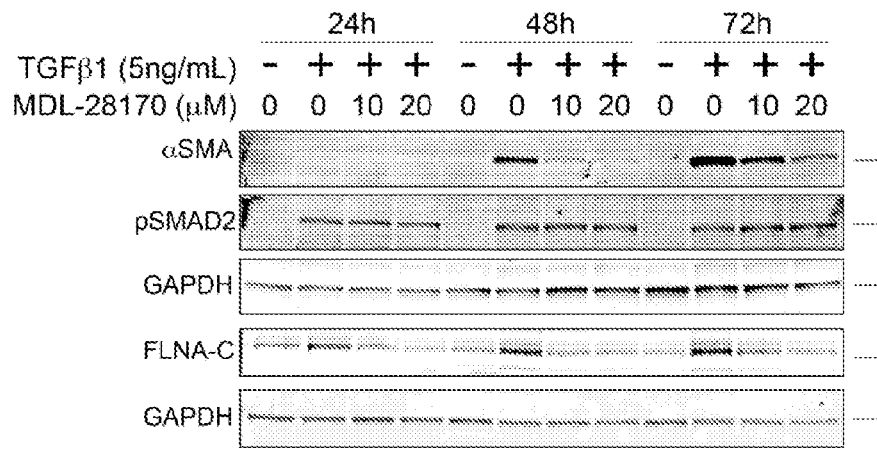
Figure 1B:
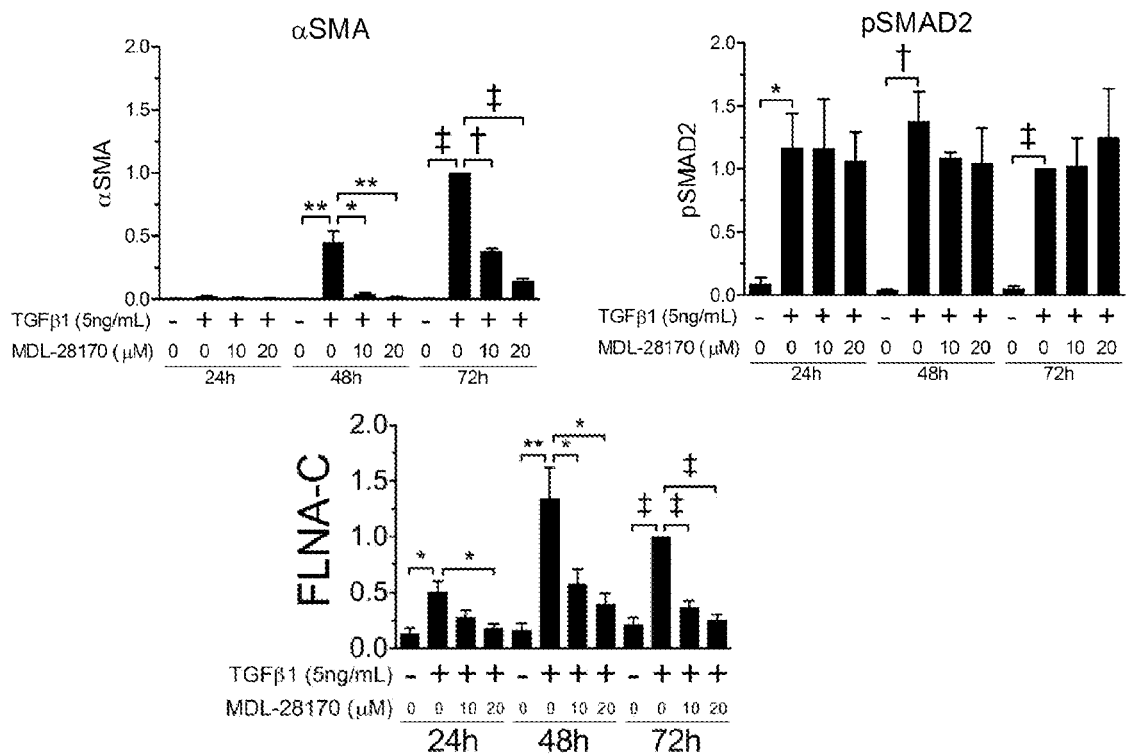
Figure 1C:
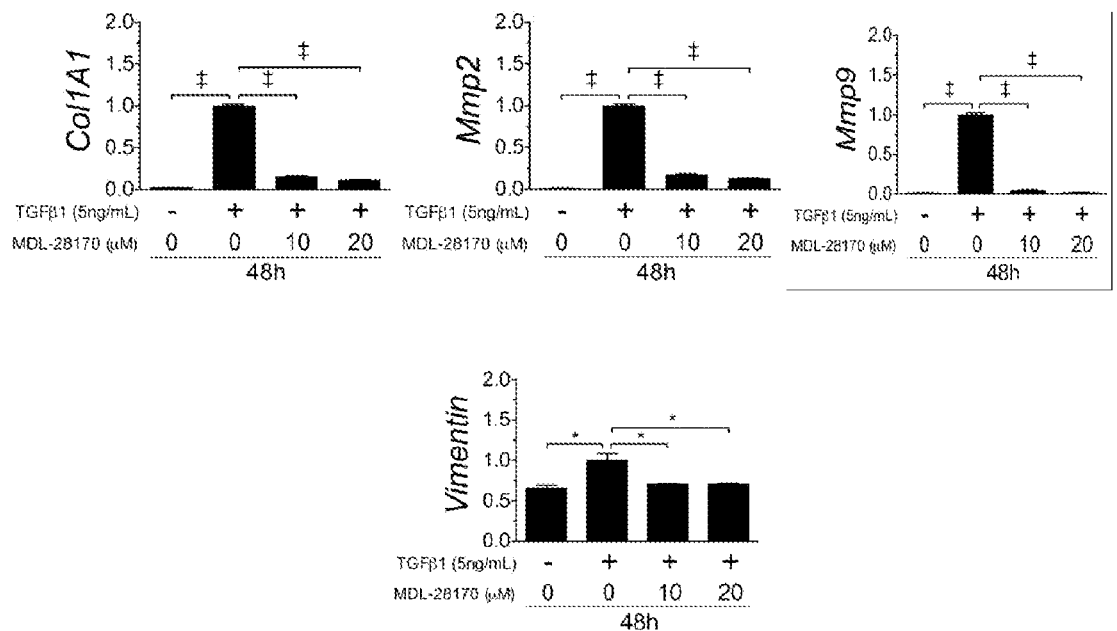
Figure 1D:
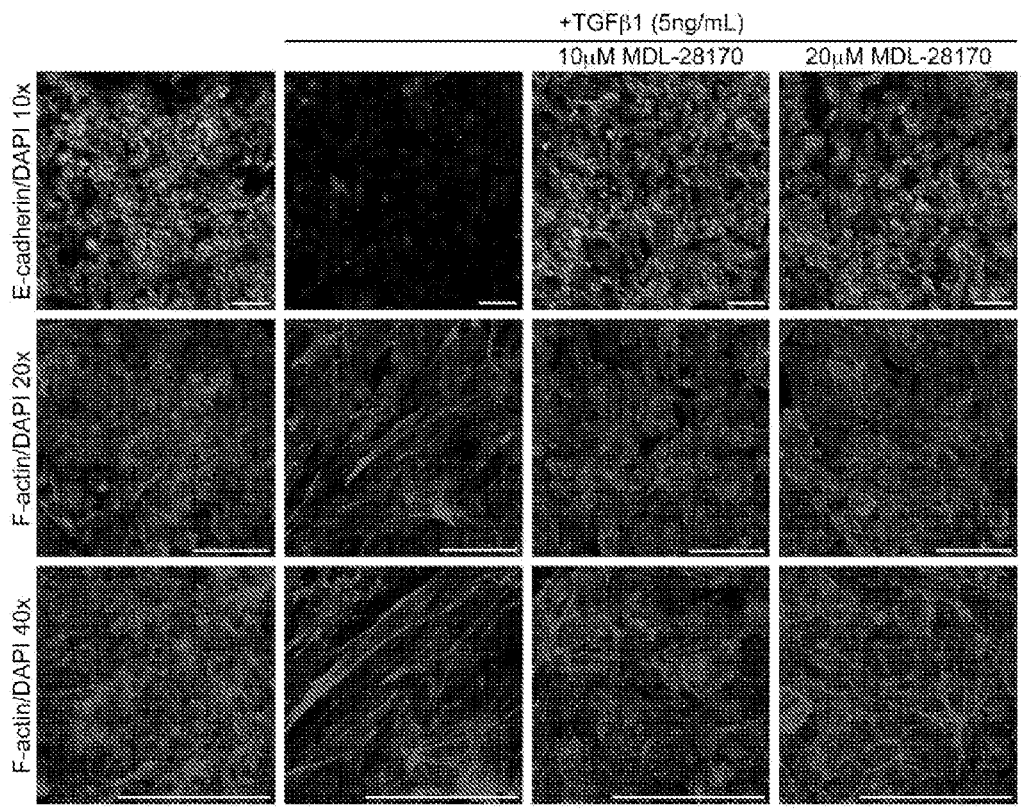
Figure 1E:
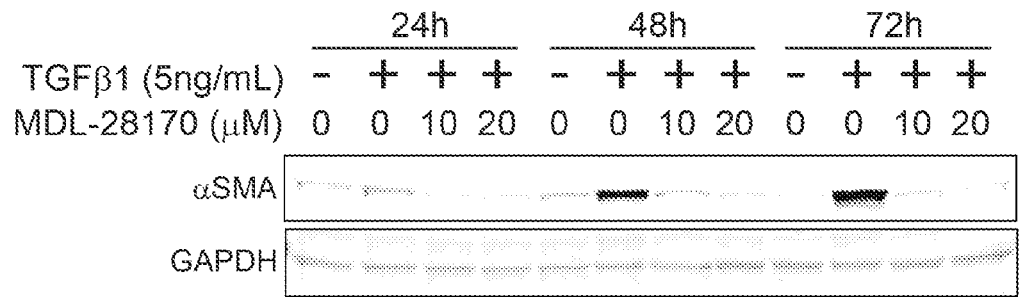
Figure 1F:
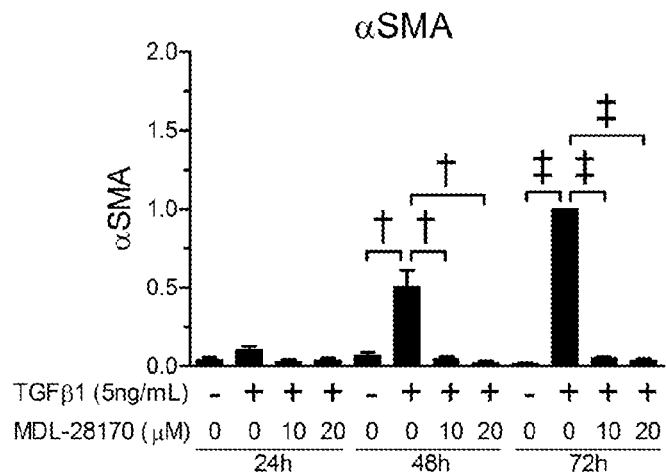
Figure 1G:
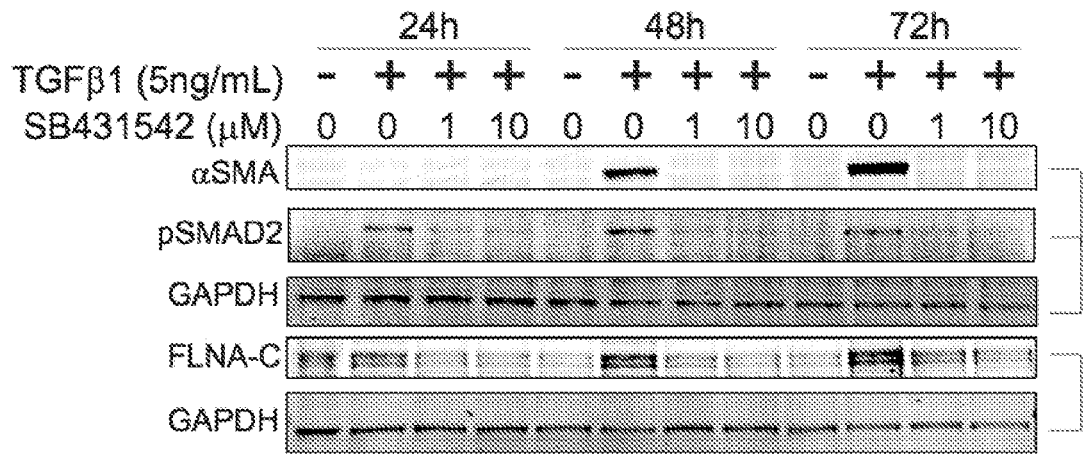
Figure 1H:
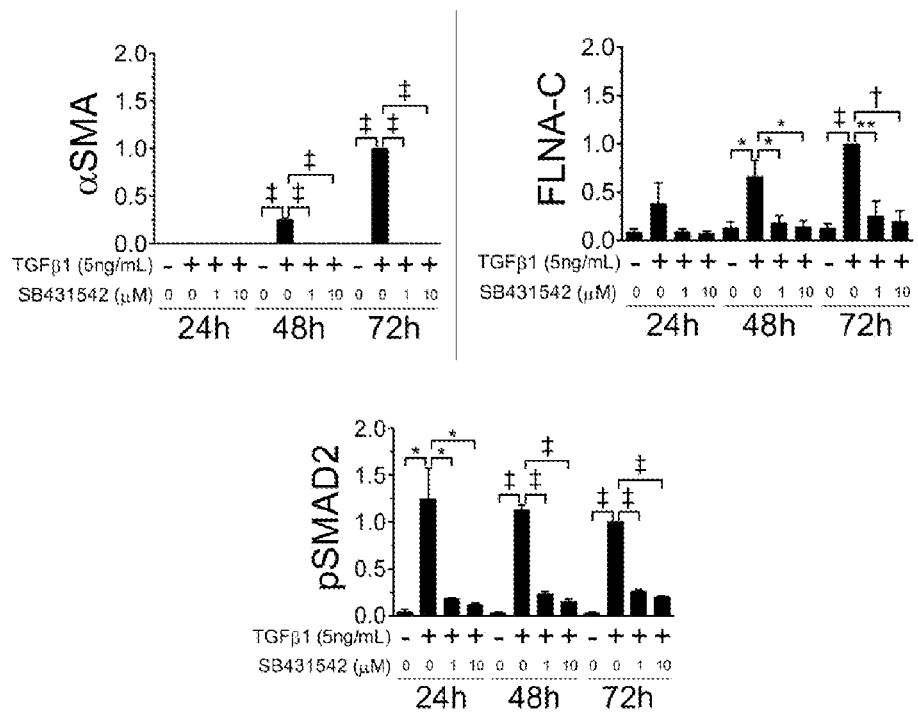
Figure 1I:
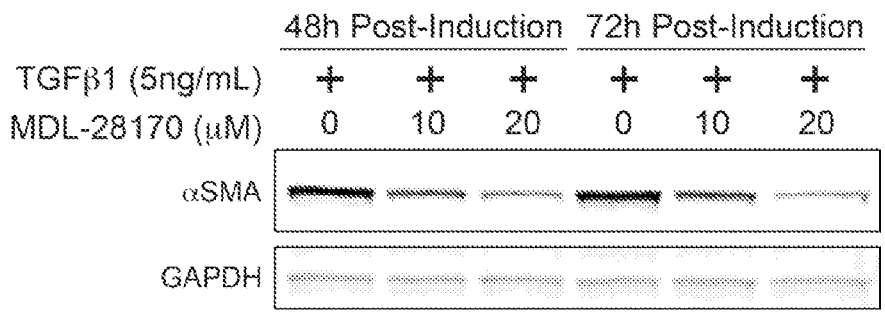
Figure 1J:
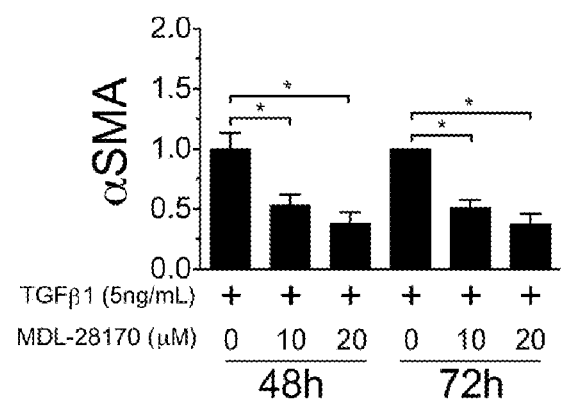
Figure 1:
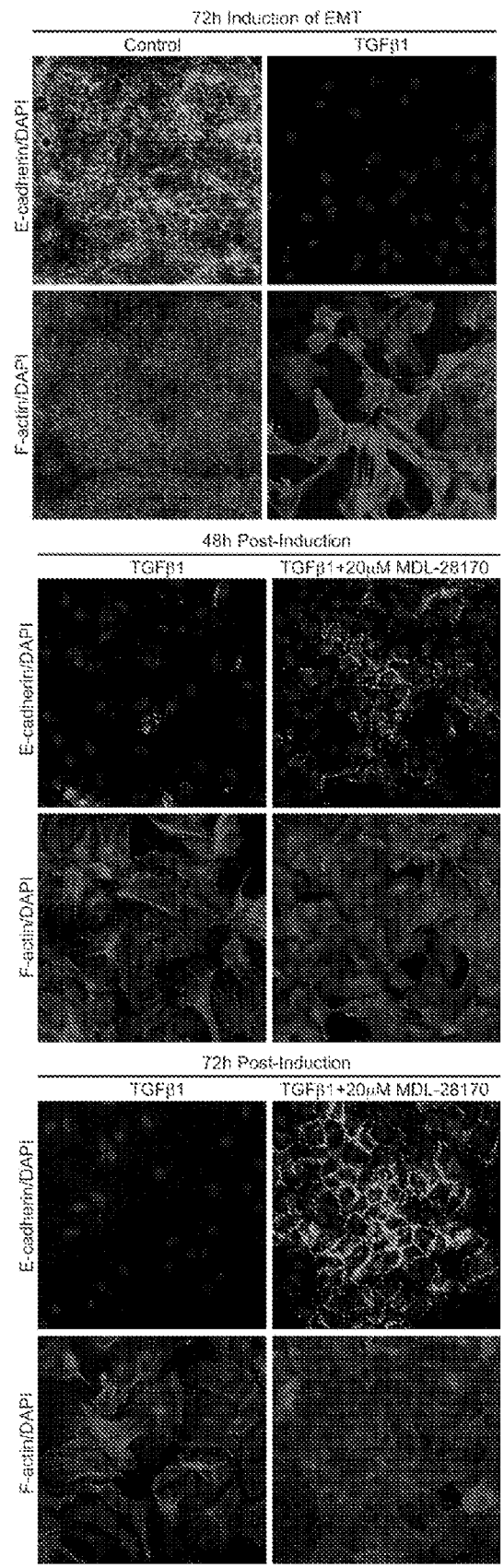

Having thus described the presently disclosed subject matter in general terms, reference will now be made to the accompanying Figures, which are not necessarily drawn to scale, and wherein:

FIG. 1A and FIG. 1B show that small molecule calpain inhibitor MDL-28170 suppresses TGFβ-induced EMT in NMuMG cells as measured from αSMA expression by western blot (FIG. 1A) and quantified western blot data done in biological replicates. (FIG. 1B; Levels were normalized to the 72 h TGFβ1 only treated sample for each blot. Students t-test *p<0.05, **p<0.01, † p<0.005, †† p<0.001). FIG. 1A and FIG. 1B. show the small molecule calpain inhibitor MDL-28170 suppressed TGFβ-induced calpain activity (as measured by cleavage of Filamin A, a known calpain substrate) without significantly affecting TGFβ-induced phosphorylation of SMAD2, as measured by western blot (FIG. 1A) and quantified western blot data done in biological replicates (FIG. 1B; Levels were normalized to the 72 h TGFβ1 only treated sample for each blot. Student's t-test *p<0.05, **p<0.01, † p<0.005, †† p<0.001). FIG. 1C shows that small molecule calpain inhibitor MDL-28170 suppresses TGFβ-induced expression of genes associated with myofibroblast differentiation and/or fibrosis, such as Col1A1, Vimentin, MMP2 and MMP9 by quantitative PCR (FIG. 1C; Levels normalized to the mean value of the TGFβ1-only treated sample. Student's t-test *p<0.05, **p<0.01, † p<0.005, †† p<0.001). FIG. 1D shows that morphological changes associated with TGFβ-induced mesenchymal transition, such as loss of E-cadherin/cell-cell adhesion and rearrangement of cortical actin into stress fibers, were suppressed by treatment with calpain inhibitor MDL-28170. (FIG. 1D; E-cadherin shown in green, F-actin shown in red, DAPI nuclear marker shown in blue. Scale bar=100 µM); FIG. 1E and FIG. 1F show that the small molecule calpain inhibitor MDL-28170 suppresses TGFβ-induced EMT in MDCK cells as measured from αSMA expression by western blot (FIG. 1E) and quantified western blot data of αSMA in biological replicates. (FIG. 1F; Levels were normalized to the 72 h TGFβ1 only sample for each blot. Student's t-test *p<0.05, **p<0.01, †p<0.005, †† p<0.001); FIG. 1G and FIG. 1H show that TGFβ receptor kinase inhibitor SB431542 suppresses TGFβ-induced EMT in NMuMG cells as measured from αSMA expression by western blot (FIG. 1G) and quantified western blot data done in biological replicates. (FIG. 1H; Levels were normalized to the 72 h TGFβ1 only treated sample for each blot. Students t-test *p<0.05, **p<0.01, † p<0.005, †† p<0.001). FIG. 1G and FIG. 1H show the small molecule calpain inhibitor SB431542 suppressed TGFβ-induced calpain activity (as measured by cleavage of Filamin A, a known calpain substrate) and TGFβ-induced phosphorylation of SMAD2, as measured by western blot (FIG. 1H) and quantified western blot data done in biological replicates (FIG. 1H; Levels were normalized to the 72 h TGFβ1 only treated sample for each blot. Student's t-test *p<0.05, **p<0.01, † p<0.005, †† p<0.001).). FIG. 1I and FIG. 1J show that calpain inhibitors can induce mesenchymal-to-epithelial transition. NMuMG cells pretreated with TGFβ1 for 72 hours to induce EMT, and then treated with calpain inhibitor MDL-28170 while in the continued presence of TGFβ1 for an additional 48 h or 72 h post-induction, can revert to a more epithelial phenotype as assessed by αSMA expression by western blot (FIG. 1I) and quantified western blot data done in biological replicates (FIG. 1J; Levels were normalized to TGFβ1 only treated samples within each time point. Students t-test *p<0.05). FIG. 1K shows NMuMG cells pretreated with TGFβ1 for 72 h for induction of EMT and then treated with calpain inhibitor MDL-28170 while in the continued presence of TGFβ1 for another 48 h or 72 h post-induction, reacquire expression of E-cadherin and rearrange stress fibers into a more cortical arrangement, adopting a more epithelial phenotype showing inhibition of calpain activity can reverse TGFβ-induced myofibroblast differentiation (FIG. 1K; E-cadherin shown in green, F-actin shown in red, DAPI nuclear marker shown in blue)

Figure 2A:
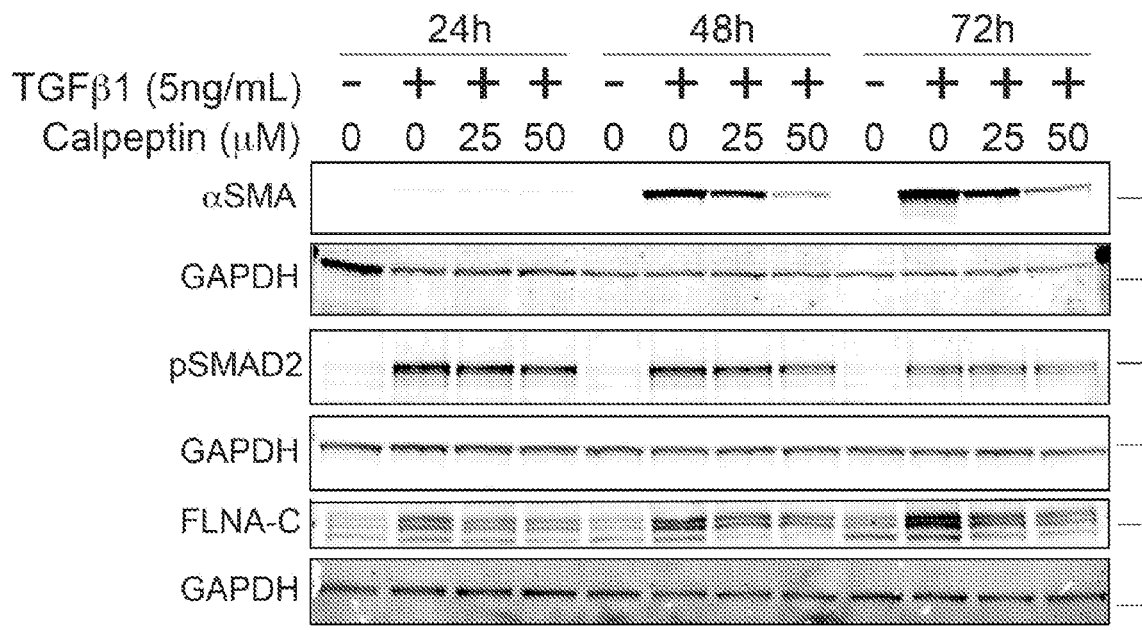
Figure 2B:
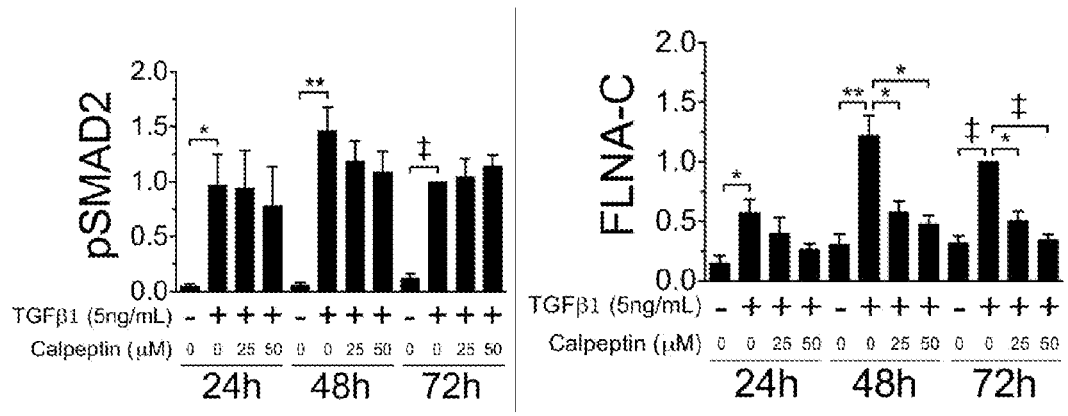
Figure 2B:
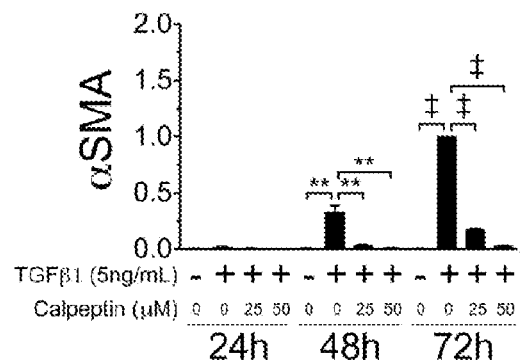

FIG. 2A and FIG. 2B show that small molecule calpain inhibitor calpeptin suppresses TGFβ-induced EMT in NMuMG cells as measured from αSMA expression by western blot (FIG. 2A) and quantified western blot data done in biological replicates. (FIG. 2B; Levels were normalized to the 72 h TGFβ1 only treated sample for each blot. Students t-test *p<0.05, **p<0.01, † p<0.005, †† p<0.001). FIG. 2A and FIG. 2B. show the small molecule calpain inhibitor calpeptin suppressed TGFβ-induced calpain activity (as measured by cleavage of Filamin A, a known calpain substrate) without significantly affecting TGFβ-induced phosphorylation of SMAD2, as measured by western blot (FIG. 2A) and quantified western blot data done in biological replicates (FIG. 2B; Levels were normalized to the 72 h TGFβ1 only treated sample for each blot. Student's t-test *p<0.05, **p<0.01, † p<0.005, †† p<0.001).

Figure 3A:
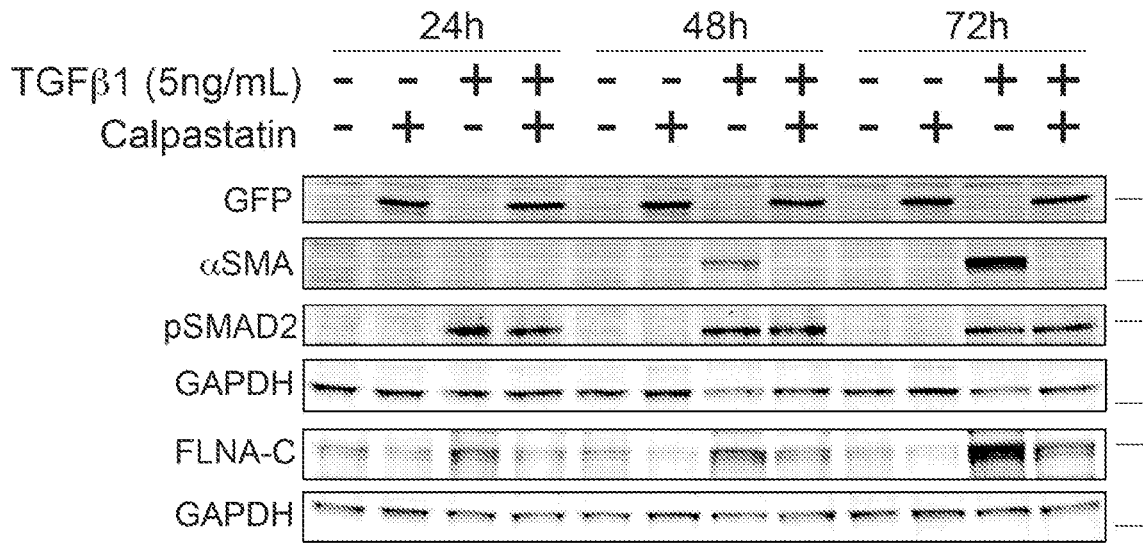
Figure 3B:
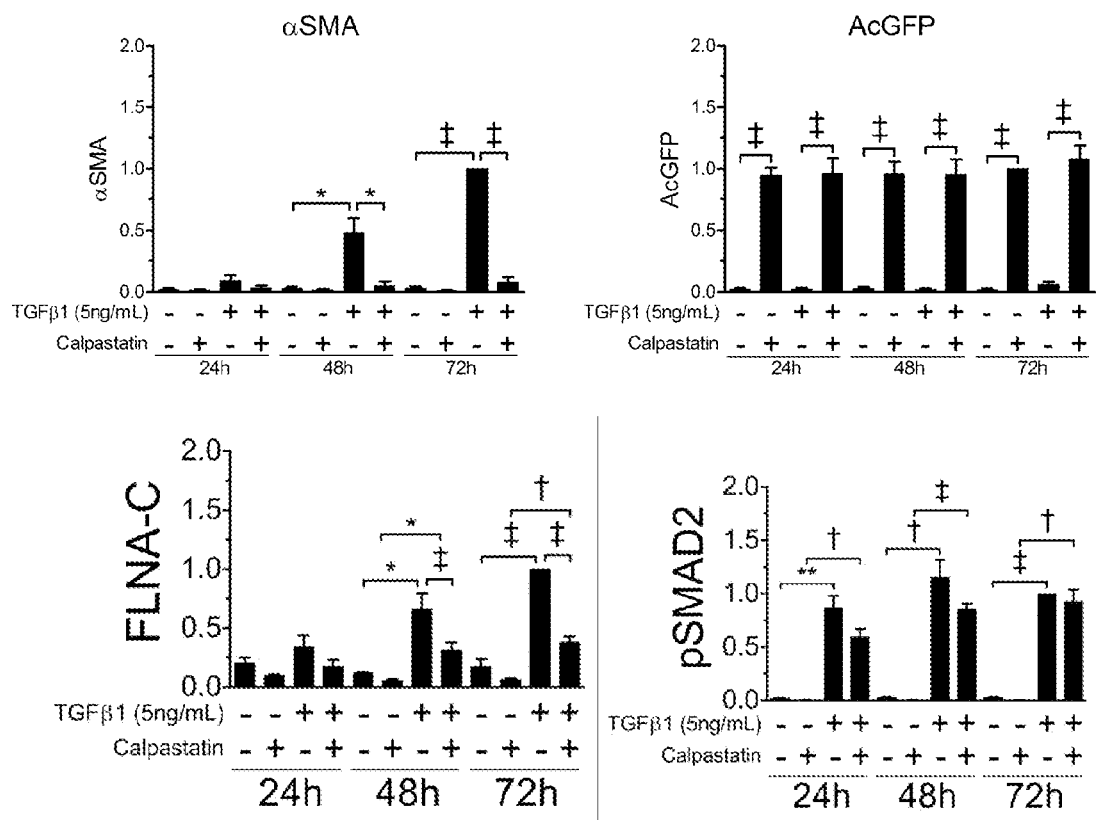
Figure 4A:
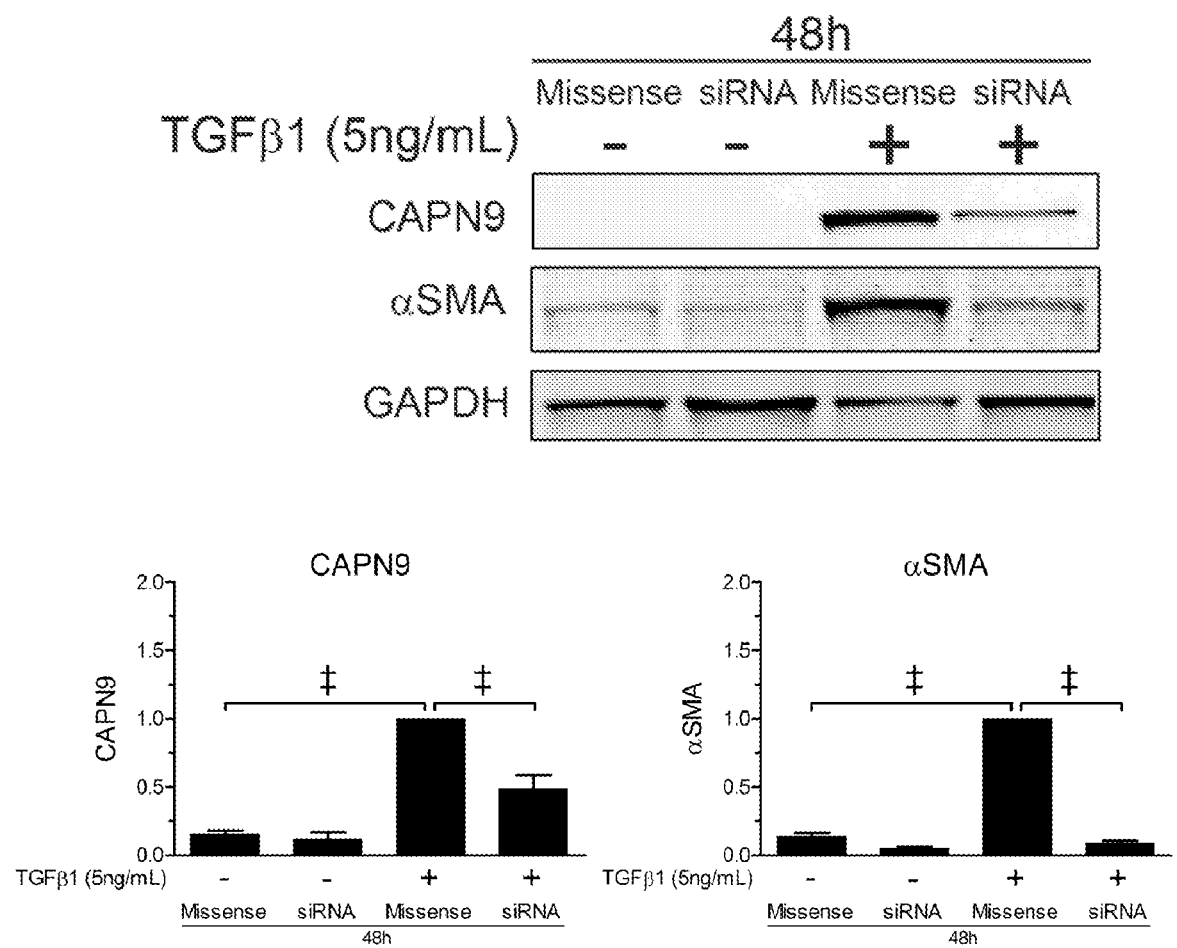
Figure 4B:
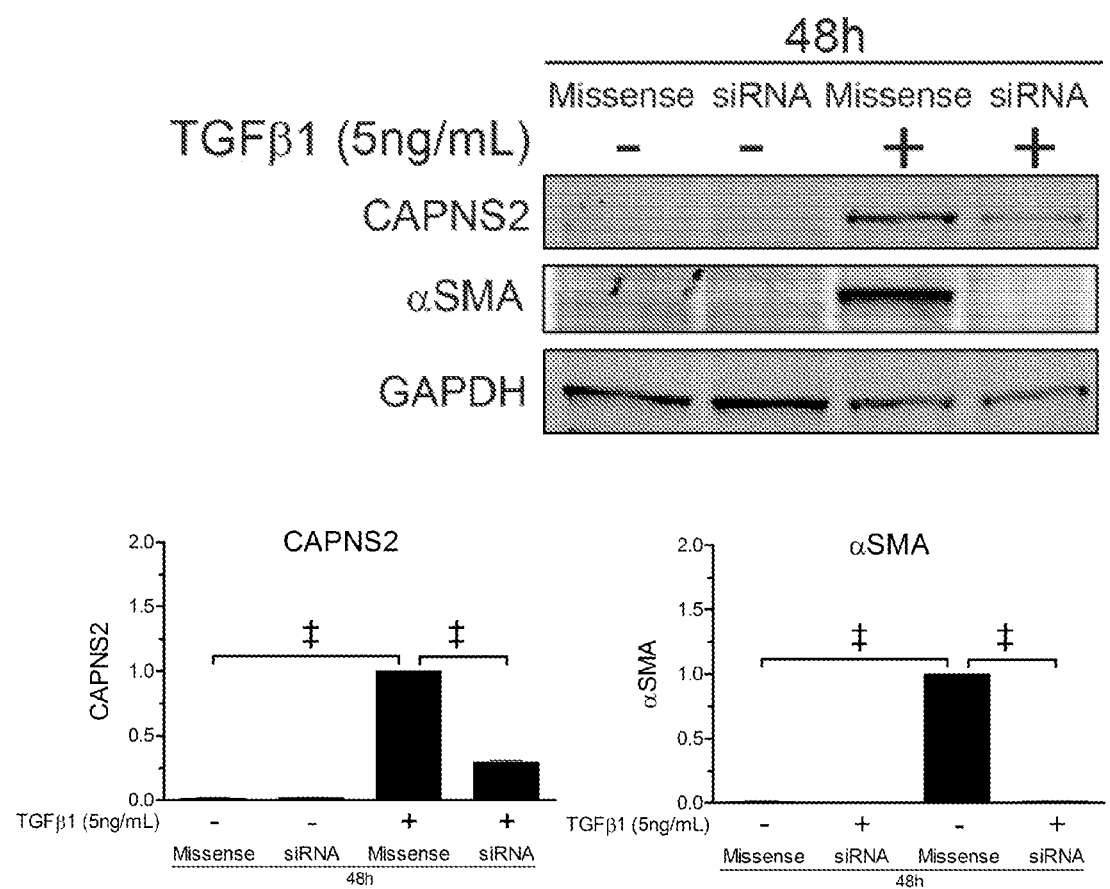
Figure 5A:
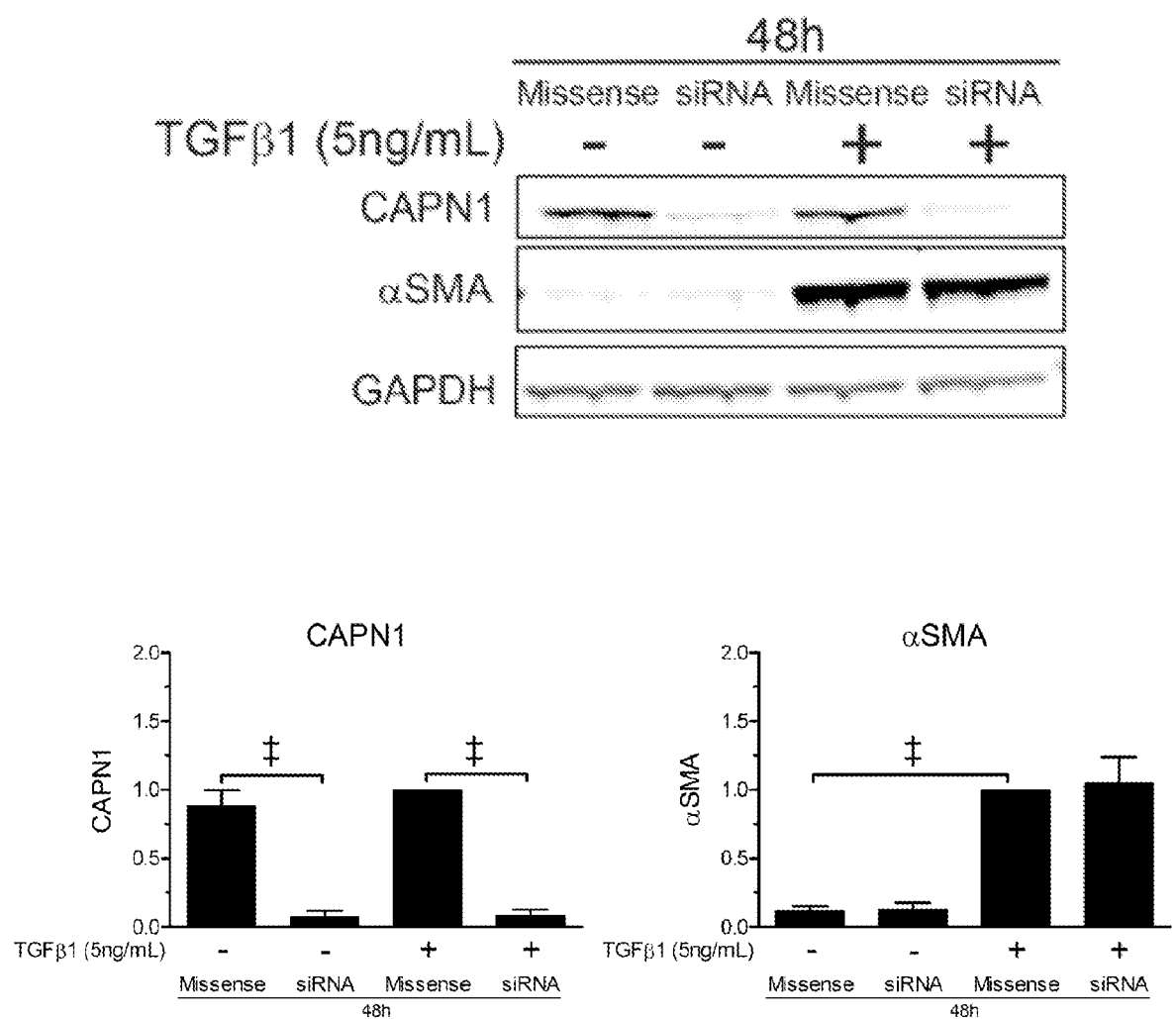
Figure 5B:
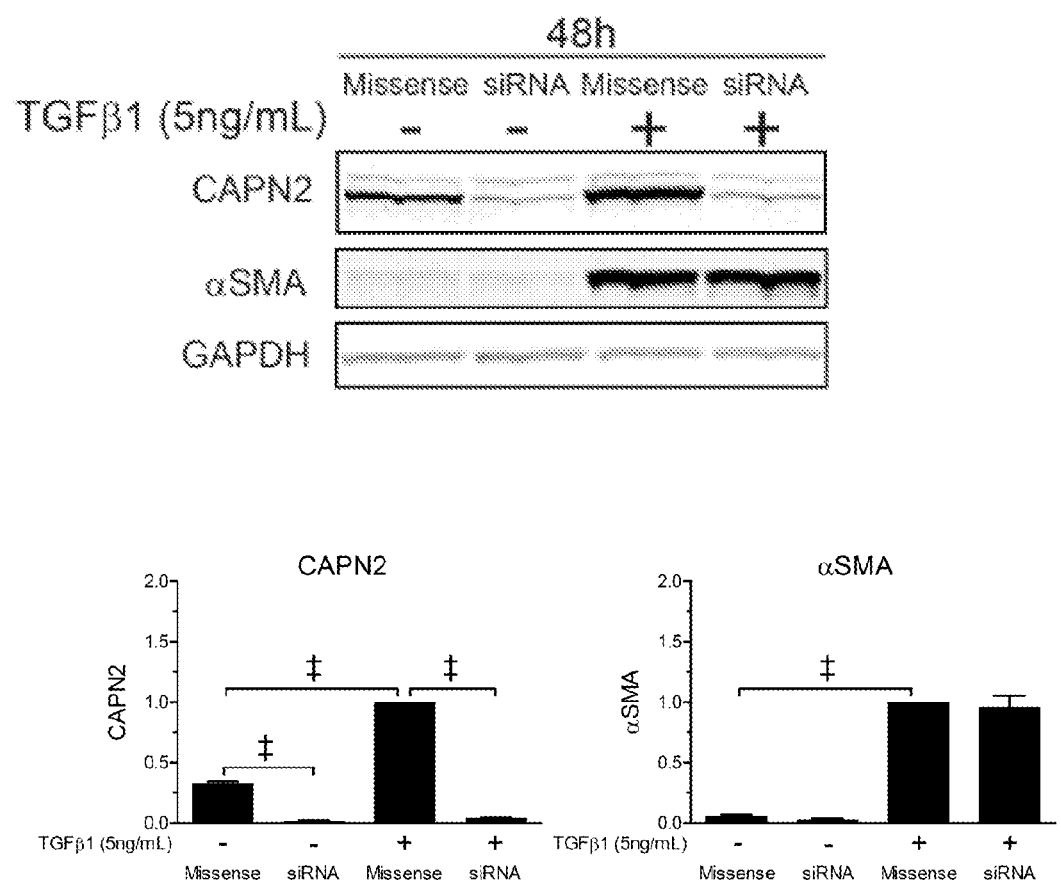
Figure 5C:
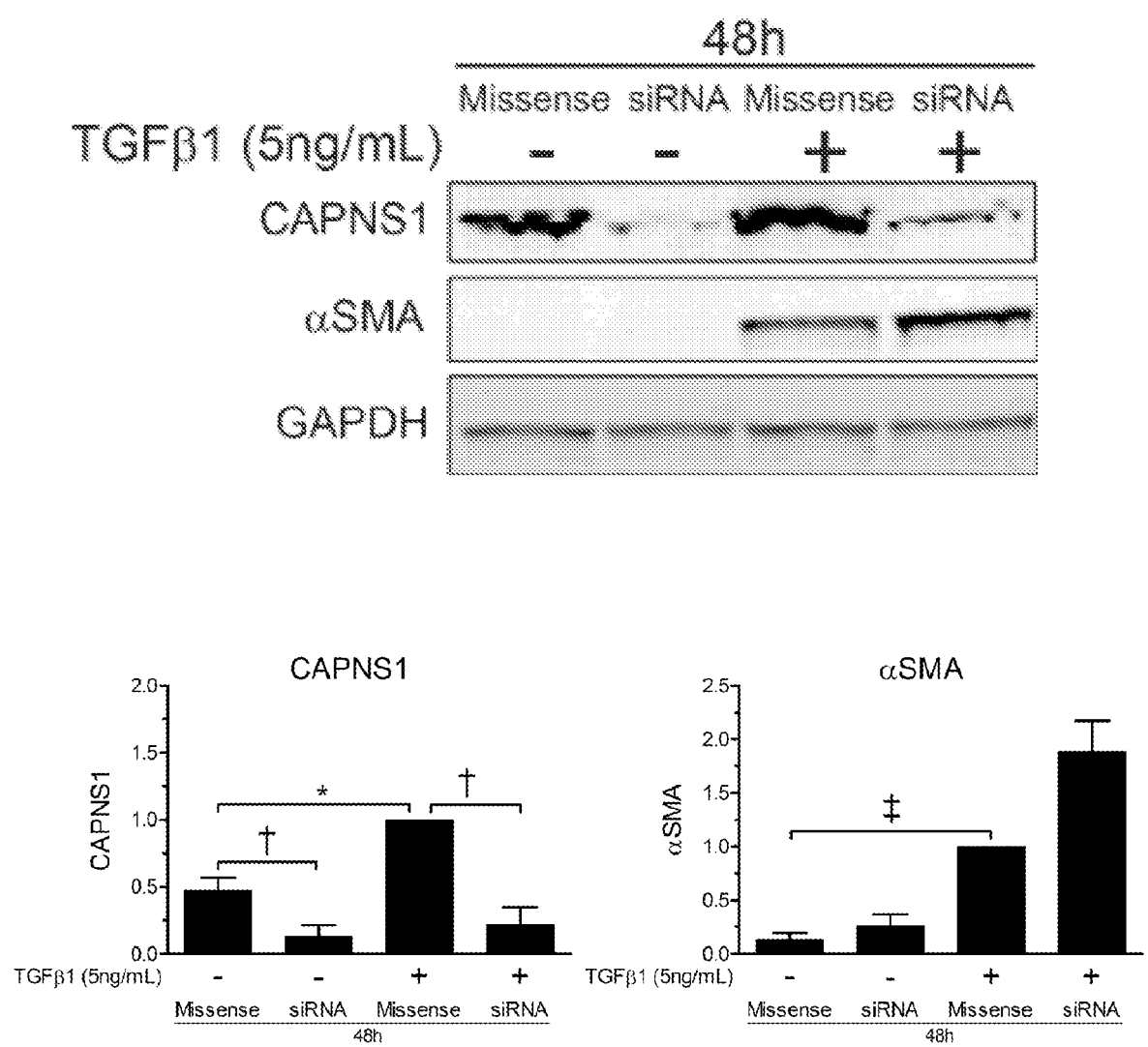
Figure 6A:
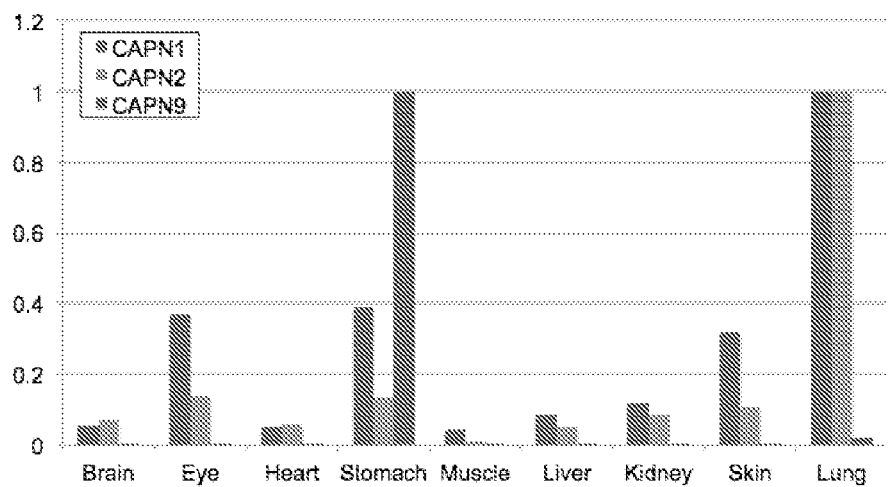
Figure 6B:
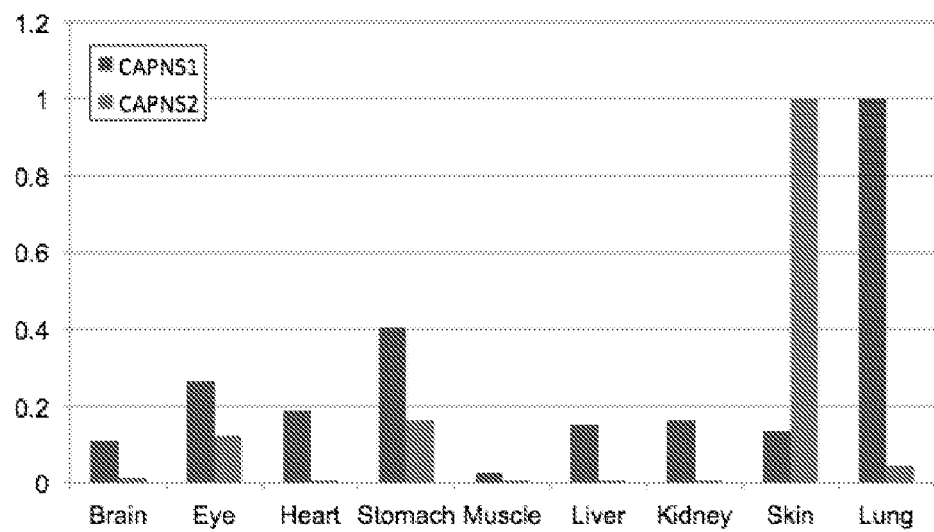
Figure 7A:
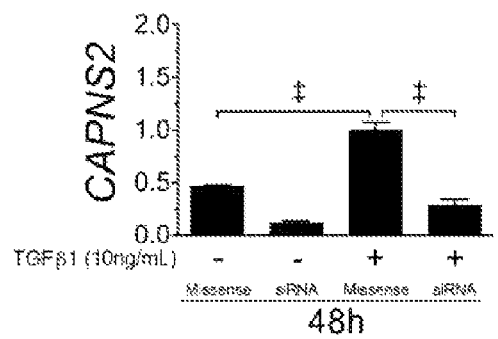
Figure 7A:
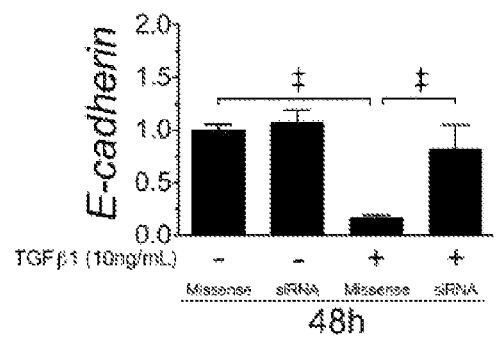
Figure 7A:
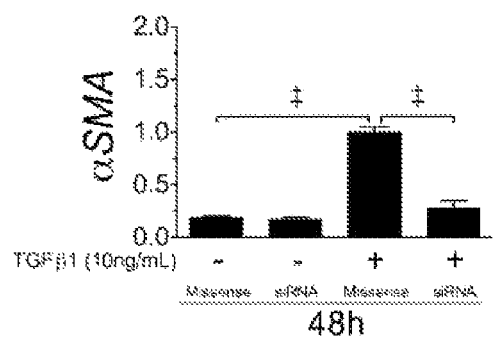
Figure 7A:
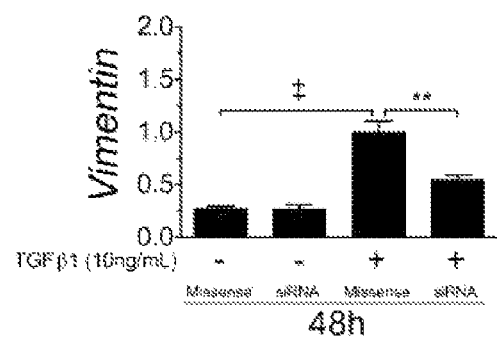
Figure 7A:
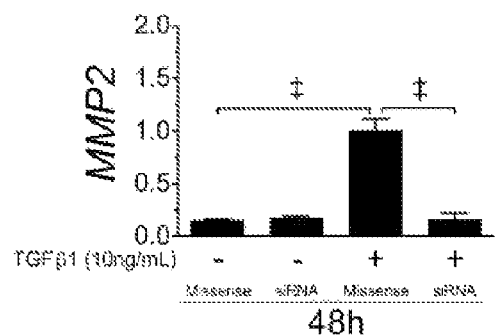
Figure 7A:
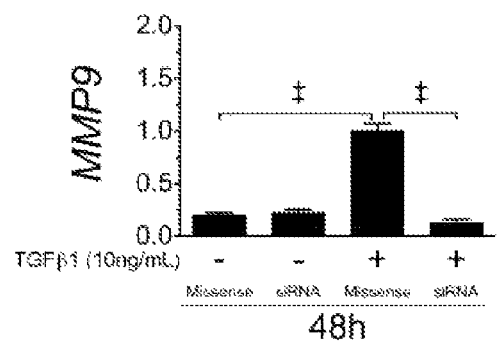
Figure 7B:
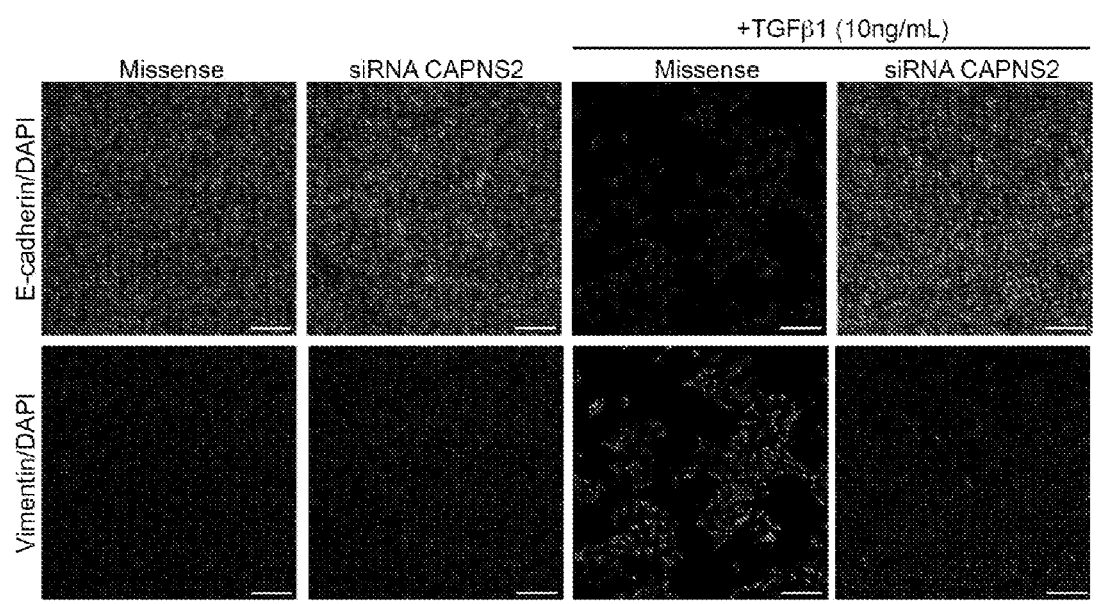
Figure 7C:
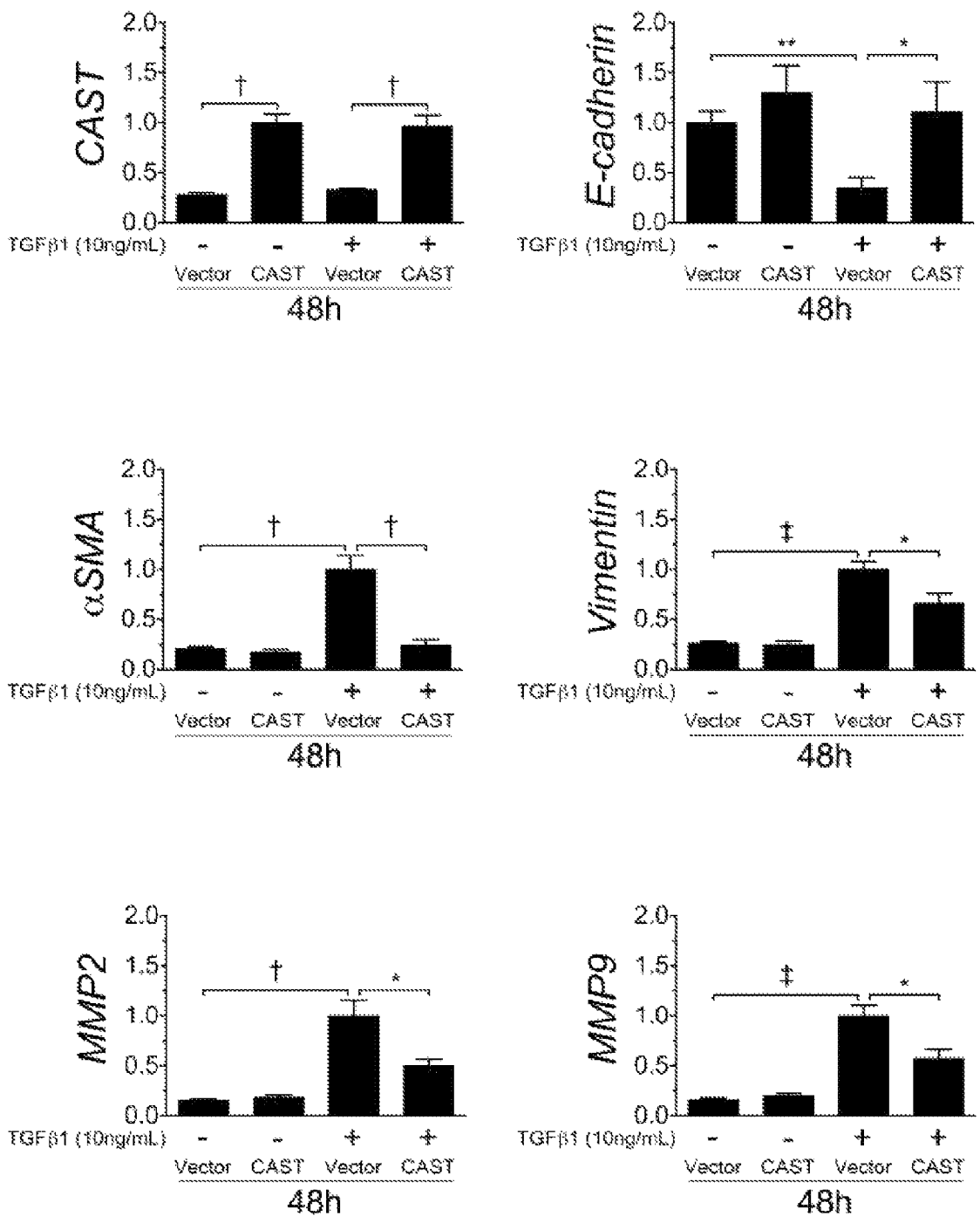
Figure 7D:
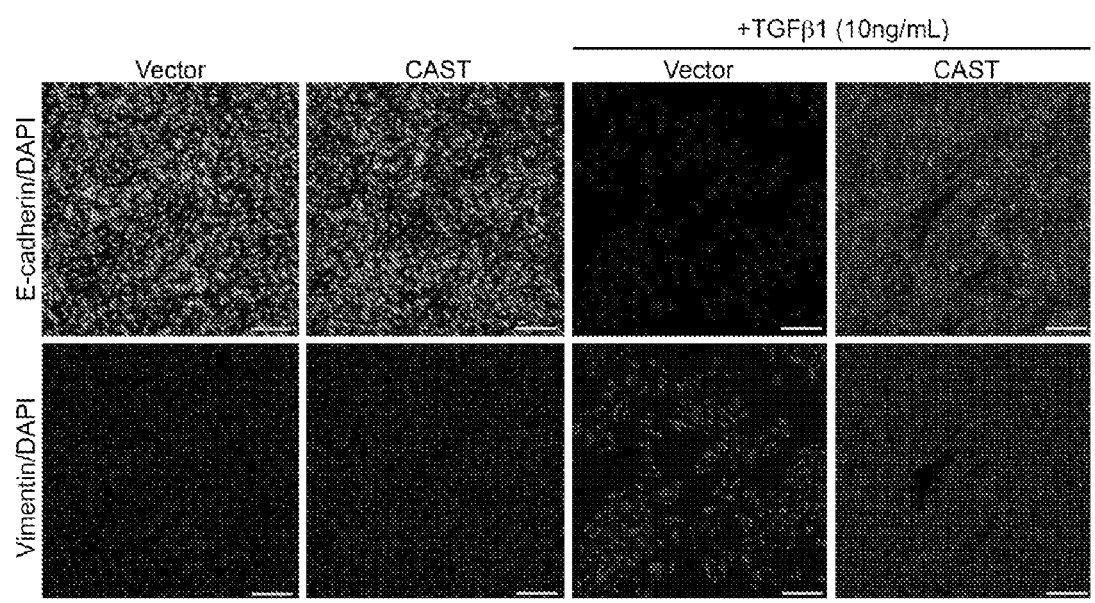
Figure 8A:
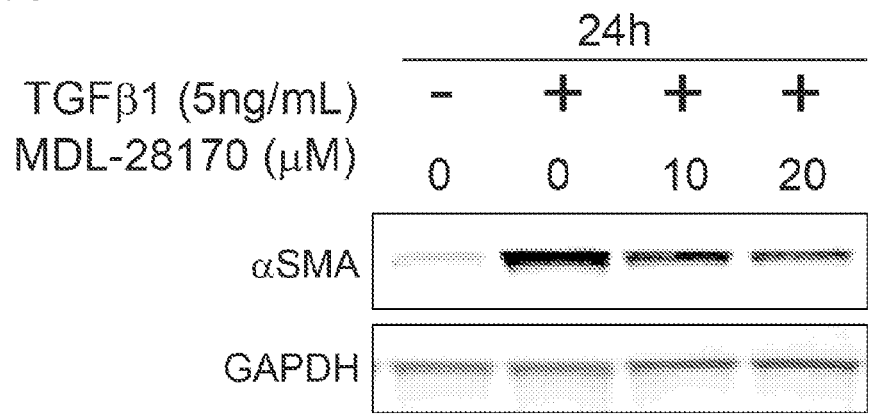
Figure 8B:
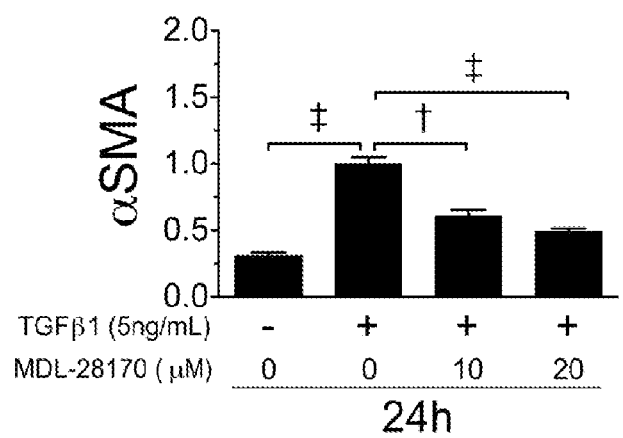
Figure 8C:
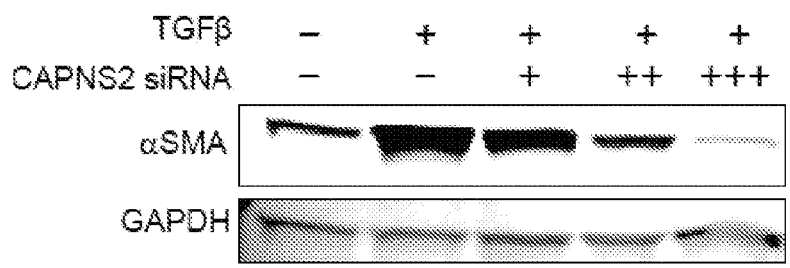
Figure 9A:
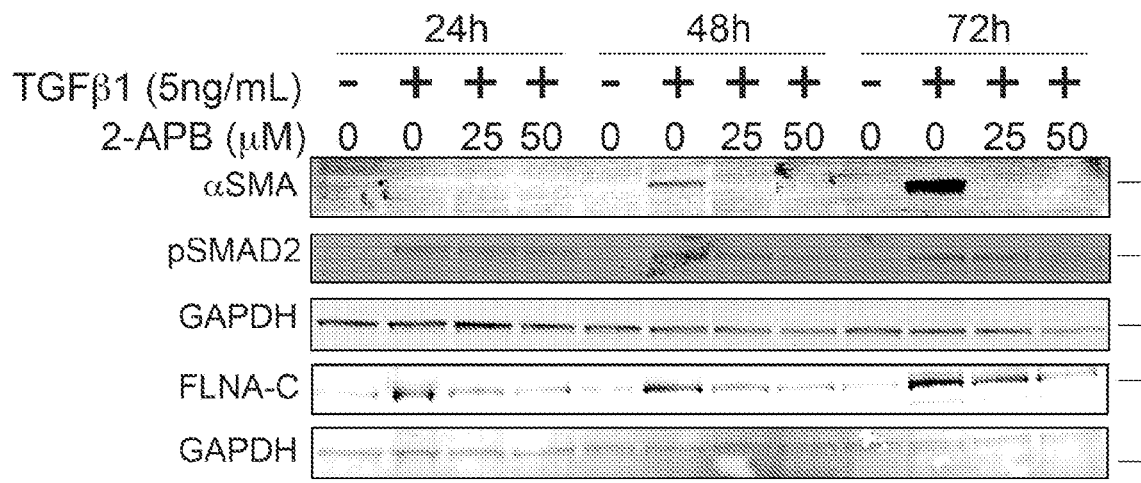
Figure 9B:
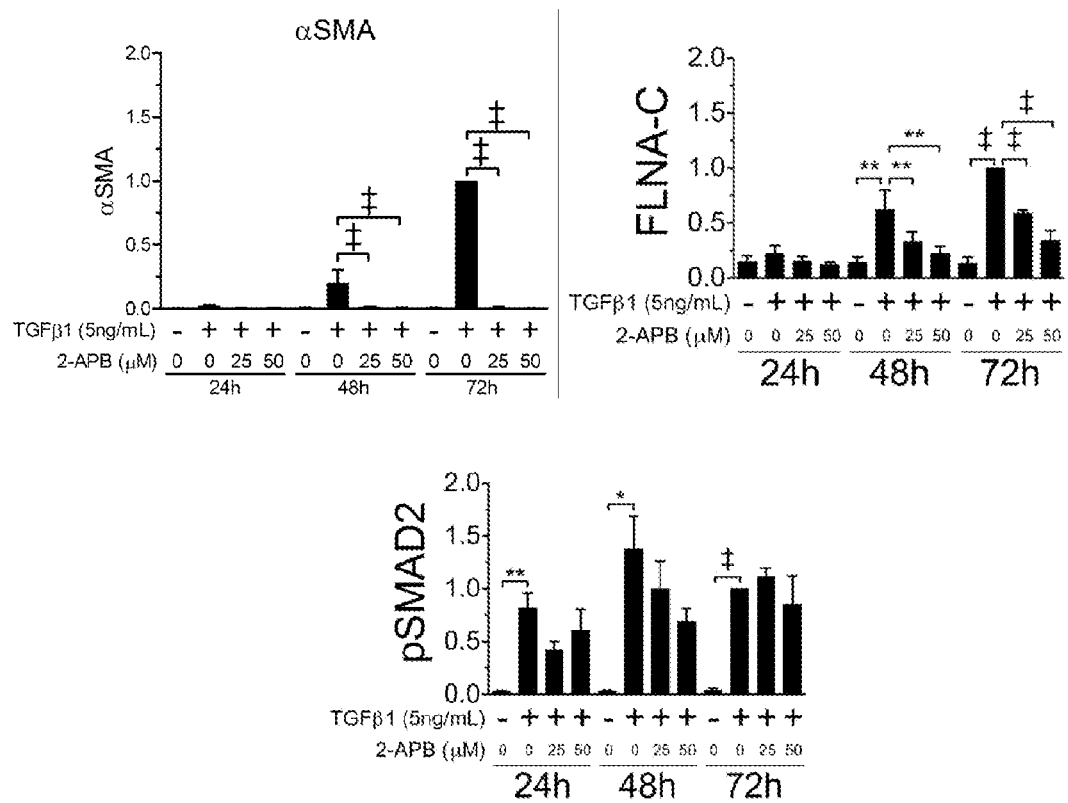
Figure 9C:
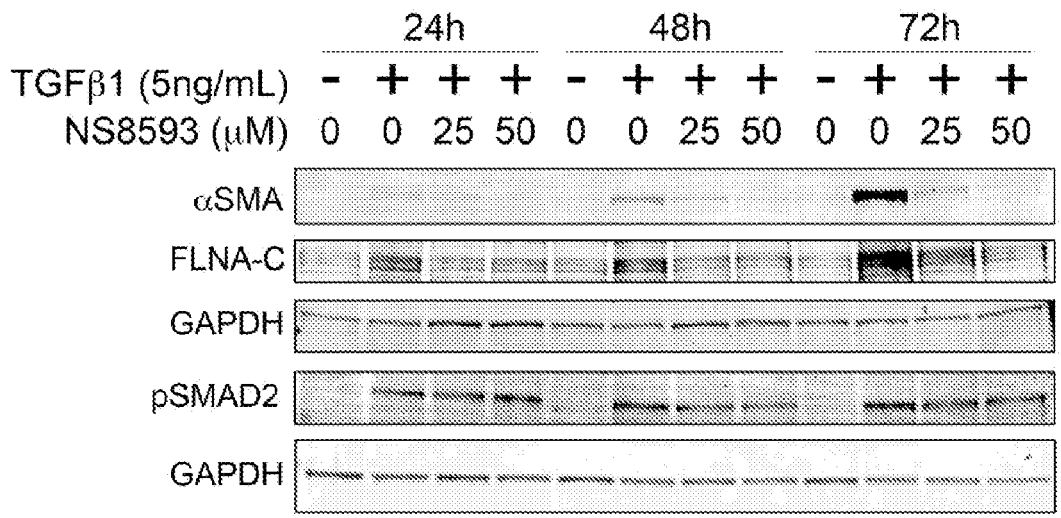
Figure 9D:
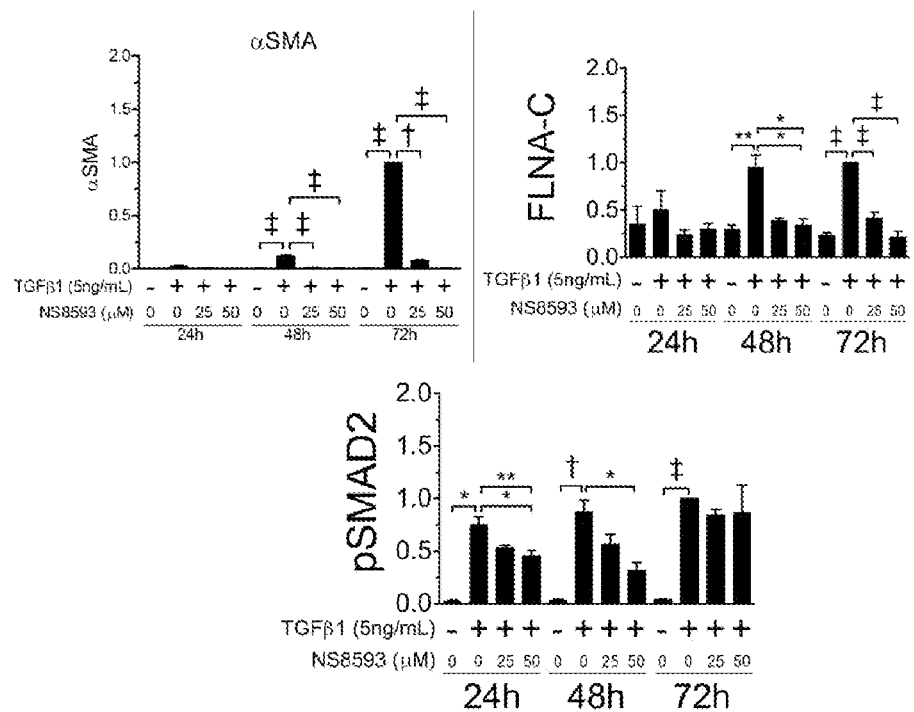
Figure 10A:
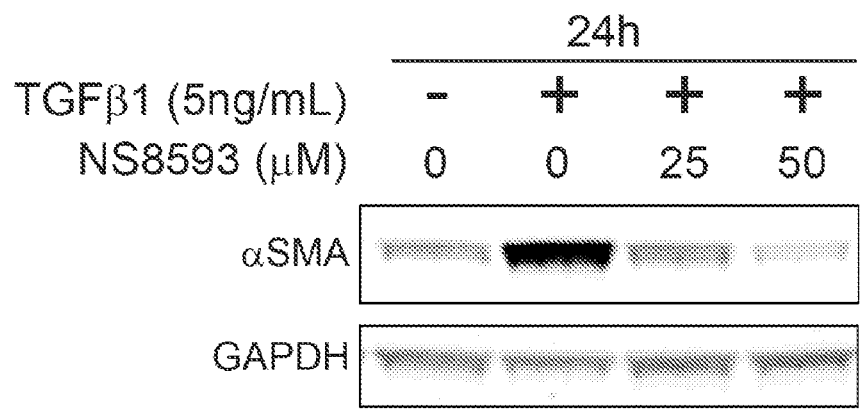
Figure 10B:
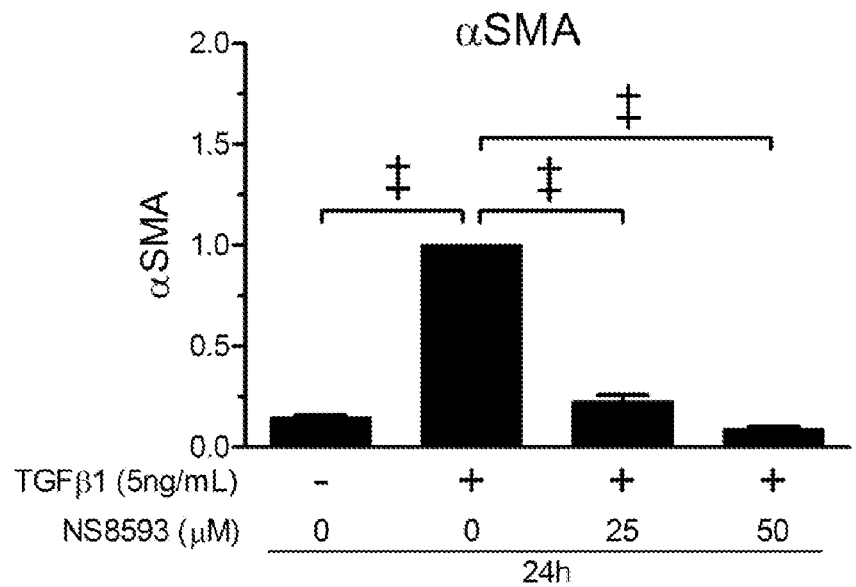
Figure 11A:
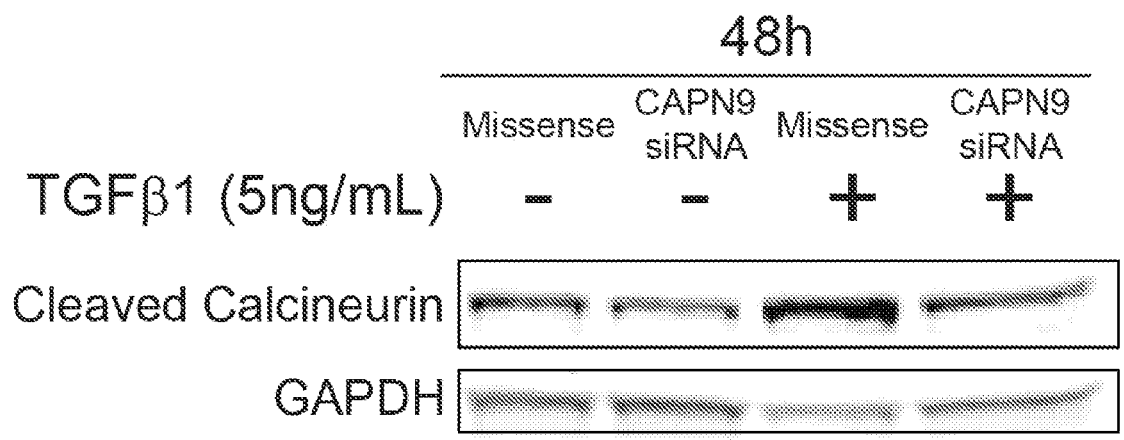
Figure 11B:
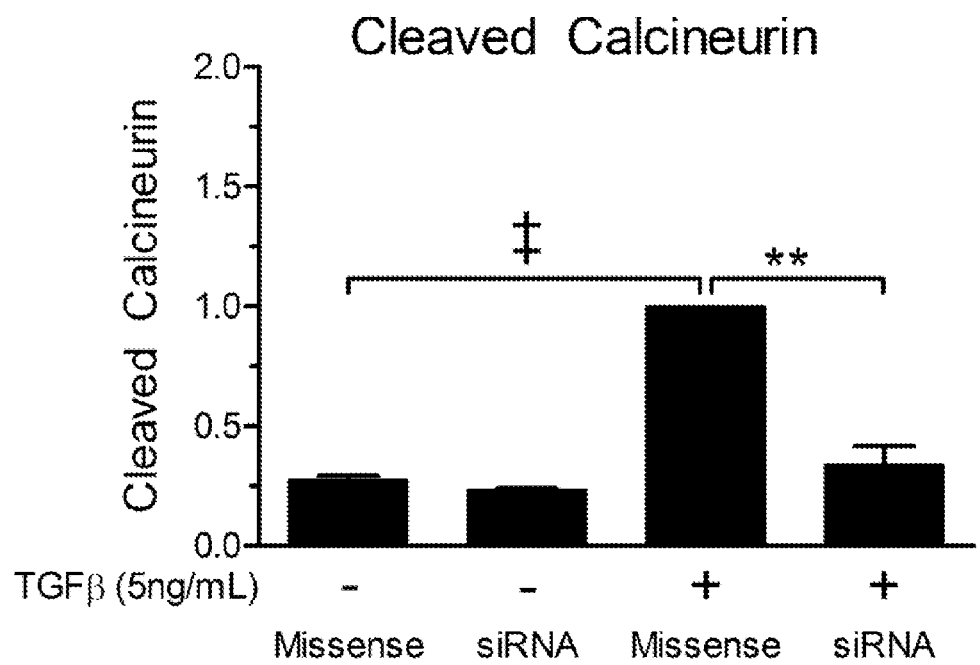
Figure 12:
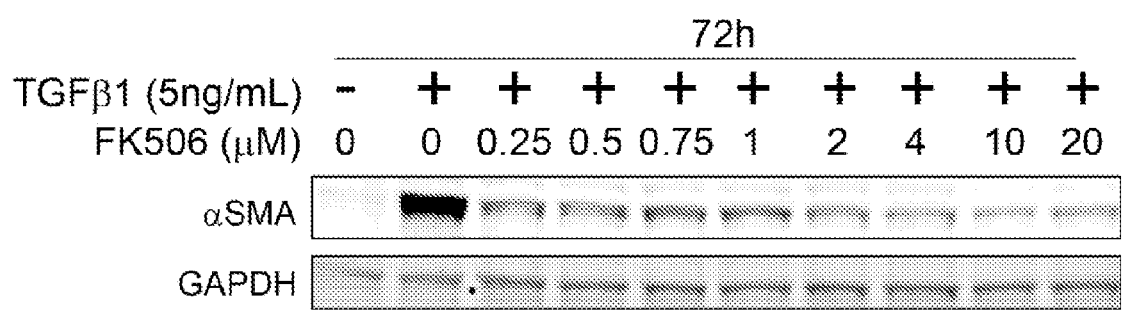
Figure 13A:
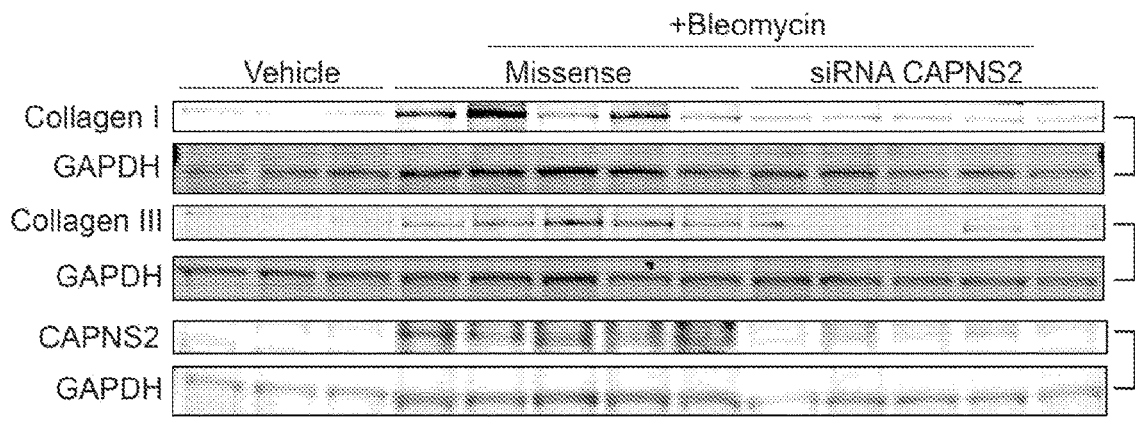
Figure 13B:
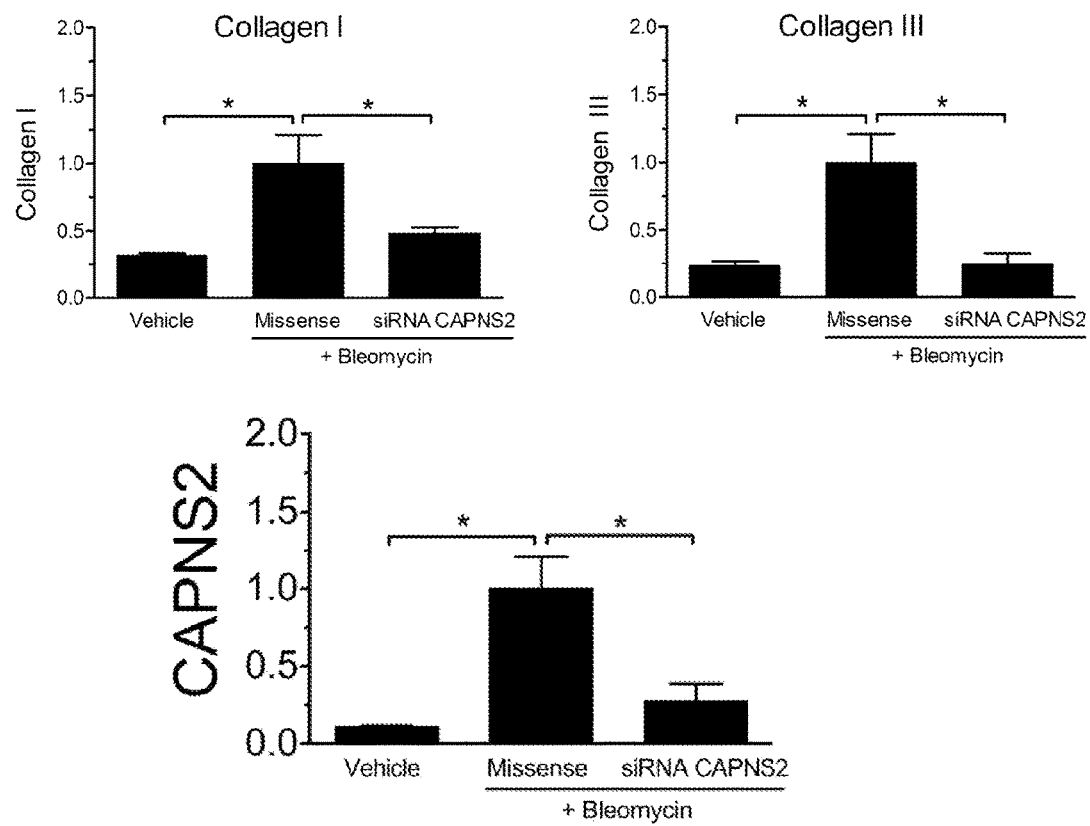
Figure 13C:
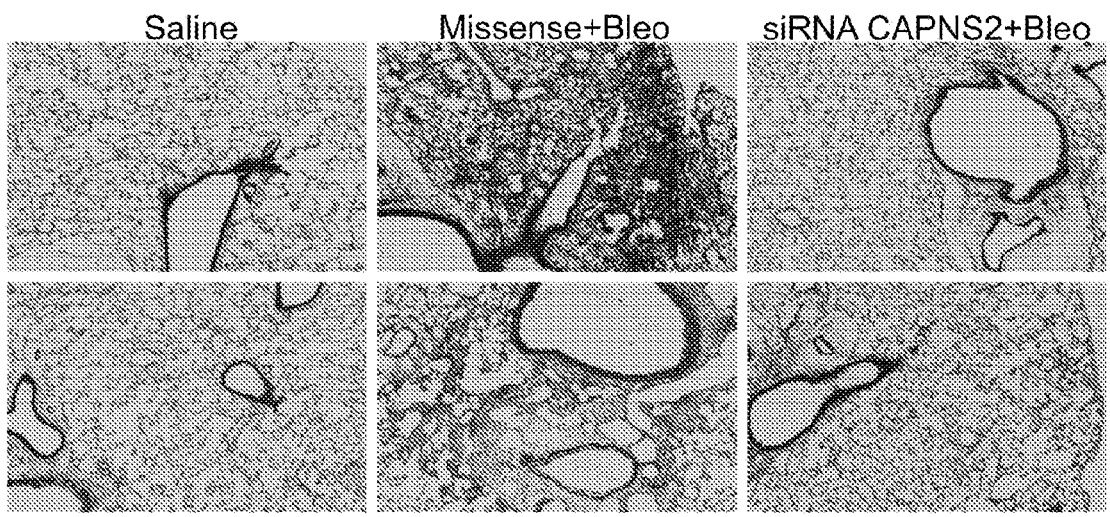
Figure 14A:
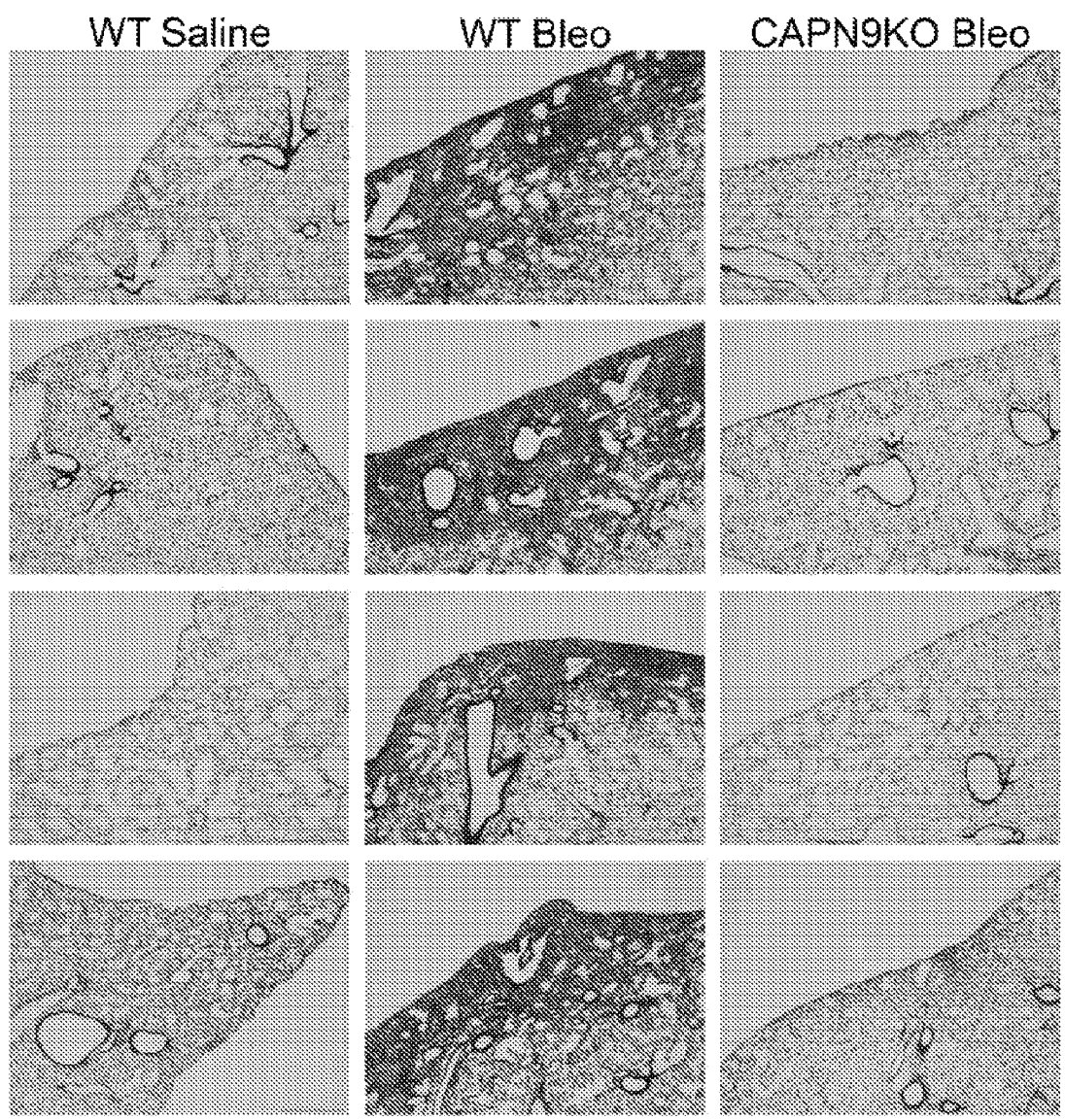
Figure 14B:
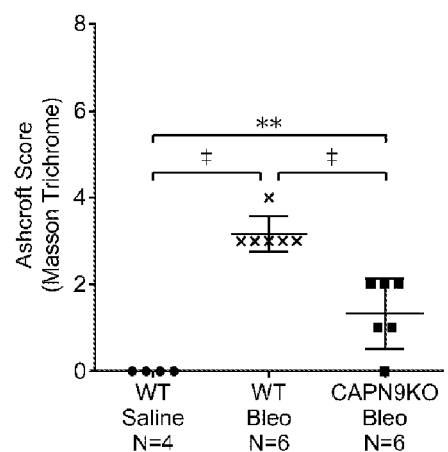
Figure 14C:
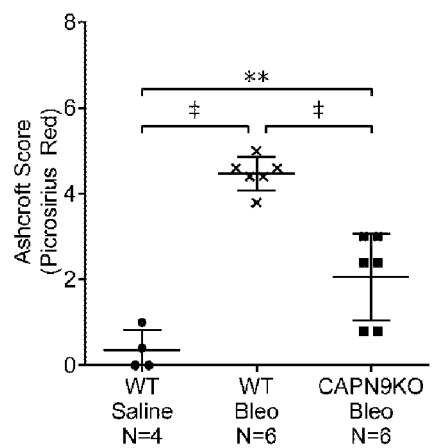
Figure 14D:
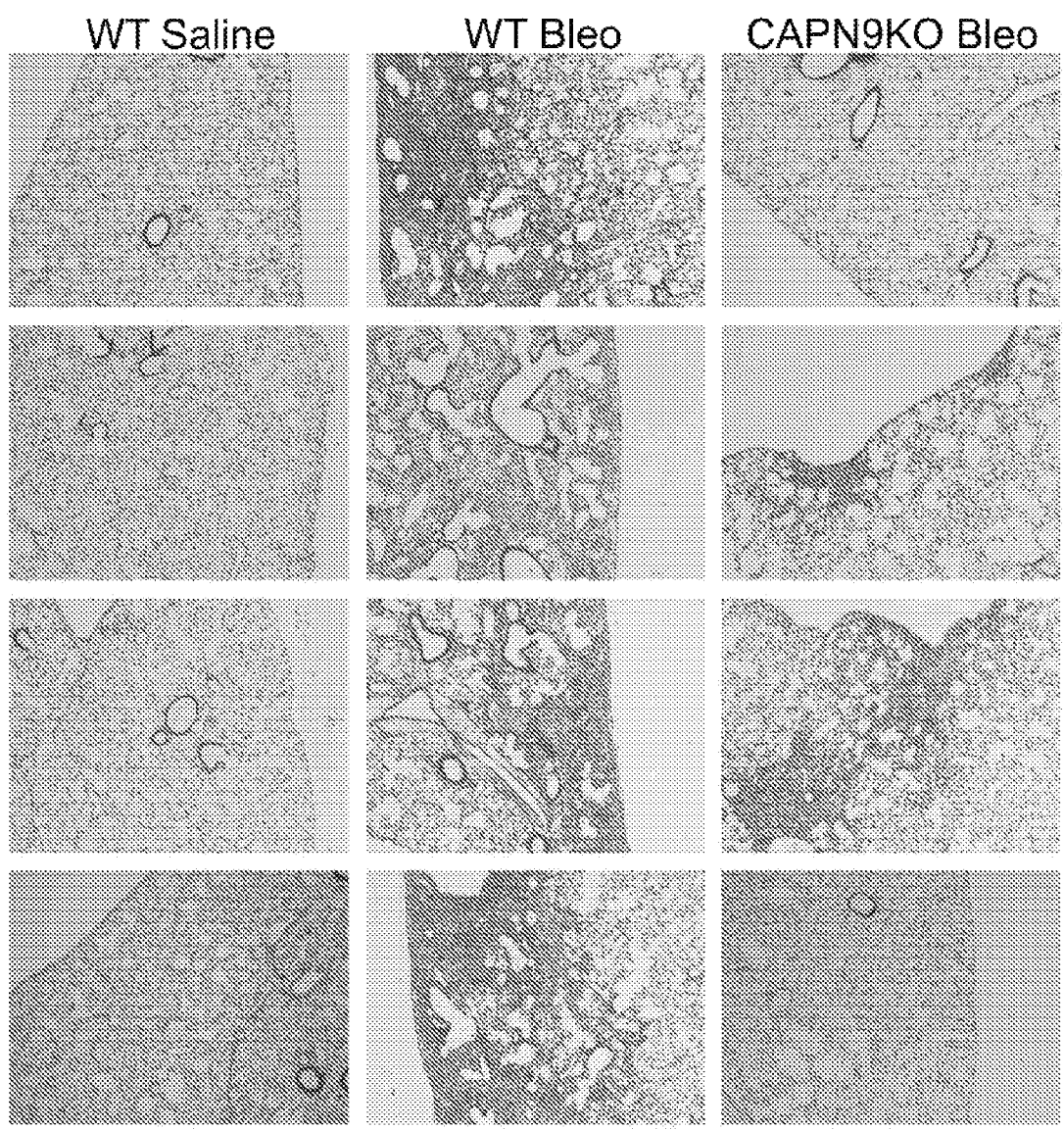
Figure 14E:
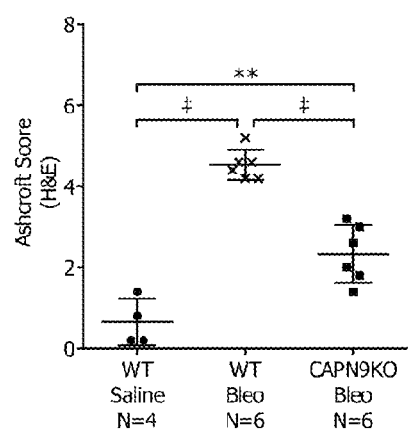
Figure 14F:
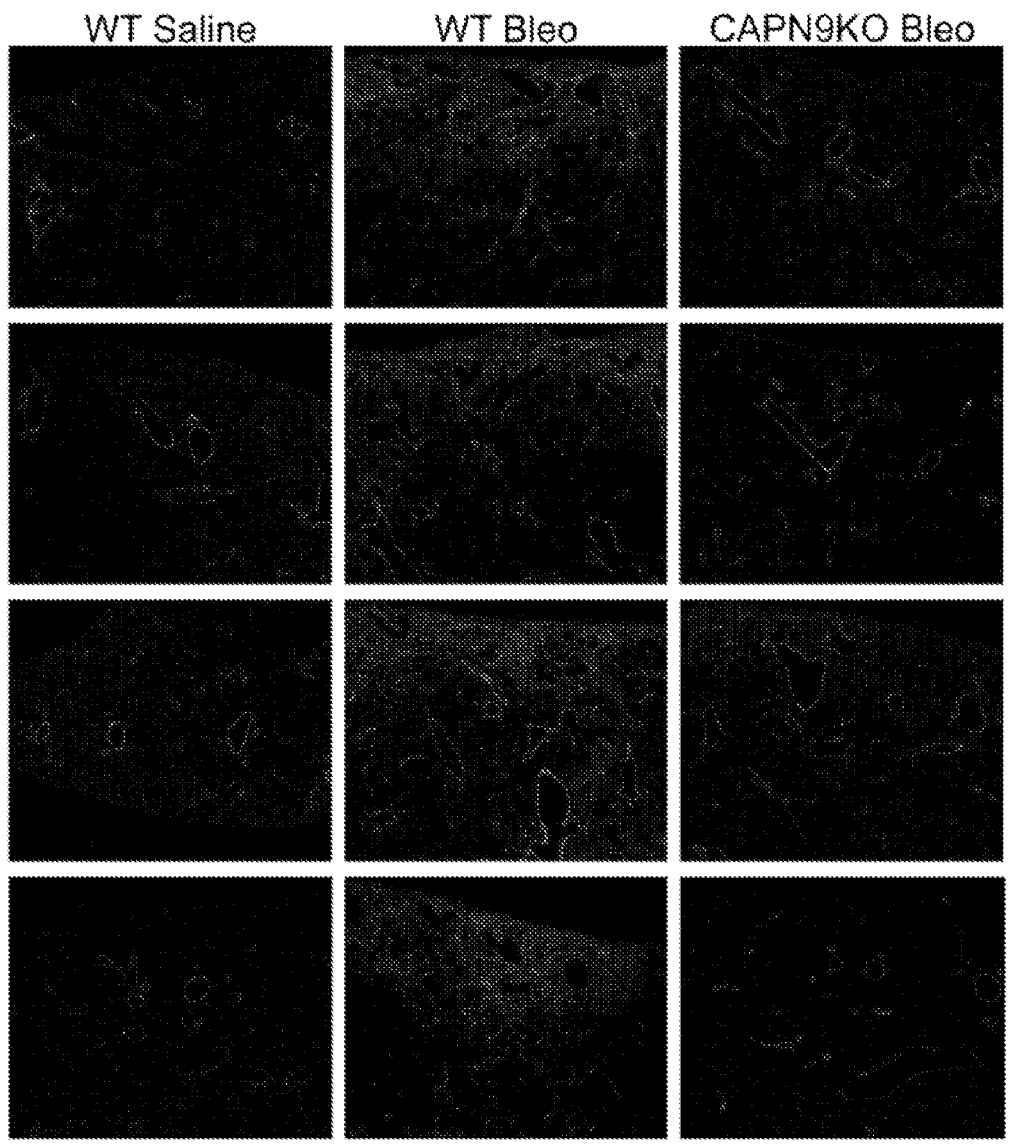
Figure 14F:
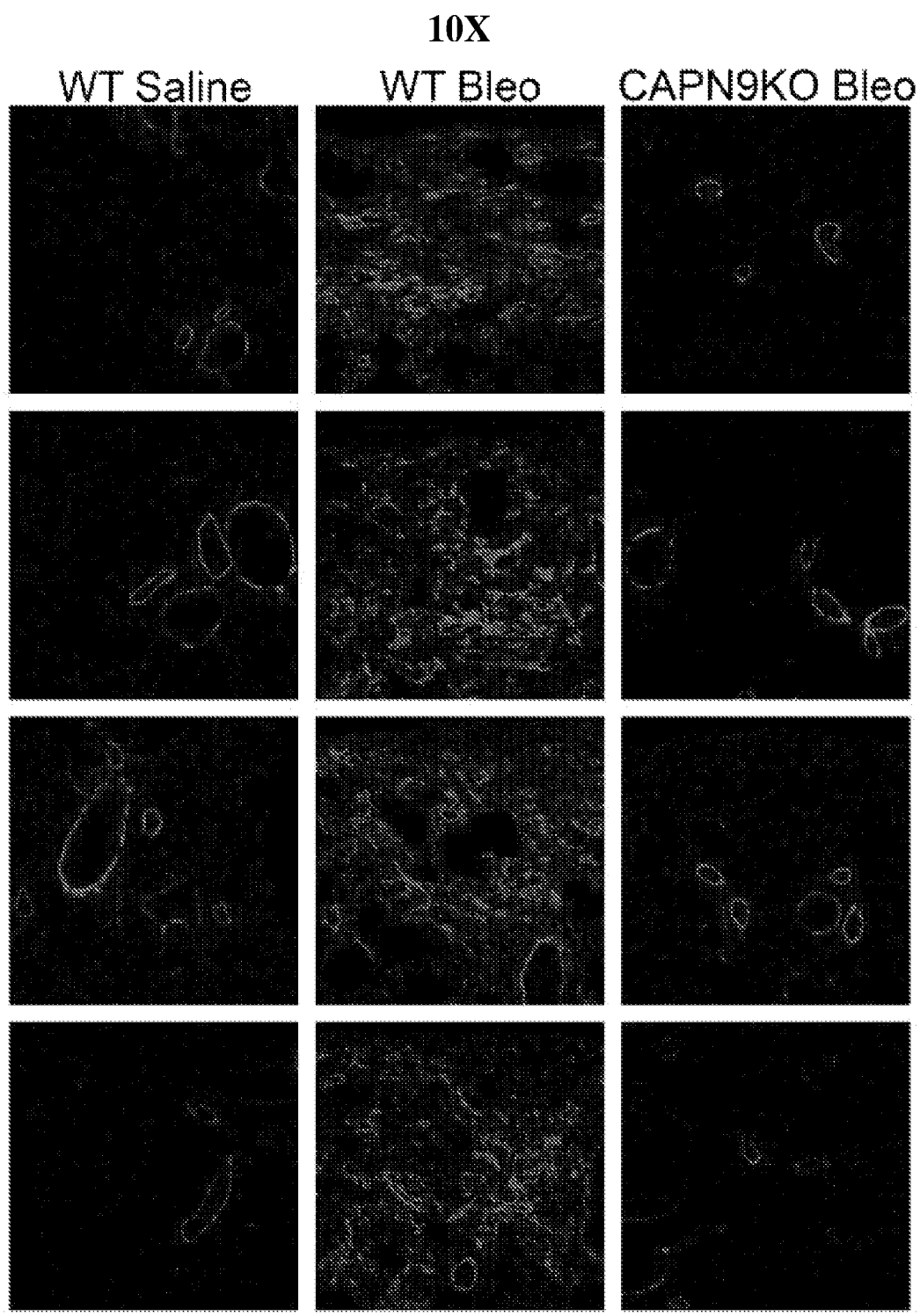
Figure 14F:
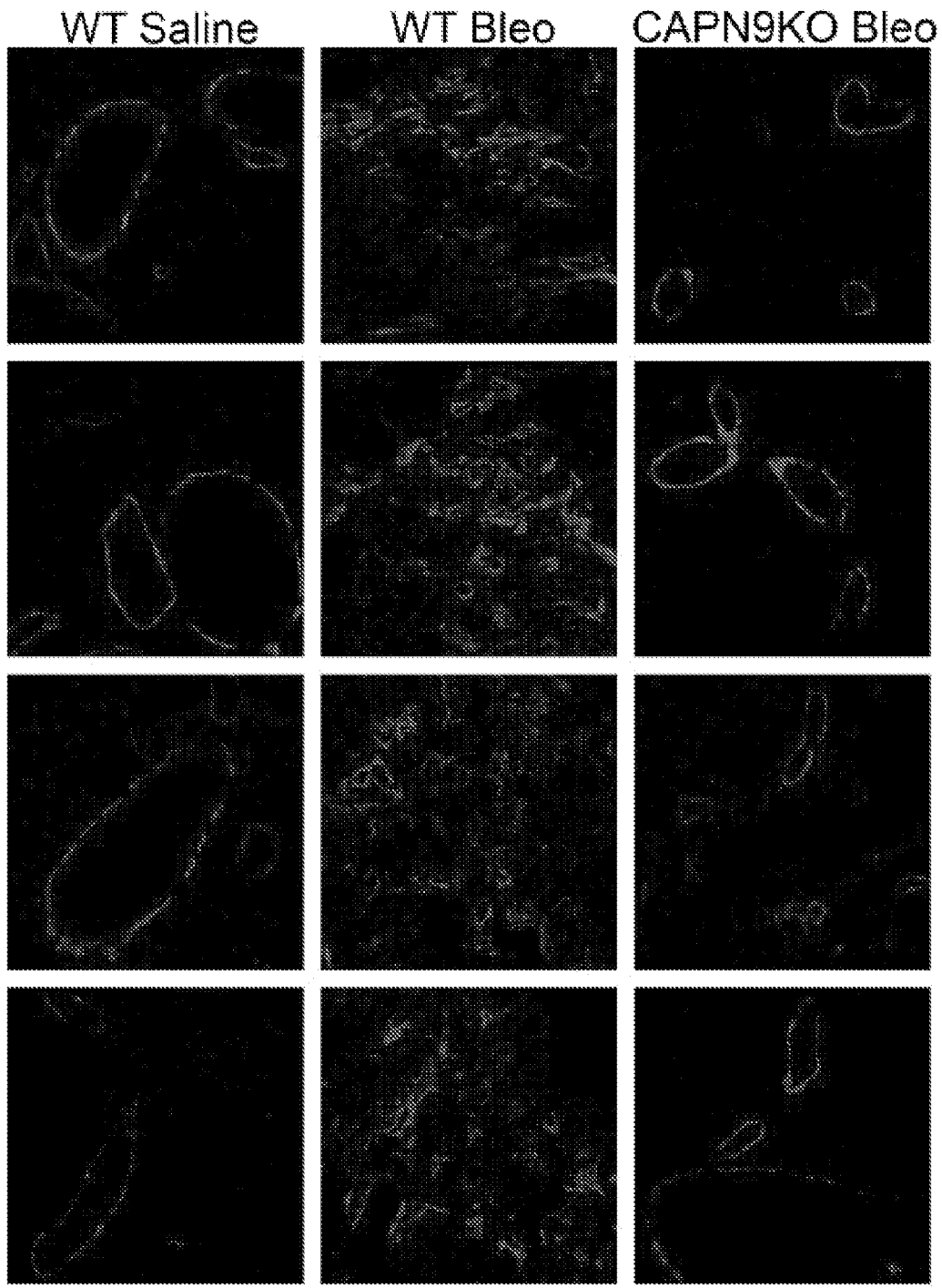
Figure 14G:
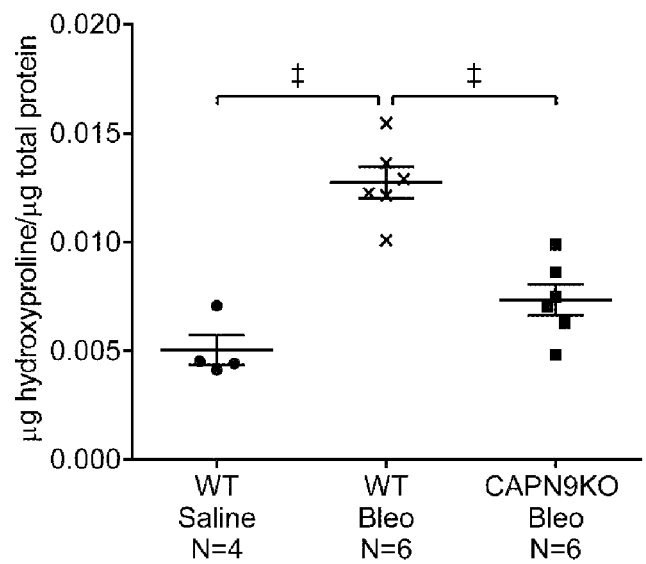
Figure 14H:
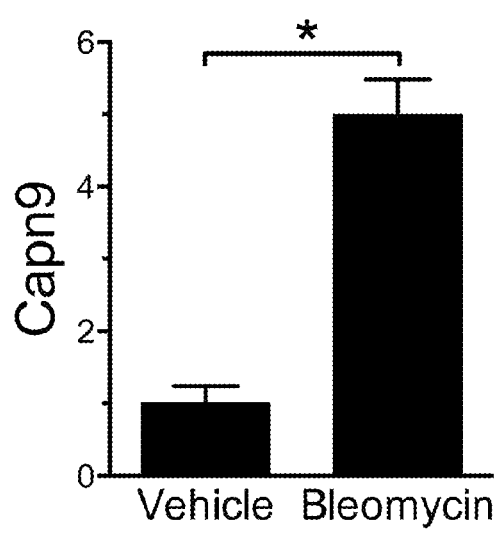
Figure 14I:
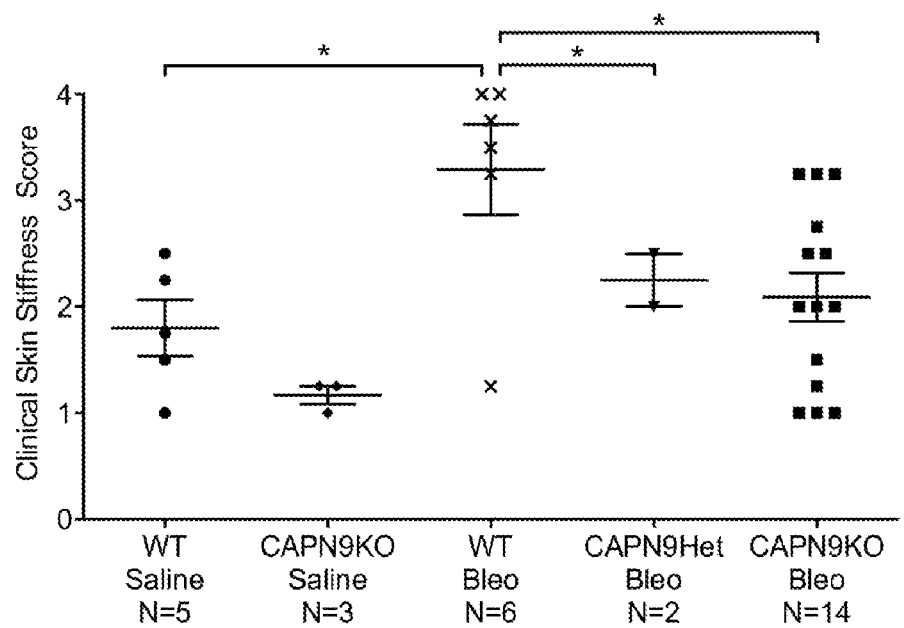
Figure 14J:
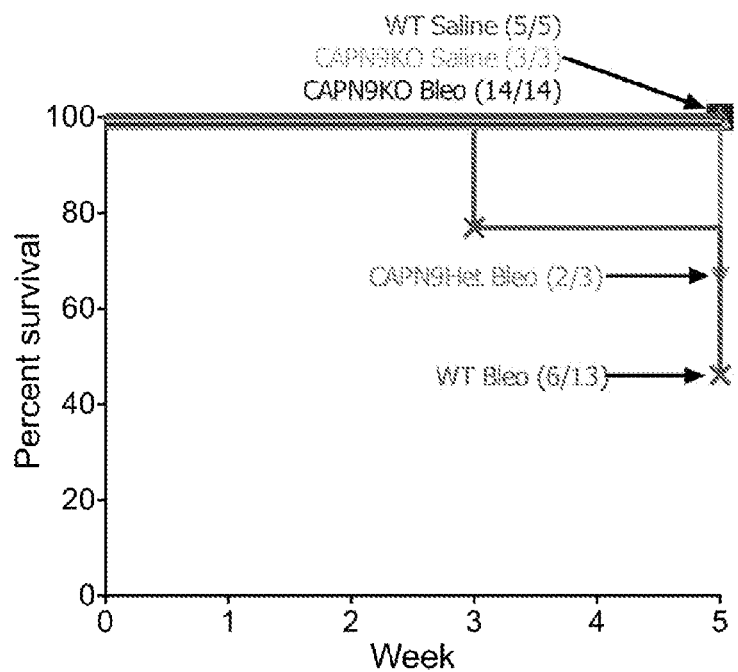

FIG. 3A and FIG. 3B show that overexpression of calpastatin in NMuMG cells was able to block TGFβ-induced EMT in NMuMG cells as measured from αSMA expression by western blot (FIG. 3A) and quantified western blot data of αSMA protein levels done in biological replicates (FIG. 3B; Levels were normalized to the 72 h TGFβ1 with control vector sample for each blot. Student's t-test *p<0.05, **p<0.01, †p<0.005, †† p<0.001). Calpastatin expression was monitored by measuring levels of GFP (AcGFP) expression. FIG. 3A and FIG. 3B. also show that overexpression of calpastatin suppressed TGFβ-induced calpain activity (as measured by cleavage of Filamin A, a known calpain substrate) without affecting TGFβ-induced phosphorylation of SMAD2, as measured by western blot (FIG. 3A) and quantified western blot data protein levels done in biological replicates (FIG. 3B; Levels were normalized to the 72 h TGFβ1 with control vector sample for each blot. Student's t-test *p<0.05, **p<0.01, † p<0.005, †† p<0.001);

FIG. 4A and FIG. 4B show that siRNA-mediated knockdown of tissue-specific CAPN9 (FIG. 4A) or CAPNS2 (FIG. 4B) inhibits TGFβ-induced EMT in NMuMG cells after 48 h as measured from αSMA levels by western blot. Quantified western blot data of tissue specific dimeric calpain isoforms levels and αSMA were done in biological replicates (Levels were normalized to TGFβ1 with missense control samples for each blot. Student's t-test *p<0.05, **p<0.01, †p<0.005, †† p<0.001);

FIG. 5A, FIG. 5B, and FIG. 5C show that siRNA-mediated knockdown of ubiquitously expressed CAPN1 (FIG. 5A), CAPN2 (FIG. 5B), or CAPNS1 (FIG. 5C) failed to suppress TGFβ-induced EMT in NMuMG cells as measured from αSMA protein levels by western blot. Quantified western blot data of ubiquitously expressed dimeric calpain isoforms levels and αSMA were done in biological replicates (Levels were normalized to TGFβ1 with missense control samples for each blot. Student's t-test *p<0.05, **p<0.01, †p<0.005, †† p<0.001);

FIG. 6A shows expression of large calpain subunits (CAPN1, CAPN2, CAPN9) in various mouse organs as measured by quantitative PCR (FIG. 6A; Levels normalized to organ of highest expression for each calpain isoform). FIG. 6B shows expression of small calpain subunits (CAPNS1, CAPNS2) in various mouse organs (FIG. 6B; Levels normalized to organ of highest expression for each isoform);

FIG. 7A shows that siRNA-mediated knockdown of CAPNS2 inhibits TGFβ1-induced EnMT in PAVEC as measured from gene expression of αSMA, vimentin, E-cadherin, MMP2 and MMP9 by quantitative PCR, done in biological replicates (FIG. 7A; Levels were normalized to mean value of the TGFβ1 with control vector sample. Students t-test *p<0.05, **p<0.01, †p<0.005, †† p<0.001). FIG. 7B shows that siRNA-mediated knockdown of CAPNS2 inhibits morphological changes associated with EnMT such as downregulation of E-cadherin/cell-cell adhesion and upregulation of vimentin. (FIG. 7B; E-cadherin shown in green, vimentin shown in red, DAPI nuclear marker shown in blue. Scale bar=100 μm). FIG. 7C shows that overexpression of calpastatin inhibits TGFβ1-induced EnMT in PAVEC as measured from αSMA, vimentin, E-cadherin, MMP2 and MMP9 by quantitative PCR, done in biological replicates (FIG. 7C; Levels were normalized to mean value of the TGFβ1 with missense control sample. Students t-test (*p<0.05, **p<0.01, †p<0.005, †† p<0.001). FIG. 7D shows that overexpression of calpastatin inhibits morphological changes associated with EnMT such as downregulation of E-cadherin/cell-cell adhesion and upregulation of vimentin (FIG. 7D; E-cadherin shown in green, vimentin shown in red, DAPI nuclear marker shown in blue. Scale bar=100 μm);

FIG. 8A and FIG. 8B show that calpain inhibitor MDL-28170 inhibits TGFβ1-induced FMT in NHLF cells as measured by αSMA levels by western blot analysis (FIG. 8A) and quantified western blot data of αSMA in biological replicates (FIG. 8B; Levels were normalized to the TGFβ1 only treated sample for each blot. Student's t-test *p<0.05, **p<0.01, †p<0.005, †† p<0.001). FIG. 8C shows that knockdown of CAPNS2 by siRNA inhibits TGFβ1-induced FMT in NHLF cells as seen by levels of αSMA from western blot analysis;

FIG. 9A and FIG. 9B, show that non-specific TRPM7 inhibitor 2-APB suppresses TGFβ-induced EMT in NMuMG cells as measured from αSMA expression by western blot (FIG. 9A) and quantified western blot data of αSMA in biological replicates (FIG. 9B; Levels were normalized to the 72 h TGFβ1 only treated sample for each blot. Students t-test *p<0.05, **p<0.01, †p<0.005, †† p<0.001); FIG. 9A and FIG. 9B. show that the non-specific TRPM7 inhibitor 2-APB suppresses TGFβ-induced calpain activity (as measured by cleavage of Filamin A, a known calpain substrate) without significantly affecting TGFβ-induced phosphorylation of SMAD2, as measured by western blot (FIG. 9A) and quantified western blot data done in biological replicates (FIG. 9B; Levels were normalized to the 72 h TGFβ1 only treated sample for each blot. Student's t-test *p<0.05, **p<0.01, †p<0.005, †† p<0.001). FIG. 9C, and FIG. 9D show that TRPM7 specific inhibitor NS8593 suppresses TGFβ1-induced EMT in NMuMG cells as measured from αSMA expression by western blot (FIG. 9C) and quantified western blot data of αSMA in biological replicates and analyzed by Students t-test (FIG. 9D; *p<0.05, **p<0.01, †p<0.005, ††p<0.001). FIG. 9C and FIG. 9D. show that the specific TRPM7 inhibitor NS8593 suppresses TGFβ-induced calpain activity (as measured by cleavage of Filamin A, a known calpain substrate) without significantly affecting TGFβ-induced phosphorylation of SMAD2 (at the 72 h timepoint), as measured by western blot (FIG. 9C) and quantified western blot data done in biological replicates (FIG. 9D; Levels were normalized to the 72 h TGFβ1 only treated sample for each blot. Student's t-test *p<0.05, **p<0.01, † p<0.005, †† p<0.001);

FIG. 10A and FIG. 10B show that the TRPM7 specific inhibitor NS8593 suppresses TGFβ1-induced FMT in NHLF cells as measured by αSMA levels from western blot analysis (FIG. 10A) and quantified western blot data of αSMA in biological replicates (FIG. 10B; Levels were normalized to the TGFβ1 only treated sample for each blot. Student's t-test *p<0.05, **p<0.01, † p<0.005, †† p<0.001);

FIG. 11A and FIG. 11B show that knockdown of CAPN9 suppresses TGFβ1-induced cleavage of calcineurin into its constitutively active form at 48 h by western blot analysis (FIG. 11A) and quantified western blot data of constitutively active calcineurin at 48 h in biological replicates (FIG. 11B; Levels were normalized to the TGFβ1 only treated sample for each blot. Student's t-test *p<0.05, **p<0.01, † p<0.005, †† p<0.001);

FIG. 12 shows that calcineurin inhibitor FK506 suppresses TGFβ1-induced αSMA expression in NMuMG cells as seen by αSMA levels from western blot analysis;

FIG. 13A, FIG. 13B, and FIG. 13C show that delivery of CAPNS2 siRNA suppresses bleomycin-induced lung fibrosis in mice. FIG. 13A shows levels of Collagen I/Collagen III/CAPNS2 protein by western blot in lung isolated from mice treated with vehicle or bleomycin and missense/siRNA (FIG. 13A; mice were treated 4 times within a 16-day period and challenged 1 day after the first siRNA dose; all drugs were delivered using an aerosolizing microsprayer syringe in 50 μL of sterile saline solution). Data was quantified from the western blots and grouped by treatment (FIG. 13B; Kruskal-Wallis non-parametric test one-way analysis of variance test used; * p<0.05). FIG. 13C shows masson trichrome stained lung sections that reveal fibrosis in Bleomycin+Missense treated mice but not in Bleomycin+siRNA CAPNS2 treated mice (FIG. 13C; blue staining indicates collagen);

FIG. 14A, FIG. 14B, FIG. 14C, FIG. 14D, FIG. 14E, FIG. 14F, FIG. 14G, FIG. 14H, FIG. 14I, and FIG. 14J, show that CAPN9 deficient mice are immune to systemically-delivered bleomycin-induced fibrosis. FIG. 14A shows that CAPN9 deficient mice treated with bleomycin had significantly less lung fibrosis compared to WT mice treated with bleomycin, as assessed by masson trichrome staining and histological grading by Ashcroft scores (FIG. 14B; Student's t-test *p<0.05, **p<0.01, † p<0.005, †† p<0.001). FIG. 14C shows that CAPN9 deficient mice treated with bleomycin had significantly less lung fibrosis compared to WT mice treated with bleomycin, as assessed by histological grading from picrosirius red stained sections using Ashcroft scores (FIG. 14C; Student's t-test *p<0.05, **p<0.01, † p<0.005, †† p<0.001). FIG. 14D shows that CAPN9 deficient mice treated with bleomycin had significantly less infiltrating cells compared to WT mice treated with bleomycin, as assessed by hematoxylin and eosin (H&E) staining and histological grading by Ashcroft scores (FIG. 14E; Student's t-test *p<0.05, **p<0.01, † p<0.005, †† p<0.001). FIG. 14F shows that CAPN9 deficient mice treated with bleomycin did not develop an accumulation and/or proliferation of αSMA-positive pro-fibrotic myofibroblasts, compared to WT mice, as assessed by immunofluorescent staining of lung sections for αSMA (FIG. 14F; Tiled 10×, 10× and 20× magnifications. αSMA shown in red, nuclear marker DAPI shown in blue). FIG. 14G shows that CAPN9 deficient mice treated with bleomycin had significantly less lung collagen content compared to WT mice treated with bleomycin, as assessed by hydroxyproline assay (FIG. 14G; Student's t-test $*p<0.05$, $**p<0.01$, $\dagger p<0.005$, $\dagger\dagger p<0.001$). FIG. 14H shows WT mice treated with bleomycin had induced high levels of CAPN9 gene expression compared to WT mice treated with saline. FIG. 14I shows CAPN9 deficient mice treated with systemic bleomycin had reduced dermal fibrosis, as determined by clinical skin stiffness assessment (FIG. 14I; Scale of 1-4 with 4 being most severe. Scores from 4 independent testers was averaged for each animal. Student's t-test $*p<0.05$, $**p<0.01$, $\dagger p<0.005$, $\dagger\dagger p<0.001$). FIG. 14J is a Kaplan-Meier plot of survival over time and shows CAPN9 deficient mice treated with bleomycin had improved survival compared to WT mice treated with bleomycin.

Figure 15A:
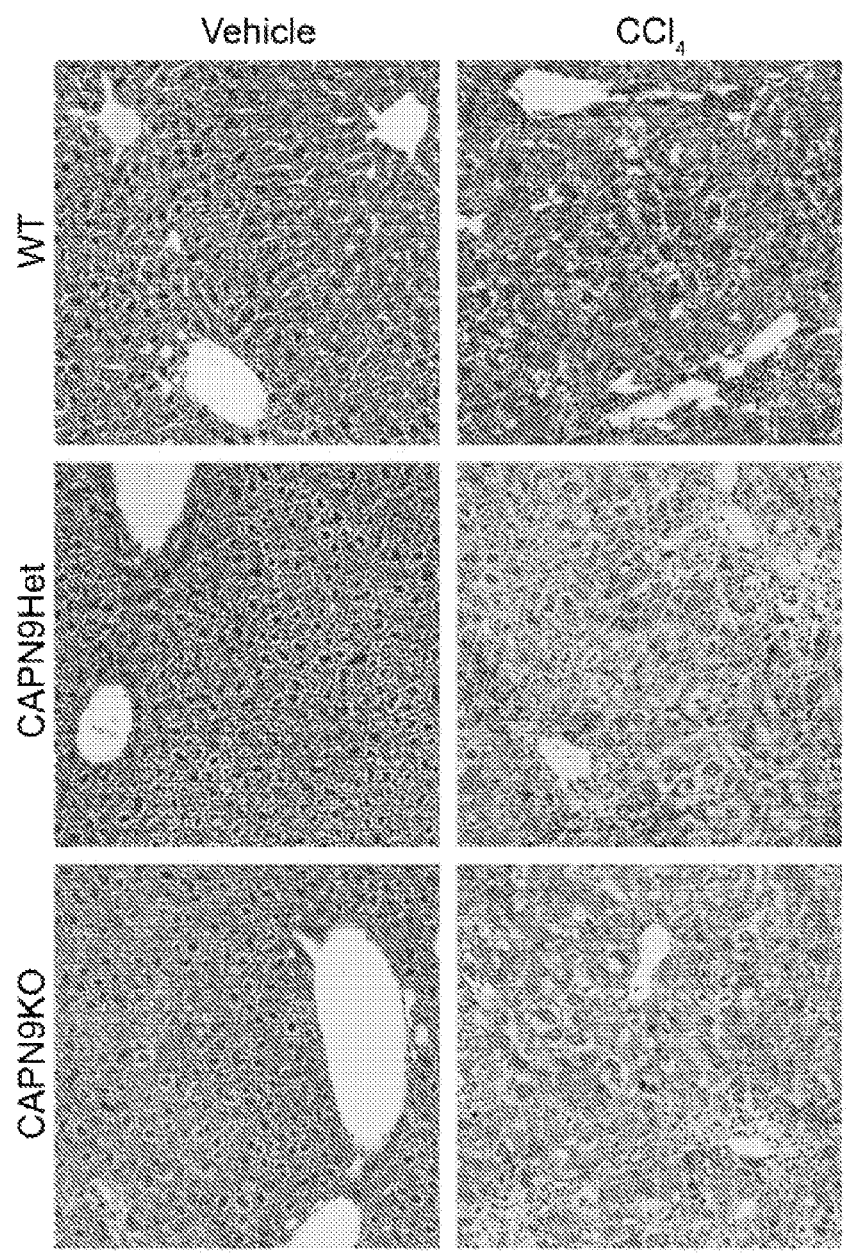
Figure 15B:
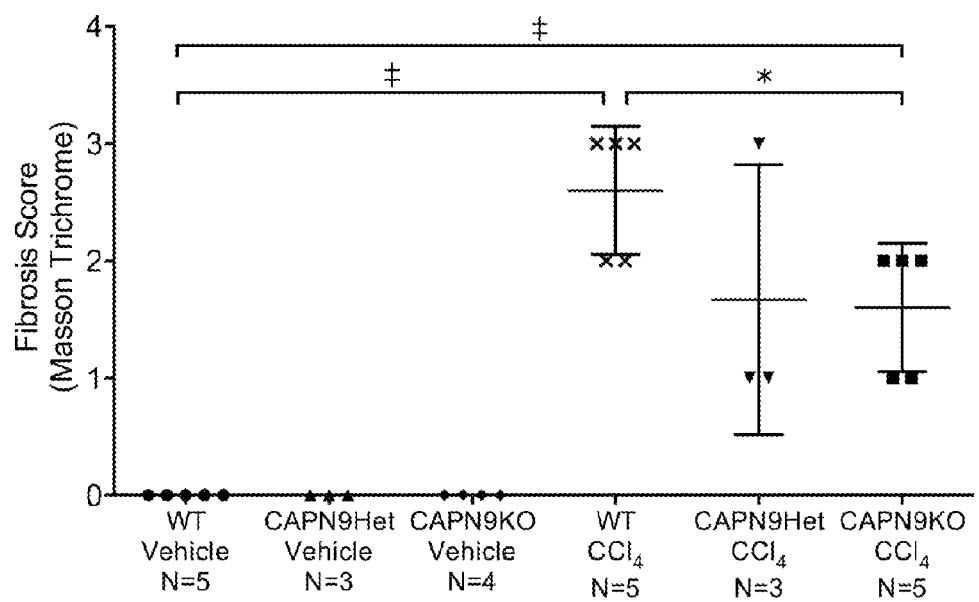
Figure 15C:
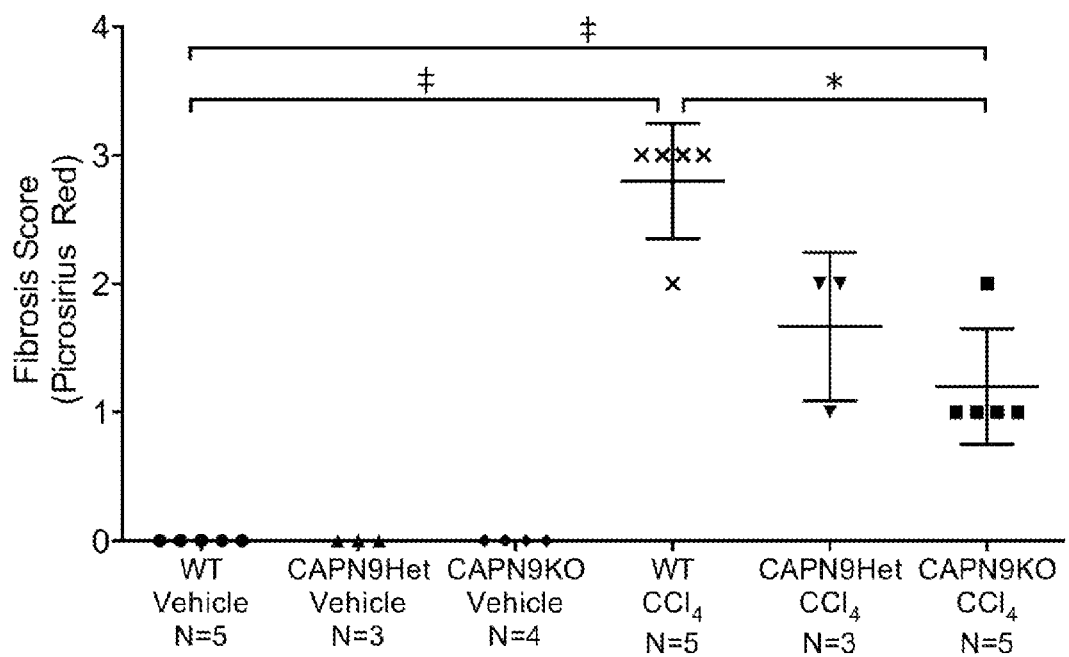

FIG. 15A, FIG. 15B, and FIG. 15C show that CAPN9 deficient mice are resistant to carbon tetrachloride-induced liver fibrosis. FIG. 15A shows that CAPN9 deficient mice treated with carbon tetrachloride had significantly less liver fibrosis compared to WT mice treated with bleomycin, as assessed by masson trichrome staining and histological grading by fibrosis scores (FIG. 15B; Student's t-test $*p<0.05$, $**p<0.01$, $\dagger p<0.005$, $\dagger\dagger p<0.001$). FIG. 15C shows that CAPN9 deficient mice treated with bleomycin had significantly less liver fibrosis compared to WT mice treated with bleomycin, as assessed by histological grading of picrosirius red staining by fibrosis scores (FIG. 15C; Student's t-test $*p<0.05$, $**p<0.01$, $\dagger p<0.005$, $\dagger\dagger p<0.001$).

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Current therapies for organ fibrosis are palliative at best and not curative in nature, despite the great need, and thus rely on unsustainable high-risk organ transplants. Perhaps equal or greater in need are patients afflicted with potentially metastatic cancers. Although numerous attempts have been made to intensely study TGFβ inhibitors as a therapy, the side effects have overshadowed much of the potential benefits.

The presently disclosed subject matter relates to the discovery of a non-essential enzyme activity that is necessary for TGFβ-induced mesenchymal transition, a known essential contributor to disease states associated with fibrosis or metastasis in cancers of epithelial origin. This process is specifically attributable to and dependent upon the dimeric calpain CAPN9 and/or small subunit 2 (CAPNS2). As described more fully in the Examples below, use of either broad-spectrum calpain inhibitors or specific siRNA-mediated silencing of CAPN9 or CAPNS2 was sufficient to block TGFβ-mediated myofibroblast differentiation (such as, for example, epithelial- or endothelial-to-mesenchymal transition (EpMT or EnMT, respectively;) and Fibroblast-to-Myofibroblast transition (FMT)) in culture systems. Both of these calpain subunits show limited postnatal expression and mice are tolerant of the complete null state for CAPN9. Accordingly, the presently disclosed subject matter provides the targeting of CAPN9/CAPNS2 activity as a strategy towards the treatment of diseases associated with myofibroblast differentiation (such as, EpMT or EnMT-associated diseases) and addresses a major need for severely afflicted patients with currently limited options.

Enzymatic proteases, such as calpains, are ideal drug targets because small molecule inhibitors can be created through rational drug design or identified by drug screens of FDA approved compounds more easily than other molecules. Enzymatic inhibition of calpains can have a potent effect per dose of drug compared to other non-enzymatic targets due to their catalytic nature. Calpains are also cytosolic, with much of their activity being located under the plasma membrane where calcium concentration can be high, thus making calpains a more bioavailable drug target.

I. General Techniques

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), Current Protocols in Molecular Biology, Current Protocols in Immunology, Current Protocols in Protein Science, and Current Protocols in Cell Biology, all John Wiley & Sons, N.Y., edition as of December 2008; Sambrook, Russell, and Sambrook, Molecular Cloning: A Laboratory Manual, 3rd ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; 10th ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, World Wide Web URL: http://www.ncbi.nlm.nih.gov/omim/ and in Online Mendelian Inheritance in Animals (OMIA), a database of genes, inherited disorders and traits in animal species (other than human and mouse), at http://omia.angis.org.au/contact.shtml.

II. Definitions

As used herein, the phrase "myofibroblast differentiation" refers to the transformation of normally functioning cells into fibrosis promoting cells termed "myofibroblasts." This transformative process is inclusive of the processes of Epithelial-to-Mesenchymal Transition (EpMT), Endothelial-to-Mesenchymal Transition (EnMT) as well as Fibroblast-to-Myofibroblast Transition (FMT). Similarly, the phrase "disease associated with myofibroblast differentiation," as well as variations thereof, refers to any pathology resulting from abnormal production function and maintenance of myofibroblasts, whether as a result of EpMT, EnMT, and/or FMT. In some embodiments, a disease associated with myofibroblast differentiation is a fibrotic disease. In other embodiments, a disease associated with myofibroblast differentiation is a cancer, such as a cancer of epithelial origin.

As used herein, the phrase "an agent capable of modulating the activity of CAPN9 and/or CAPNS2" refers to any agent (including, without limitation, small molecule chemical compounds, non-antibody polypeptides, inhibitory nucleic acids, or antibodies), capable of altering the cellular expression levels and/or biological activity of the CAPN9 and/or CAPNS2 gene, messenger RNA, or protein. In some embodiments, the agent inhibits the biological activity or expression levels of CAPN9, CAPNS2, and/or TRPM7 in vivo and/or in vitro. Reference to modulation of the activity of CAPN9 and/or CAPNS2 can refer to any or more of modulating the activity of CAPN9, or CAPNS2, or a CAPN9/CAPNS2 heterodimer, or an interaction between CAPN9 and CAPNS2. Similarly, references to calpain inhibition can include inhibiting CAPN9, or CAPNS2, or the CAPN9/CAPNS2 heterodimer, or the interaction between CAPN9 and CAPNS2.

In some embodiments, an agent or substance is said to be "specific" if the agent which modulates the biological activity of CAPN9 and/or CAPNS2 directly interferes with the expression (such as transcription, splicing, transport, etc.) of the gene encoding the CAPN9 and/or CAPNS2 mRNA. In other embodiments, an agent or substance is said to be "specific" if the agent which modulates the activity of CAPN9 and/or CAPNS2 directly interferes with the biological activity or production of the CAPN9 and/or CAPNS2 proteins (such as though inhibition of translation, post-translational modifications, intracellular transport, disruption of interactions between one or more proteins, etc.).

In yet other embodiments, an agent or substance is said to be "non-specific" if the agent capable of modulating the activity of CAPN9 and/or CAPNS2 does not directly affect the expression level or activity of CAPN9 and/or CAPNS2 but, instead, alters the activity or expression levels of a protein whose function directly impacts the expression or activity of CAPN9 and/or CAPNS2 (such as, for example, TRPM7 or calpastatin).

An agent or substance is said to "selectively bind" if it reacts or associates more frequently, more rapidly, with greater duration and/or with greater affinity with a particular substance (for example, a protein, such as CAPN9, CAPNS2, or TRPM7 as well as a nucleic acid encoding the same) than it does with alternative substances. In some embodiments, the agent or compound is selective for a particular substance by any of about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% (inclusive of values falling in between these percentages) when compared to an alternative substance. For instance, an antibody "selectively binds" to a target protein (such as CAPN9, CAPNS2, or TRPM7) if it binds with greater affinity, avidity, more readily, and/or with greater duration than it binds to other substances. In some embodiments, the agent or compound selectively binds to a particular substance by any of about %, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% (inclusive of values falling in between these percentages) when compared to an alternative substance.

"Polypeptides" or "proteins" include polypeptides, proteins, peptides, fragments of polypeptides, fusion polypeptides and variants thereof.

The term "contacting," as used herein, includes both directly contacting cells, for example, in vivo, in vitro, or ex vivo, or indirectly contacting cells, such as, for example, by administering an agent to a subject. Further, "contacting" a cell with an agent includes administering or applying a prodrug version of the agent. In some embodiments, the cell is in a fibrotic tissue, a cancerous tissue, and/or tissue with high TGFβ signaling.

As used herein, the term "fibrosis" refers to excessive extracellular matrix protein synthesis and deposition that results in the accumulation of scar tissue. Similarly, as used herein, the term "fibrotic tissue" refers to tissue that has high levels of extracellular matrix proteins (i.e. collagen), undergone extensive remodeling (though activity of matrix metalloproteinases) and exhibits progressively diminished physiological function, due to the activity of cells that have undergone myofibroblast differentiation (such as, EpMT, EnMT, and/or FMT). In some embodiments, the cell is in a cancerous tissue, such as in tissue that comprises at least one cancer cell. In some embodiments, the cell is in a tissue with high TGFβ signaling.

As used herein, the phrase "high TGFβ signaling" is TGFβ signaling that is at a level above TGFβ signaling in normal tissue such that it can promote the transformation of normally functioning cells into fibrosis promoting cells.

A "calcineurin inhibitor" is preferably an immunophilin-binding compound having calcineurin inhibitory activity Immunophilin-binding calcineurin inhibitors are compounds forming calcineurin inhibiting complexes with immunophilins, e.g. cyclophilin and macrophilin Examples of cyclophilin-binding calcineurin inhibitors are cyclosporines or cyclosporine derivatives and examples of macrophilin-binding calcineurin inhibitors are ascomycin (FR 520) and ascomycin derivatives. A wide range of ascomycin derivatives are known, which are either naturally occurring among fungal species or are obtainable by manipulation of fermentation procedures or by chemical derivatization. Ascomycin-type macrolides include ascomycin, tacrolimus (FK506), sirolimus and pimecrolimus.

As used herein, the term "inhibit", "decrease" and grammatical derivations thereof, refers to the ability of an agent to block, partially block, interfere, reduce or deactivate a pathway or mechanism of action. Thus, one of ordinary skill in the art would appreciate that the term "inhibit" or "decrease" encompasses a complete and/or partial loss of activity, e.g., a loss in activity by at least 10%, in some embodiments, a loss in activity by at least 20%, 30%, 50%, 75%, 95%, 98%, and up to and including 100%.

As used herein, "inhibition of target gene expression" includes any decrease in expression or protein activity or expression level of a target gene or protein (such as a CAPN9 or CAPNS2 gene or protein) encoded by the target gene. The decrease may be of at least 10%, 20%, 30%, 40%, 50%, 60%, 70%, 80%, 90%, 95% or 99% or more as compared to the expression of a target gene or the activity or level of the protein encoded by a target gene which has not been inhibited (such as, for example, a gene targeted by an RNA interfering agent). In some embodiments, inhibition of a target gene expression refers to disruption or inhibition of the target gene mRNA (such as, but not limited to, prevention of target gene transcription, splicing, or transport from the nucleus). In other embodiments, inhibition of target gene expression refers to disruption or inhibition of the target gene protein (such as, but not limited to, prevention of translation, post-translational modification, disruption of protein-protein interaction, or depletion of a co-factor (for example, calcium).

As used herein, "calcium influx" or "calcium channel influx" means the movement of calcium ions from outside a cell to inside a cell.

As used herein, the term "expression level and/or activity of a calpain" refers to the amount of a calpain found in a cell, tissue and/or subject, and/or a function of a calpain. Such functions can include, without limitation, its protease ability, its function in modulating TGFβ signaling, its function in myofibroblast transition (such as EpMT, EnMT, and/or FMT) and/or its function as a result of TRPM7-mediated calcium influx. In some embodiments, the expression level of a calpain refers to mRNA expression level. In other embodiments, the expression level of a calpain refers to protein expression level. In some embodiments, the myofibroblast transition is EpMT or EnMT (such as a TGFβ-mediated EpMT or EnMT). In some embodiments, at least one agent inhibits Fibroblast-to-Myofibroblast Transition (FMT). In some embodiments, the calpain is CAPN9 and/or CAPNS2.

The term "effective amount," as in "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition, or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy. Accordingly, as used herein, treatment of an disease associated with myofibroblast differentiation (such as an EpMT or EnMT-associated disease and/or an FMT-associated disease) in a subject in need thereof, includes, but is not limited to, reduction in the growth of fibrous tissue, halting the fibroproliferative state, reduction in the migration of fibroblasts or fibroblast precursors, reversal of the fibrosis, restoration of physiological organ function to a pre-fibrotic state, reduction in cancer growth or tumor burden, induction of cancer cell senescence, induction of apoptosis of cancer cells, induction of cancer cell death, inhibition of angiogenesis, enhancement of cancer cell apoptosis, and inhibition of metastases.

As used herein, the terms "treat," treating," "treatment," and the like, are meant to decrease, suppress, attenuate, diminish, arrest, the underlying cause of a disease, disorder, or condition, or to stabilize the development or progression of a disease, disorder, condition, and/or symptoms associated therewith. The terms "treat," "treating," "treatment," and the like, as used herein can refer to curative therapy, prophylactic therapy, and preventative therapy. The treatment, administration, or therapy can be consecutive or intermittent. Consecutive treatment, administration, or therapy refers to treatment on at least a daily basis without interruption in treatment by one or more days. Intermittent treatment or administration, or treatment or administration in an intermittent fashion, refers to treatment that is not consecutive, but rather cyclic in nature. Treatment according to the presently disclosed methods can result in complete relief or cure from a disease, disorder, or condition, or partial amelioration of one or more symptoms of the disease, disease, or condition, and can be temporary or permanent. The term "treatment" also is intended to encompass prophylaxis, therapy and cure.

As used herein, the terms "prevent," "preventing," "prevention," "prophylactic treatment" and the like refer to reducing the probability of developing a disease, disorder, or condition in a subject, who does not have, but is at risk of or susceptible to developing a disease, disorder, or condition. Thus, in some embodiments, an agent can be administered prophylactically to prevent the onset of a disease, disorder, or condition, or to prevent the recurrence of a disease, disorder, or condition.

As used herein, the term "subject" treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the diagnosis or treatment of an existing disease, disorder, condition or the prophylactic diagnosis or treatment for preventing the onset of a disease, disorder, or condition or an animal subject for medical, veterinary purposes, or developmental purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein. Subjects also include animal disease models (e.g., rats or mice used in experiments, and the like). In some embodiments, the subject is a human subject.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some aspects, ±100% in some aspects ±50%, in some aspects ±20%, in some aspects ±10%, in some aspects ±5%, in some aspects ±1%, in some aspects ±0.5%, and in some aspects ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Unless defined otherwise, all technical and scientific teams used herein have the meaning commonly understood by a person skilled in the art to which this invention belongs.

III. Methods of the Invention

A. Methods of Inhibiting Myofibroblast Differentiation

In one aspect, the presently disclosed subject matter relates to methods of inhibiting myofibroblast differentiation (such as Epithelial/Endothelial-to-Mesenchymal Transition (EpMT/EnMT) and/or Fibroblast-to-Myofibroblast transition (FMT)). In some embodiments, the methods comprise inhibiting myofibroblast differentiation (such as, Epithelial/Endothelial-to-Mesenchymal Transition (EpMT/EnMT)) by contacting a cell with at least one agent that decreases the expression level and/or activity of a calpain. In some embodiments, the calpain is CAPN9 and/or CAPNS2. In some embodiments, at least one agent inhibits (such as, specifically inhibits) CAPN9 and/or CAPNS2, or the interaction between CAPN9 and CAPNS2. In some embodiments, methods of inhibiting myofibroblast differentiation (such as, EpMT or EnMT) comprise contacting a cell with at least one calpain inhibitor that inhibits (such as, specifically inhibits) CAPN9 and/or CAPNS2.

In some embodiments, the presently disclosed subject matter provides a method for inhibiting myofibroblast differentiation (such as, Epithelial/Endothelial-to-Mesenchymal Transition (EpMT/EnMT)) comprising contacting a cell with at least one agent that decreases the level and/or activity of TRPM7. In some embodiments, the EpMT or EnMT is a TGFβ-mediated EpMT or EnMT. In some embodiments, the agent inhibits Fibroblast-to-Myofibroblast Transition (FMT). In some embodiments, at least one agent decreases the expression level and/or activity of TRPM7 without modulation of a calpain. In some embodiments, the cell is in a fibrotic tissue or is promoting fibrosis of the tissue. In some embodiments, the cell is contacted in a subject. In some embodiments, the subject is a human subject.

1. Epithelial/Endothelial to-Mesenchymal Transition (EpMT/EnMT)

EpMT and EnMT are processes whereby epithelial or endothelial cells that are normally non-fibrotic and non-motile undergo a transition into mesenchymal cells that are characterized by a proliferative and motile phenotype. It is a central mechanism for diversifying cells found in complex tissue, hence, is a process involved in organizing the formulation of the body plan (Kalluri and Nelson (2003) *J. Clin. Invest.* 112(12):1776-1784). Although epithelial cells were once considered to be terminally differentiated, it is recognized that epithelia possess an element of plasticity enabling transition to mobile mesenchymal cells (Boyer et al. (2000) *Biochem. Pharmacol.* 60:1099; Nieto (2002) *Nat. Rev. Mol. Cell Biol.* 3:155-166). EpMT is required, therefore, in adult tissue to enable formation of fibroblasts in injured tissues (Strutz et al. (1995) *J. Cell Biol.* 130:393-405; Iwano et al. (2002) *J. Clin. Invest.* 110:341-350) and in initiating, metastases in epithelial cancer (Kiermer et al. (2001) *Oncogene* 20:6679-6688; Janda et al. (2002) *J. Cell Biol.* 156:299-313Z; Xue et al. (2003) *Cancer Res.* 63:3386-3394).

EpMT and EnMT are, therefore, processes of disaggregating epithelial or endothelial units and re-shaping epithelia for movement in the formation of mesenchymal cells. The transition requires a molecular reprogramming of epithelium, generally considered to be by a variety of cytokines, metalloproteinases and membrane assembly inhibitors (Kalluri and Nelson (2003) *J. Clin. Invest.* 112(12):1776-1784; Yang and Liu (2001) *Am. J. Pathol.* 159:1465-1475; Zeisberg et al. (2001) *Am. J. Pathol.* 159:1313-1321.

2. Fibroblast-to-Myofibroblast Transition (FMT)

Fibroblasts are cells of the mesenchyme lineage whose main function is to provide structural support for the tissues through maintenance of extracellular matrix homeostasis. Fibroblasts play an important role during wound healing, where upon injury they are activated and facilitate productive scar formation to facilitate repair. Under pathological conditions, a large number of fibroblasts become myofibroblasts and promote accumulation of fibrotic scar tissue that fails to resolve. Although fibroblasts are from the mesenchymal lineage, they do not express αSMA until they become myofibroblast. Lineage tracing studies have suggested almost half of all myofibrobasts come from resident fibroblast. (Lebleu and Kalluri (2013) *Nat Med.* 19(8):1047-53).

3. Transforming Growth Factor Beta

"Transforming growth factor beta" (TGFβ) refers to a family of pleiotropic cytokines that inhibit the growth of most cell types (including epithelial cells, endothelial cells and lymphocytes). In mammals, the TGFβ family includes TGFβ1, -β2 and -β3. TGFβ is the most potent known stimulator for extracellular matrix synthesis and deposition and plays an important role in wound healing and tissue fibrosis. It has anti-inflammatory and pro-inflammatory activities, depending on the tissue studied. Among its anti-inflammatory activities, TGFβ suppresses the activity of T cells, B cells, macrophages and NK cells and inhibits the expression of several proinflammatory genes (Piccirillo et al. (1998) *J. Immunol.* 161:3950-3956; Prud'homme and Piccirillo (2000) *J. Autoimmun.* 14:23-42; Li et al. (2006) *Biochem. Biophys. Res. Commun.* 344:701-707). TGFβ is known to be a potent inducer of myofibroblast differentiation in multiple cellular contexts.

4. Calpain-9 and CAPNS2

CAPN9 or Calpain-9 is a protein in humans encoded by the CAPN9 gene (NCBI Gene ID: 10753; Lee et al. (1998) *Biol. Chem.* 379(2): 175-184; Yoshikawa et al. (2000) *Jpn. J. Cancer Res.* 91(5): 459-63). CAPNS2 or Calcium-Dependent Protease Small Subunit 2 is a protein in humans encoded by the CAPNS2 gene (NCBI Gene ID: 84290; Schád et al. (2002) *Biochem. J.,* 362:383-8). Calpains are a ubiquitous well-conserved family of calcium-dependent, cysteine proteases. Without wishing to be bound to any one particular theory, it is believed that the calpain proteins function as heterodimers consisting of a small regulatory subunit and a large catalytic subunit. The large catalytic subunit possesses a cysteine protease domain, and both subunits possess calcium-binding domains. CAPN9 is expressed predominantly in the gastrointestinal tract, including the stomach and small intestine. Nevertheless, CAPN9 and/or CAPNS2 expression may be increased in other tissues, if said tissues are in a diseased state, such as a fibrotic state. As such, generally, the methods of the presently disclosed subject matter can be used whether CAPN9 and CAPNS2 exist as a heterodimer or whether they do not exist together in a complex.

The presently disclosed subject matter contemplates the use of any agent that decreases the expression level and/or biological activity of a calpain (e.g., CAPN9 and/or CAPNS2), and/or any agent that decreases the expression level and/or activity of TRPM7. Exemplary types of agents that can be used in the methods described herein include small organic or inorganic molecules; saccharides; oligosaccharides; polysaccharides; a biological macromolecule selected from the group consisting of peptides, proteins, antibodies, peptide analogs and derivatives; peptidomimetics; inhibitory nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; microcarrier or nanocarrier consisting of one or more polymers, proteins, nucleic acids, lipids, or metals; and any combination thereof. A number of structurally diverse molecules with CAPN9 and/or CAPNS2 and/or TRPM7 inhibitory activity are known in the art.

5. Calpain Inhibitors

An agent disclosed herein (e.g., a CAPN9 inhibitor, CAPNS2 inhibitor and/or TRPM7 inhibitor) can be administered to a subject in combination with a pharmaceutically active agent. Exemplary pharmaceutically active agents include, but are not limited to, those found in Harrison's Principles of Internal Medicine, 13th Edition, eds. T. R. Harrison et al. McGraw-Hill N.Y., NY; Physicians' Desk Reference, 50th Edition, 1997, Oradell New Jersey, Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Gilman's The Pharmacological Basis of Therapeutics; and current edition of The Merck Index, the contents of all of which are incorporated herein by reference.

a. Small Molecule Chemical Compound Inhibitors

In some embodiments, the calpain inhibitor that inhibits (such as, specifically inhibits) CAPN9 and/or CAPNS2 is a small molecule chemical compound. Suitable small molecule chemical compounds include, without limitation, aldehydes, epoxides, and fluoro methyl ketones. In other embodiments, the calpain inhibitor is any of the inhibitors shown in Table 1 below.

b. RNA Interfering Agents

In some embodiments, the calpain inhibitor that inhibits (such as, specifically inhibits) CAPN9 and/or CAPNS2 is an RNA interfering agent. In this context, the calpain inhibitor that specifically inhibits CAPN9 and/or CAPNS2 inhibits gene expression (i.e., CAPN9 and/or CAPNS2 gene expression). Certain exemplary methods of assaying for CAPN9 and/or CAPNS2 gene expression or CAPN9 and/or CAPNS2 protein activity include, but are not limited to, those methods disclosed herein as well as assays known to those skilled in the art (see, e.g., Hata et al. (2010) *PloS Genet.* 6(7):e1001040; De Maria et al. (2009) *J. Biol. Chem.* 284(20):13542-50; Ma et al. (2004) *Curr. Eye Res.* 29(4-5): 337-347).

"RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn & Cullen (2002) *J. Virol.* 76:9225), thereby inhibiting expression of the target gene (see, e.g., U.S. Patent Application Nos: 20030153519A1; 20030167490A1; and U.S. Pat. Nos. 6,506,559; 6,573,099). An "RNA interfering agent" as used herein, is defined as any agent that interferes with or inhibits expression of a target gene, e.g., a marker of the presently disclosed subject matter, by RNA interference (RNAi). Such RNA interfering agents include, but are not limited to, peptides, proteins, antisense molecules, ribozymes, small inhibitory nucleic acid sequences, for example but not limited to guide RNAs, small interfering RNA (siRNA), short hairpin RNA or small hairpin RNA (shRNA), a microRNA (miRNA), post-transcriptional gene silencing RNA (ptgsRNA), short interfering oligonucleotides, antisense nucleotides, aptamers, CRISPR RNAs, nucleic acid molecules including RNA molecules which are homologous to the target gene, e.g., a marker of the presently disclosed subject matter, or a fragment thereof, and any molecule which interferes with or inhibit expression of a target gene by RNA interference (RNAi). In some embodiments, at least one agent is an RNA interfering agent. In some embodiments, the RNA is double stranded RNA (dsRNA).

In some embodiments, the RNA interfering agent is a siRNA. In some embodiment, the siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In some embodiments, the RNA interference agent is a small hairpin (also called stem loop) RNA (shRNA). In some embodiments, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart et al. (2003) RNA 9:493-501).

c. Protein or Peptidomimetic Inhibitors

In some embodiments, the calpain inhibitor that inhibits (such as, specifically inhibits) CAPN9 and/or CAPNS2 is an interfering agent that acts at the transcriptional level, such as proteins that act as transcriptional repressors, the nucleic acid sequences that encode for transcriptional repressors, and interfering agents involved in the CRISPR (clustered regularly interspaced palindromic repeats) pathway, such as guide RNAs and CRISPR RNAs.

In still other embodiments, the calpain inhibitor that inhibits (such as, specifically inhibits) CAPN9 and/or CAPNS2 is a peptidomimetic inhibitor.

In some embodiments, the agent may be chemically synthesized, may be produced by in vitro transcription, or may be produced within a host cell. In yet other embodiments, the calpain inhibitor is capastatin.

d. TRPM7 Inhibitors

In some embodiments, the calpain inhibitor that inhibits (such as, specifically inhibits) CAPN9 and/or CAPNS2 is an inhibitor that can be used to modulate TRPM7-mediated calcium influx. In some embodiments, at least one agent that decreases the level and/or activity of a calpain includes agents that modulate TRPM7-mediated calcium influx. Examples of agents that act with TRPM7 to mediate calcium influx include, but are not limited to, 1-Phosphatidylinositol-4,5-bisphosphate phosphodiesterase beta-1 (PLCB1), 1-Phosphatidylinositol-4,5-bisphosphate phosphodiesterase beta-2 (PLCB2), and reactive oxygen species (i.e., superoxide anion, hydrogen peroxide, etc.). PLCB1 is a protein that catalyzes the formation of inositol 1,4,5-trisphosphate and diacylglycerol from phosphatidylinositol 4,5-bisphosphate. PLCB2 catalyzes the formation of inositol 1,4,5-trisphosphate and diacylglycerol from phosphatidylinositol 4,5-bisphosphate. Reactive oxygen species generated by TGFβ signaling activate the TRPM7 channel. Furthermore, TGFβ-dependent activation of calcineurin activity is dependent on the generation of reactive oxygen species that induce calcium channel influx. TRPM7 also stimulates further generation of ROS, and can result in a positive feedback loop. Antioxidants (i.e. phenyleneoidonium) or scavengers of oxygen radicals (i.e. N-acetylcysteine) inhibit TGFβ induced calcium influx, through channels like TRPM7, and calcineurin activation. It has been found, in some embodiments, that at least one agent decreases TRPM7-mediated calcium influx.

In some embodiments, the calpain inhibitor that inhibits (such as, specifically inhibits) CAPN9 and/or CAPNS2 includes agents that modulate the expression and/or activity of TRPM7. In some embodiments, at least one agent that decreases the level and/or activity of a calpain includes agents that modulate the expression and/or activity of TRPM7. For example, agents that affect intracellular ATP levels also may modulate the expression and/or activity of TRPM7, such as protein kinase inhibitors. Functional and structural data also show that inhibitors against KCa2.1-2.3 channels (i.e. NS8593, dequalinium, SKA31 and UCL1684) can also inhibit TRPM7 channels due to a similar drug-binding site that when occupied, affects gating of the channels. In another example, derivatives of KCa2.1-2.3 channel inhibitors could be designed and synthesized to preferentially target the TRPM7 channels. KCa2.1-2.3 channels have known physiological roles in the nervous system (i.e. synaptic plasticity needed for learning and memory) and in the cardiovascular system (atrial fibrillation and atrial repolarization, such that chronic inhibition may lead to detrimental effects that would be minimized by derivatives with biased selectivity towards TRPM7. Sphingosine and its structural analogs (i.e. FTY720 a.k.a. Fingolimod a.k.a. Gilenya) can also inhibit TRPM7 by lowering the probability that the channel opens. In contrast, sphingosine kinase can phosphorylate sphingosine into sphingosine-1-phosphate, which does not affect TRPM7 channel opening, but does serve to lower sphingosine levels such that an inhibitor of sphinogine kinase may also act to decrease TRPM7 channel activity. In some embodiments, the calpain inhibitor comprises Fingolimod. In some embodiments, at least one agent that decreases the level and/or activity of TRPM7 comprises Fingolimod. In some embodiments, the calpain inhibitor comprises a derivative or structural analog of Fingolimod that decreases the level and/or activity of TRPM7.

In some embodiments, the calpain inhibitor that inhibits (such as, specifically inhibits) CAPN9 and/or CAPNS2 inhibits (such as, specifically inhibits) TRPM7. In some embodiments, at least one agent inhibits (such as, specifically inhibits) TRPM7. Examples of TRPM7 inhibitors include RNA interfering agents, such as siRNA; naturally derived substances, such as carvacrol (a bioactive monoterpenoid phenol), waixenicin A (from the soft coral *Sarcothelia edmondsoni*) quercetin (a flavonol found in food), and myriocin (a.k.a. ISP-1, a metabolite of the fungus *Isaria sinclairii*); small molecule chemical compounds, such as 2-aminoethoxydiphenyl borate (2-APB), SKF-96365, and NS8593; polyamines, such as spermine, 5-lipoxygenase inhibitors, such as NDGA, AA861, and MK886, and anti-TRPM7 antibodies. In some embodiments, at least one agent is a small molecule chemical compound. In some embodiments, the calpain inhibitor that specifically inhibits TRPM7 comprises Fingolimod.

B. Methods of Treating a Disease Associated with Myofibroblast Differentiation

In another aspect, the presently disclosed subject matter relates to methods of treating a disease associated with myofibroblast differentiation (such as an EpMT or EnMT-associated disease or an FMT-associated disease) in a subject in need thereof. In certain aspects, the presently disclosed subject matter provides a method of treating a disease associated with myofibroblast differentiation (for example, an Epithelial/Endothelial-to-Mesenchymal Transition (EpMT/EnMT)-associated disease) in a subject in need thereof comprising administering a therapeutically effective amount of at least one agent that decreases the level and/or activity of a calpain to the subject. In some embodiments, at least one agent inhibits Fibroblast-to-Myofibroblast Transition (FMT). In some embodiments, the calpain is CAPN9 and/or CAPNS2. In some embodiments, at least one agent inhibits (such as, specifically inhibits) CAPN9 and/or CAPNS2. In some embodiments, the calpain inhibitor that inhibits (such as, specifically inhibits) CAPN9 and/or CAPNS2 is a small molecule chemical compound and/or an RNA interfering agent such as, for example, siRNA (such as those discussed above). In some embodiments, at least one agent is a small molecule chemical compound. In some embodiments, at least one agent is an RNA interfering agent. In some embodiments, the RNA interfering agent is a siRNA.

In some embodiments, the methods include administering a therapeutically effective amount of at least one calpain inhibitor that inhibits (such as, specifically inhibits) CAPN9 and/or CAPNS2 to a subject having a disease associated with myofibroblast differentiation (such as an EpMT or an EnMT-associated disease). In some embodiments, the disease associated with myofibroblast differentiation (such as an EpMT or an EnMT-associated disease or an FMT-associated disease) is a fibrotic disease or a secondary disease, state, or condition thereof. In some embodiments, the disease associated with myofibroblast differentiation (such as an EpMT or an EnMT-associated disease) is a cancer, particularly a cancer of epithelial origin. In some embodiments, the disease associated with myofibroblast differentiation (such as an EpMT or an EnMT-associated disease) is a TGFβ-mediated disease associated with myofibroblast differentiation. The presently disclosed subject matter also contemplates the use of such calpain inhibitors for the treatment of a disease associated with myofibroblast differentiation (such as an EpMT or an EnMT-associated disease), such as a fibrotic disease or a secondary disease, state, or condition thereof. As used herein, the term "secondary disease, state, or condition" refers to a disease, state, or condition that follows and results from an earlier disease, state, or condition.

In some embodiments, at least one agent decreases TRPM7-mediated calcium influx. In some embodiments, at least one agent inhibits (such as, specifically inhibits) TRPM7. In some embodiments, at least one agent that inhibits TRPM7 and/or decreases TRPM7-mediated calcium influx is used for the treatment of a disease associated with myofibroblast differentiation (such as an EpMT or an EnMT-associated disease or an FMT-associated disease), such as a fibrotic disease or a secondary disease, state, or condition thereof.

1. Diseases Associated with Myofibroblast Differentiation

As used herein, "a cancer of epithelial origin" refers to a cancer that arises from epithelial cells which include, but are not limited to, breast cancer, basal cell carcinoma, adenocarcinoma, gastrointestinal cancer, lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body. In some embodiments, the cancer of epithelial origin is selected from the group consisting of breast cancer, basal cell carcinoma, adenocarcinoma, gastrointestinal cancer, lip cancer, mouth cancer, esophageal cancer, small bowel cancer, stomach cancer, colon cancer, liver cancer, brain, bladder cancer, pancreas cancer, ovary cancer, cervical cancer, lung cancer, skin cancer, prostate cancer, and renal cell carcinoma.

As used herein, "a fibrotic disease" includes, for example, liver fibrosis (alcoholic, viral, autoimmune, metabolic and hereditary chronic disease), renal fibrosis (e.g., resulting from chronic inflammation, infections, type II diabetes, ischemic-reperfusion, or organ transplants), lung fibrosis (idiopathic or resulting from environmental insults including toxic particles, sarcoidosis, asbestosis, hypersensitivity pneumonitis, bacterial infections including tuberculosis, medicines, organ transplants, etc.), interstitial fibrosis, systemic scleroderma (autoimmune disease in which many organs become fibrotic), macular degeneration (fibrotic disease of the eye), pancreatic fibrosis (resulting from, for example, alcohol abuse and chronic inflammatory disease of the pancreas), fibrosis of the spleen (from sickle cell anemia, other blood disorders) cardiac fibrosis (resulting from infection, inflammation and hypertrophy), mediastinal fibrosis, myelofibrosis, endomyocardial fibrosis, retroperitoneal fibrosis, progressive massive fibrosis, nephrogenic systemic fibrosis, fibrotic complications of surgery, especially surgical implants, chronic allograft vasculopathy and/or chronic rejection in transplanted organs, ischemic-reperfusion injury associated fibrosis, injection fibrosis and secondary conditions and disease states of fibrosis. Secondary conditions and disease states which occur as a consequence of or associated with fibrosis include for example, cirrhosis, diffuse parenchymal lung disease, post-vasectomy pain syndrome, stiff skin syndrome, and rheumatoid arthritis, among others. In some embodiments, the fibrotic disease or secondary disease state or condition thereof is selected from the group consisting of liver fibrosis, renal fibrosis, lung fibrosis, hypersensitivity pneumonitis, interstitial fibrosis, systemic scleroderma, macular degeneration, pancreatic fibrosis, fibrosis of the spleen, cardiac fibrosis, mediastinal fibrosis, myelofibrosis, endomyocardial fibrosis, retroperitoneal fibrosis, progressive massive fibrosis, nephrogenic systemic fibrosis, fibrotic complications of surgery, chronic allograft vasculopathy and/or chronic rejection in transplanted organs, ischemic-reperfusion injury associated fibrosis, injection fibrosis, cirrhosis, diffuse parenchymal lung disease, post-vasectomy pain syndrome, stiff skin syndrome, and rheumatoid arthritis.

2. Modes of Administration

As described herein, the calpain inhibitor that inhibits (such as, specifically inhibits) CAPN9 and/or CAPNS2 can be administered to a subject for therapy by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art.

The phrases "systemic administration," "administered systemically," "peripheral administration" and "administered peripherally" as used herein mean the administration of at least one calpain inhibitor that inhibits (such as, specifically inhibits) CAPN9 and/or CAPNS2 such that it enters the patient's system and, thus, is subject to metabolism and other like processes, for example, subcutaneous administration.

The phrases "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

The methods of the invention may be practiced in an adjuvant setting. "Adjuvant setting" refers to a clinical setting in which a subject has had a history of a disease, for example a disease associated with myofibroblast differentiation, such as cancer, and generally (but not necessarily) has been responsive to therapy, which includes, but is not limited to, surgery, radiotherapy, and chemotherapy. However, because of a history of the disease (such as cancer), these subjects are considered at risk of developing that disease. Treatment or administration in the "adjuvant setting" refers to a subsequent mode of treatment.

The methods provided herein may also be practiced in a "neoadjuvant setting," that is, the method may be carried out before the primary/definitive therapy. In some aspects, the subject has previously been treated. In other aspects, the subject has not previously been treated. In some aspects, the treatment is a first line therapy.

Regardless of the route of administration selected, compositions comprising a calpain inhibitor that inhibits (such as, specifically inhibits) CAPN9 and/or CAPNS2 may be formulated into pharmaceutically acceptable dosage forms. One skilled in the art can select appropriate formulation components, such as carriers, buffers, adjuvants, etc., according to the route of administration and/or the subject being treated.

Actual dosage levels of a calpain inhibitor that inhibits (such as, specifically inhibits) CAPN9 and/or CAPNS2 can be varied so as to obtain an amount of the active ingredient that is effective to achieve the desired therapeutic response for a particular subject, composition, route of administration, and disease, disorder, or condition without being toxic to the subject. The selected dosage level will depend on a variety of factors including the activity of the particular composition employed, the route of administration, the time of administration, the rate of excretion of the particular composition being employed, the duration of the treatment, other drugs, and/or materials used in combination with the particular composition employed, the age, sex, weight, condition, general health and prior medical history of the patient being treated, and like factors well known in the medical arts. Accordingly, a physician having ordinary skill in the art can readily determine and prescribe the effective amount of the presently disclosed composition required. Accordingly, the dosage range for administration will be adjusted by the physician as necessary, as described more fully elsewhere herein.

4. Additional Anti-Cancer Therapies

In some aspects, particularly when the disease associated with myofibroblast differentiation is a cancer of epithelial origin, any of the methods of treatment described herein can further comprise administering one or more additional anti-cancer therapies to the subject. Various classes of anti-cancer agents can be used. Non-limiting examples include: alkylating agents, antimetabolites, anthracyclines, plant alkaloids, topoisomerase inhibitors, podophyllotoxin, antibodies (e.g., monoclonal or polyclonal), tyrosine kinase inhibitors (e.g., imatinib mesylate (Gleevec® or Glivec®)), hormone treatments, soluble receptors and other antineoplastics.

Topoisomerase inhibitors are also another class of anti-cancer agents that can be used. Topoisomerases are essential enzymes that maintain the topology of DNA. Inhibition of type I or type II topoisomerases interferes with both transcription and replication of DNA by upsetting proper DNA supercoiling. Some type I topoisomerase inhibitors include camptothecins: irinotecan and topotecan. Examples of type II inhibitors include amsacrine, etoposide, etoposide phosphate, and teniposide. These are semisynthetic derivatives of epipodophyllotoxins, alkaloids naturally occurring in the root of American Mayapple (*Podophyllum peltatum*).

Antineoplastics include the immunosuppressant dactinomycin, doxorubicin, epirubicin, bleomycin, mechlorethamine, cyclophosphamide, chlorambucil, ifosfamide. The antineoplastic compounds generally work by chemically modifying a cell's DNA.

Alkylating agents can alkylate many nucleophilic functional groups under conditions present in cells. Cisplatin and carboplatin, and oxaliplatin are alkylating agents. They impair cell function by forming covalent bonds with the amino, carboxyl, sulfhydryl, and phosphate groups in biologically important molecules.

Vinca alkaloids bind to specific sites on tubulin, inhibiting the assembly of tubulin into microtubules (M phase of the cell cycle). The vinca alkaloids include: vincristine, vinblastine, vinorelbine, and vindesine.

Anti-metabolites resemble purines (azathioprine, mercaptopurine) or pyrimidine and prevent these substances from becoming incorporated in to DNA during the "S" phase of the cell cycle, stopping normal development and division. Anti-metabolites also affect RNA synthesis.

Plant alkaloids and terpenoids are derived from plants and block cell division by preventing microtubule function. Since microtubules are vital for cell division, without them, cell division cannot occur. The main examples are *vinca* alkaloids and taxanes.

Podophyllotoxin is a plant-derived compound which has been reported to help with digestion as well as used to produce two other cytostatic drugs, etoposide and teniposide. They prevent the cell from entering the G1 phase (the start of DNA replication) and the replication of DNA (the S phase).

Taxanes as a group includes paclitaxel and docetaxel. Paclitaxel is a natural product, originally known as Taxol and first derived from the bark of the Pacific Yew tree. Docetaxel is a semi-synthetic analogue of paclitaxel. Taxanes enhance stability of microtubules, preventing the separation of chromosomes during anaphase.

C. Rational Drug Design

In another aspect, the presently disclosed subject matter relates to methods of using a three-dimensional structure of a CAPN9/CAPNS2 heterodimer in a drug screening assay. In certain aspects the methods include: (a) selecting a potential drug by performing rational drug design with the three-dimensional structure of the CAPN9/CAPNS2 heterodimer determined from one or more sets of atomic coordinates, wherein the selection is performed in conjunction with computer modeling; (b) contacting the potential drug with the CAPN9/CAPNS2 heterodimer; (c) detecting the binding of the potential drug with the CAPN9/CAPNS2 heterodimer; and (d) detecting the inhibition of CAPN9/CAPNS2 heterodimer activity by the potential drug; wherein a potential drug is selected as a drug if the potential drug binds to and inhibits the CAPN9/CAPNS2 heterodimer. In some embodiments, the method includes a step (e) of disrupting the formation of the CAPN9CAPNS2 heterodimer.

A method of screening for a specific CAPN9/CAPNS2 inhibitor may involve isolating and purifying recombinant, enzymatically active CAPN9/CAPNS2 for use in combination with a calpain reporter substrate (for example, a commercially available fluorescent reporter substrate) or other reporter system (e.g., luciferase). In some embodiments, detecting the binding and inhibition of CAPN9/CAPNS2 heterodimer activity by the potential drug comprises the use of a fluorescent or luciferase-based calpain reporter substrate. In some aspects, the recombinant, enzymatically active CAPN9/CAPNS2 includes functional variants of CAPN9/CAPNS2, which include functional fragments, functional mutant proteins, and/or functional fusion proteins. In some embodiments, the CAPN9/CAPNS2 heterodimer comprises a functional variant of CAPN9/CAPNS2. A functional variant of a selected polypeptide refers to an isolated and/or recombinant protein or polypeptide which has at least one property, activity and/or functional characteristic of the selected polypeptide. As used herein, the term "activity," when used with respect to a wild-type polypeptide or its functional variant, e.g., CAPN9/CAPNS2, includes activities which are inherent in the structure of the wild-type polypeptide.

Compounds with inhibitory activity could also be counter-screened using recombinant CAPN1/CAPNS1, CAPN2/CAPNS1, CAPN9/CAPNS1, and CAPN1, and CAPN2 enzymes in order to demonstrate preference for the desired target (e.g., the selected drug that binds to and inhibits the CAPN9/CAPNS2 heterodimer is further counter-screened using CAPN1/CAPNS1 and/or CAPN2/CAPNS1 and/or CAPN9/CAPNS1 and/or CAPN1 and/or CAPN2 and/or functional variants thereof, wherein a drug that does not bind to and inhibit CAPN1/CAPNS1 and/or CAPN2/CAPNS1 and/or CAPN9/CAPNS1 and/or CAPN1 and/or CAPN2 and/or functional variants thereof is selected as a CAPN9/CAPNS2 specific inhibitor). Only the protease domain of CAPN9, referred to as "mini-CAPN9 has been successfully crystallized and has been hypothesized to have different inhibitory mechanisms compared to the conventional CAPN1 (Davis et al. (2007) J. Mol. Biol. 366:216-229). While CAPN1 auto-inhibition is dependent on occlusion of the active site by a helical loop, inactive CAPN9 has a misaligned catalytic triad which requires intradomain rearrangements for catalytic activity. Accordingly, in one aspect, the presently disclosed subject matter is also directed to specifically targeting the CAPN9 isoform, for example to stabilize the inactive CAPN9 and the misaligned catalytic triad with a rationally designed small molecule chemical compound. For example, in one aspect, a method is provided for using a three-dimensional structure of CAPN9 in a drug screening assay comprising: (a) selecting a potential drug by performing rational drug design with the three-dimensional structure of CAPN9 determined from one or more sets of atomic coordinates, wherein the selection is performed in conjunction with computer modeling; (b) contacting the potential drug with CAPN9; (c) detecting the binding of the potential drug with CAPN9; and (d) detecting the stability of CAPN9; wherein a potential drug is selected as a drug if the potential drug binds to and stabilizes CAPN9.

Criteria that may be employed by software programs used in rational drug design to qualify the binding of potential drugs with binding pockets and/or binding sites of the CAPN9/CAPNS2 heterodimer include gap space, hydrogen bonding, electrostatic interactions, van der Waals forces, hydrophilicity/hydrophobicity, etc. Generally, the greater the contact area between the screened drug and the CAPN9/CAPNS2 heterodimer binding region, the lower the steric hindrance, the lower the "gap space", the greater the number of hydrogen bonds, and the greater the sum total of the van der Waals forces between the screened drug and the CAPN9/CAPNS2 heterodimer binding region, the greater will be the capacity of the screened drug to bind with the target CAPN9/CAPNS2 heterodimer. The "gap space" refers to unoccupied space between the van der Waals surface of a screened drug positioned within a binding pocket or site and the surface of the binding pocket or site defined by amino acid residues in the binding pocket or site. Gap space may be identified, for example, using an algorithm based on a series of cubic grids surrounding the docked molecule, with a user-defined grid spacing, and represents volume that could advantageously be occupied by a modifying the docked drug positioned within the binding region of the CAPN9/CAPNS2 heterodimer.

In another aspect, the presently disclosed subject matter relates to methods of using a three-dimensional structure of the TRPM7 divalent cation channel in a drug screening assay. In certain aspects the methods include: (a) selecting a potential drug by performing rational drug design with the three-dimensional structure of the TRPM7 determined from one or more sets of atomic coordinates, wherein the selection is performed in conjunction with computer modeling or defining structure-activity relationships of various compounds with activity against KCa2.1-2.3 and/or TRPM7 and defining relative potency and biased selectivity for one of these channels (b) contacting the potential drug with the TRPM7 channel and counter-screening for binding to the KCa2.1-2.3 channels; (c) detecting the binding of the potential drugs; and (d) detecting the inhibition of TRPM7 channel activity by the potential drug through various methods (i.e. reporter systems, electrophysiological measurements).

A method of screening for a specific TRPM7 inhibitor may involve using structural and computational data to define subtle differences between similar drug binding pockets of TRPM7 and KCa2.1-2.3. Additional refinement or as a complete alternative, identification of a specific TRPM7 inhibitor could also be achieved by defining the structure activity relationships between known inhibitors of KCa2.1-2.3 and assessing their potency and selectivity bias for KCa2.1-2.3 and TRPM7 channel activity. Compounds could be tested for inhibitory activity against TRPM7 using a cell culture system, such as HEK293 cells, which overexpress either TRPM7 or KCa2.1-2.3 and express a DNA construct that encodes for enhanced green fluorescent protein fused to aequorin or alternatively a DNA construct that encodes for the protein based Cameleon calcium sensor.

Criteria that may be employed by software programs used in rational drug design to qualify the binding of potential drugs with binding pockets and/or binding sites of the TRPM7 and KCa2.1-2.3 include gap space, hydrogen bonding, electrostatic interactions, van der Waals forces, hydrophilicity/hydrophobicity, etc. Generally, the greater the contact area between the screened drug and the TRPM7, the lower the steric hindrance, the lower the "gap space", the greater the number of hydrogen bonds, and the greater the sum total of the van der Waals forces between the screened drug and the CAPN9/CAPNS2 heterodimer binding region, the greater will be the capacity of the screened drug to bind with the target TRPM7. Generally, the lesser the contact area between the screened drug and the KCa2.1-2.3, the greater the steric hindrance, the greater the "gap space", the lesser the number of hydrogen bonds, and the lesser the sum total of the van der Waals forces between the screened drug and the KCa2.1-2.3 binding region, the lesser will be the capacity of the screened drug to bind with the target TRPM7. The "gap space" refers to unoccupied space between the van der Waals surface of a screened drug positioned within a binding pocket or site and the surface of the binding pocket or site defined by amino acid residues in the binding pocket or site. Gap space may be identified, for example, using an algorithm based on a series of cubic grids surrounding the docked molecule, with a user-defined grid spacing, and represents volume that could advantageously be occupied by a modifying the docked drug positioned within the binding region of TRPM7.

Contact area between compounds may be directly calculated from the coordinates of the compounds in docked conformation using the MS program (Connolly (1983) Science 221:709-713).

Suitable software employing "scanner" type algorithms include, for example, docking software such as GRAM, DOCK, or AUTODOCK (reviewed in Dunbrack et al. (1997) Folding and Design 2:27), AFFINITY software of the INSIGHTII package (Molecular Simulations Inc., 1996, San Diego, Calif.), GRID (Goodford (1985) J. Med. Chem. 28:849-857; GRID is available from Oxford University, Oxford, UK), and MCSS (Miranker & Karplus (1991) Proteins: Structure Function and Genetics 11:29-34; MCSS is available from Molecular Simulations, Burlington, Mass.).

The AUTODOCK program (Goodsell & Olson (1990) Proteins: Struct Funct Genet. 8:195-202; available from Scripps Research Institute, La Jolla, Calif.) helps in docking screened molecules to binding pockets in a flexible manner using a Monte Carlo simulated annealing approach. The procedure enables a search without bias introduced by the researcher. This bias can influence orientation and conformation of a screened molecule in the targeted binding pocket The DOCK program (Kuntz et al. (1982) J. Mol. Biol. 161:269-288; available from University of California, San Francisco), is based on a description of the negative image of a space-filling representation of the binding pocket, and includes a force field for energy evaluation, limited conformational flexibility and consideration of hydrophobicity in the energy evaluation.

Modeling or docking may be followed by energy minimization with standard molecular mechanics force fields or dynamics with programs such as CHARMM (Brooks et al. (1983) J. Comp. Chem. 4:187-217) or AMBER (Weiner et al. (1984) J. Am. Chem. Soc. 106:765-784). As used herein, "minimization of energy" means achieving an atomic geometry of a chemical structure via systematic alteration such that any further minor perturbation of the atomic geometry would cause the total energy of the system as measured by a molecular mechanics force-field to increase. Minimization and molecular mechanics force fields are well understood in computational chemistry (e.g., Burkert & Allinger, "Molecular Mechanics", ACS Monograph 177, pp. 59-78, American Chemical Society, Washington, D.C. (1982)).

Programs employing "builder" type algorithms include LEGEND (Nishibata & Itai (1991) Tetrahedron 47:8985; available from Molecular Simulations, Burlington, Mass.), LEAPFROG (Tripos Associates, St. Louis, Mo.), CAVEAT (Bartlett et al. (1989) Special Pub Royal Chem Soc. 78:182-196; available from University of California, Berkeley), HOOK (Molecular Simulations, Burlington, Mass.), and LUDI (Bohm (1992) J. Comp. Aid Molec. Design 6:61-78; available from Biosym Technologies, San Diego, Calif.).

The CAVEAT program suggests binding molecules based on desired bond vectors. The HOOK program proposes docking sites by using multiple copies of functional groups in simultaneous searches. LUDI is a program based on fragments rather than on descriptors which proposes somewhat larger fragments to match with a binding pocket and scores its hits based on geometric criteria taken from the Cambridge Structural Database (CSD), the Protein Data Bank (PDB) and on criteria based on binding data. LUDI may be advantageously employed to calculate the inhibition constant of a docked chemical structure. Inhibition constants (Ki values) of compounds in the final docking positions can be evaluated using LUDI software.

During or following rational drug design, docking of an intermediate chemical structure or of a drug with the CAPN9/CAPNS2 heterodimer binding pocket or site may be visualized via structural models, such as three-dimensional models, thereof displayed on a computer screen, so as to advantageously allow user intervention during the rational drug design to optimize a chemical structure.

Software programs useful for displaying such three-dimensional structural models, include RIBBONS (Carson (1997) Methods in Enzymology 277:25), 0 (Jones et al. (1991) Acta Crystallogr. A47:110), DINO; and QUANTA, INSIGHT, SYBYL, MACROMODE, ICM, MOLMOL, RASMOL and GRASP (reviewed in Kraulis (1991) Appl Crystallogr. 24:946).

Other molecular modeling techniques may also be employed in accordance with the presently disclosed subject matter (e.g., Cohen et al. (1990) J. Med. Chem. 33:883-894; Navia & Murcko (1992) Current Opinions in Structural Biology 2:202-210). For example, where the structures of test compounds are known, a model of the test compound may be superimposed over the model of the structure of the drugs as disclosed herein. Numerous methods and techniques are known in the art for performing this step, any of which may be used (e.g., Farmer "Drug Design", Ariens (ed.), Vol. 10, pp 119-143 (Academic Press, New York, 1980); U.S. Pat. No. 5,331,573; U.S. Pat. No. 5,500,807; Verlinde (1994) Structure 2:577-587; and Kuntz (1992) Science 257:1078-108).

An alternative approach to rational drug design comprises use of the 27-amino acid calpastatin peptide, which has been demonstrated to be sufficient for calpain inhibition, as a base template for the design of derivatives (e.g., functional variants) that strongly prefer the CAPN9/CAPNS2 heterodimer and/or CAPN9 and/or mini-CAPN9 and/or functional variants thereof (e.g. catalytically inactive mutants) and counter-screened against CAPN9/CAPNS1 and/or CAPN1 and/or CAPN1/CAPNS1 and/or CAPN1/CAPNS2 and/or CAPN2 and/or CAPN2/CAPNS1 and/or CAPN2/CAPNSS or any functional variant thereof. Such an approach would require the addition of a cell penetrating peptide or other moiety to facilitate intracellular delivery. This method takes advantage of the already high potency of this inhibitor but alters specificity towards the pathological targets.

D. Methods for Identifying an Agent Capable of Modulating the Activity of CAPN9 and/or CAPNS1

Provided herein are methods for identifying an agent capable of modulating the activity and/or expression level of CAPN9 and/or CAPNS2 in a cell that has yet to undergo, is undergoing, or has undergone myofibroblast differentiation. The method is performed by contacting a cell that expresses CAPN9 and/or CAPNS2 with a candidate agent and then determining whether the agent modulates the activity and/or expression level of CAPN9 and/or CAPNS2. In some embodiments, myofibroblast differentiation may result from Epithelial-to-Mesenchymal Transition, Endothelial-to-Mesenchymal Transition, or Fibroblast-to-Myofibroblast Transition and, in further embodiments, can be mediated by TGFβ. Examples of cells that can be utilized in these methods include, without limitation, endothelial cells, epithelial cells (such as, NMuMG cells), fibroblasts, or myofibroblasts. In a particular embodiment, the agent can suppress bleomycin-induced lung fibrosis in mice, carbon tetrachloride-induced liver fibrosis, thioacetamide-induced liver fibrosis, dimethylnitrosamine-induced liver fibrosis, bile duct ligation-induced liver fibrosis, unilateral ureter obstruction induced kidney fibrosis, 5/6 nephrectomy induced kidney fibrosis, diabetes-induced kidney fibrosis, streptozotocin-induced kidney fibrosis, western high fat diet induced kidney and liver fibrosis, combined western high fat diet and streptozotocin induced liver and kidney fibrosis.

The expression level and/or activity of any of the genes and/or proteins disclosed herein can be assessed by any means known in the art and can include, for example, mRNA expression assays (such as Northern Blot, in situ hybridization, SAGE, RT-PCR, or another PCR-based assays) and protein expression assays (such as Western blot, immunohistochemistry, immunocytochemistry, ELISA, RIA, or any other antibody-based technique).

In some embodiments, the agent modulates the activity of CAPN9 and/or CAPNS2 by decreasing the expression level or activity of one or both of these proteins in a cell that has yet to undergo, is undergoing, or has undergone myofibroblast differentiation. The agent can decrease the expression level or activity of CAPN9 and/or CAPNS2 by any of about 5%, 10%, 15%, 20%, 25%, 30%, 35%, 40%, 45%, 50%, 55%, 60%, 65%, 70%, 75%, 80%, 85%, 90%, 95%, or 100% (inclusive of values falling in between these percentages) in a cell that has yet to undergo, is undergoing, or has undergone myofibroblast differentiation compared to the expression level or activity of CAPN9 and/or CAPNS2 in similar cells that are not contacted by the agent.

Further, the agent capable of modulating the activity of CAPN9 and/or CAPNS2 can also modulate the activity or expression levels of one or more proteins expressed by the cell which directly or indirectly interact with, or whose expression or activity is influenced by, the expression level and/or activity of CAPN9 and/or CAPNS2. For example, the agent capable of modulating the activity of CAPN9 and/or CAPNS2 can also decrease the activity or expression level of one or more proteins, such as, but not limited to, α-SMA, calcineurin, cleaved calcineurin, constitutively active calcineurin, cleaved and constitutively active calcineurin, collagen, and/or one or more matrix metalloproteinases. In some embodiments, the agent decreases the expression or activity of one or more of α-SMA, calcineurin, cleaved calcineurin, constitutively active calcineurin, cleaved and constitutively active calcineurin, collagen, and/or one or more matrix metalloproteinases by any of about 5%, 10%, 15%, 20%, 25%, 30%, 35%, 40%, 45%, 50%, 55%, 60%, 65%, 70%, 75%, 80%, 85%, 90%, 95%, or 100% (inclusive of values falling in between these percentages) in a cell that has yet to undergo, is undergoing, or has undergone myofibroblast differentiation compared to the expression level or activity of these proteins in similar cells that are not contacted by the agent.

In another embodiment, the agent capable of modulating the activity of CAPN9 and/or CAPNS2 can prevent or decrease cleavage of calcineurin into a constitutively active form. Calcineurin is a calcium and calmodulin-dependent serine/threonine protein phosphatase (also known as protein phosphatase 3, and calcium-dependent serine-threonine phosphatase). Previous reports have indicated that calcineurin is cleaved by calpains in such a way as to remove the auto-inhibitory region of calcineurin, thereby causing its constitutive activation. Accordingly, in some embodiments, the agent prevents or decreases cleavage of calcineurin into a constitutively active form by any of about 5%, 10%, 15%, 20%, 25%, 30%, 35%, 40%, 45%, 50%, 55%, 60%, 65%, 70%, 75%, 80%, 85%, 90%, 95%, or 100% (inclusive of values falling in between these percentages) in a cell that has yet to undergo, is undergoing, or has undergone myofibroblast differentiation compared to the amount of calcineurin cleavage in similar cells that are not contacted by the agent.

In another embodiment, the agent capable of modulating the activity of CAPN9 and/or CAPNS2 can increase or maintain the activity or expression level of calpastatin and/or E-cadherin. The agent can increase the activity or expression level of calpastatin and/or E-cadherin by any of about 5%, 10%, 15%, 20%, 25%, 30%, 35%, 40%, 45%, 50%, 55%, 60%, 65%, 70%, 75%, 80%, 85%, 90%, 95%, or 100% (inclusive of values falling in between these percentages) in a cell that has yet to undergo, is undergoing, or has undergone myofibroblast differentiation compared to the expression level or activity of these proteins in similar cells that are not contacted by the agent.

In still further embodiments, the agent capable of modulating the activity of CAPN9 and/or CAPNS2 also inhibits the activity or expression of one or more transient receptor potential ion channel subfamily M (TRPM) family members. TRPs, mammalian homologs of the *Drosophila* transient receptor potential (trp) protein, are ion channels that are thought to mediate capacitative calcium influx into the cell. The TRPM family consists of eight different channels, TRPM1-TRPM8. Accordingly, since CAPN9 and/or CAPNS2 are calcium dependent polypeptides, the agent capable of modulating the activity of CAPN9 and/or CAPNS2 can exert its influence by modulating the expression level or activity of a TRPM family member by decreasing or preventing its expression in a cell or by inhibiting its ability to mediate calcium influx into the cell. In some embodiments, the agent decreases the expression or activity of one or more TRPM family members by any of about 5%, 10%, 15%, 20%, 25%, 30%, 35%, 40%, 45%, 50%, 55%, 60%, 65%, 70%, 75%, 80%, 85%, 90%, 95%, or 100% (inclusive of values falling in between these percentages) in a cell that has yet to undergo, is undergoing, or has undergone myofibroblast differentiation compared to the expression level or activity of the same TRPM family members in similar cells that are not contacted by the agent. In some embodiments, the TRPM family member is TRPM7.

In another embodiment, the agent capable of modulating the activity of CAPN9 and/or disrupts an intracellular interaction between the CAPN9 and CAPNS2 proteins. However, generally, the methods of the presently disclosed subject matter can be used whether CAPN9 and CAPNS2 exist as a heterodimer or whether they do not interact intracellularly.

The agent capable of modulating the activity and/or expression level of CAPN9 and/or CAPNS2 can be an antibody or a non-antibody polypeptide. Additionally, the agent can be an inhibitory nucleic acid, such as an antisense oligonucleotide or an siRNA directed to one or both of the mRNAs encoding these proteins which results in decreased cellular CAPN9 and/or CAPNS2 expression. Further, the agent can also be a small molecule chemical compound.

1. Antibodies

In some aspects, the agent capable of modulating the activity and/or expression level of CAPN9 and/or CAPNS2 is an antibody. Antibodies are proteins that bind, preferably specifically, to other proteins, nucleic acids, lipids, or any other antigen (such as to CAPN9 and/or CAPNS2). In some embodiments, the antibody binds to a TRPM family calcium channel, for example, TRPM7. Variants of antibodies can be made based on information known in the art, without substantially affecting the activity of antibody. For example, antibody variants can have at least one amino acid residue in the antibody molecule replaced by a different residue. Fragments of antibodies may also be used (such as, but not limited to, Fv, Fab, Fab', or F(ab)2 fragments), as well as genetically-engineered antibodies or antigen binding fragments thereof, including single chain antibodies, humanized antibodies, antibodies that can bind to more than one epitope (e.g., bi-specific antibodies), or antibodies that can bind to one or more different antigens (e.g., bi- or multi-specific antibodies), may also be employed. For antibodies, the sites of greatest interest for substitutional mutagenesis generally include the hypervariable regions, but framework region (FR) alterations are also contemplated. For antibodies, one type of substitutional variant involves substituting one or more hypervariable region residues of a parent antibody (e.g. a humanized or human antibody). Generally, the resulting variant(s) selected for further development will have improved biological properties (e.g., affinity) relative to the parent antibody from which they are generated.

A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody. It may be desirable to introduce one or more amino acid modifications in an Fc region of the immunoglobulin polypeptides of the invention, thereby generating a Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

2. Non-Antibody Binding Polypeptides

In some aspects, the agent capable of modulating the activity and/or expression level of CAPN9 and/or CAPNS2 is a non-antibody binding polypeptide. Binding polypeptides may be chemically synthesized using known polypeptide synthesis methodology or may be prepared and purified using recombinant technology. Binding polypeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such binding polypeptides that are capable of binding, preferably specifically, to CAPN9 and/or CAPNS2. In some embodiments, the non-antibody binding polypeptide binds to a TRPM family calcium channel, for example, TRPM7. Binding polypeptides may be identified without undue experimentation using well known techniques. In this regard, it is noted that techniques for screening polypeptide libraries for binding polypeptides that are capable of binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., *Proc. Natl. Acad. Sci. U.S.A.*, 81:3998-4002 (1984); Geysen et al., *Proc. Natl. Acad. Sci. U.S.A.*, 82:178-182 (1985); Geysen et al., in Synthetic Peptides as Antigens, 130-149 (1986); Geysen et al., *J. Immunol. Meth.*, 102:259-274 (1987); Schoofs et al., *J. Immunol.*, 140:611-616 (1988), Cwirla, S. E. et al., (1990) *Proc. Natl. Acad. Sci. USA*, 87:6378; Lowman, H. B. et al., (1991) Biochemistry, 30:10832; Clackson, T. et al., (1991) *Nature*, 352: 624; Marks, J. D. et al., (1991), *J. Mol. Biol.*, 222:581; Kang, A. S. et al., (1991) *Proc. Natl. Acad. Sci. USA*, 88:8363, and Smith, G. P. (1991) *Current Opin. Biotechnol.*, 2:668).

3. Small Molecule Chemical Compounds

In some aspects, the agent capable of modulating the activity and/or expression level of CAPN9 and/or CAPNS2 is a small molecule chemical compound. Small molecules can be molecules other than binding polypeptides or antibodies as defined herein that bind to CAPN9 and/or CAPNS2. In some embodiments, the small molecule chemical compound binds to a TRPM family calcium channel, for example, TRPM7. Small molecules may be identified and chemically synthesized using known methodology (see, e.g., International Patent Application Publication Nos. WO00/00823 and WO00/39585). Small molecules are usually less than about 2000 Daltons in size or alternatively less than about 1500, 750, 500, 250 or 200 Daltons in size, wherein such small molecules that are capable of binding, preferably specifically, to a CAPN9 and/or CAPNS2 polypeptide as described herein may be identified without undue experimentation using well known techniques. In this regard, it is noted that techniques for screening small molecule libraries for molecules that are capable of binding to a polypeptide target are well known in the art (see, e.g., PCT Publication Nos. WO00/00823 and WO00/39585). Small molecules may be, for example, aldehydes, epoxides, or fluoro methyl ketones.

The small molecule chemical compound may be a component of a combinatorial chemical library. Combinatorial chemical libraries are a collection of multiple species of chemical compounds comprised of smaller subunits or monomers. Combinatorial libraries come in a variety of sizes, ranging from a few hundred to many hundreds of thousand different species of chemical compounds. There are also a variety of library types, including oligomeric and polymeric libraries comprised of compounds such as carbohydrates, oligonucleotides, and small organic molecules, etc. Such libraries have a variety of uses, such as immobilization and chromatographic separation of chemical compounds, as well as uses for identifying and characterizing ligands capable of binding an acceptor molecule (such as a CAPN9 and/or CAPNS2 protein) or mediating a biological activity of interest (such as, but not limited to, inhibition of cellular proliferation or fibrosis). Various techniques for synthesizing libraries of compounds on solid-phase supports are known in the art. Solid-phase supports are typically polymeric objects with surfaces that are functionalized to bind with subunits or monomers to form the compounds of the library. Synthesis of one library typically involves a large number of solid-phase supports. To make a combinatorial library, solid-phase supports are reacted with one or more subunits of the compounds and with one or more numbers of reagents in a carefully controlled, predetermined sequence of chemical reactions. In other words, the library subunits are "grown" on the solid-phase supports. The larger the library, the greater the number of reactions required, complicating the task of keeping track of the chemical composition of the multiple species of compounds that make up the library. In some embodiments, the small molecules are less than about 2000 Daltons in size, alternatively less than about 1500, 750, 500, 250 or 200 Daltons in size.

4. Inhibitory Nucleic Acids

In another aspect, the agent is one or more inhibitory nucleic acid(s). The inhibitory nucleic acid can be, without limitation, any of an RNA interference agent, such as any of those disclosed herein (for example, an antisense oligonucleotide, a siRNA, a dsRNA, or a ribozyme). While preferred, absolute complementarity of an inhibitory nucleic acid to a target is not required. As used herein, an inhibitory nucleic acid sequence is "complementary" to a target nucleic acid (such as a nucleic acid encoding CAPN9 and/or CAPNS2 or a nucleic acid encoding a TRPM family member, e.g. TRPM7) when the inhibitory nucleic acid has a sequence sufficiently complementary to be able to hybridize with the target, thereby forming a stable duplex. The ability to hybridize will depend on both the degree of complementarity and the length of the oligonucleotide. Generally, the longer the hybridizing inhibitory nucleic acid, the more base mismatches with a given target it may contain and still form a stable duplex. A person having ordinary skill in the art can ascertain a tolerable degree of mismatch by use of standard procedures to determine the melting point of the hybridized complex.

Inhibitory nucleic acids can include one or more alternate internucleoside linkages, such as, but not limited to, phosphorothioate (Mag at al., *Nucleic Acids Res.* 19: 1437-1441, 1991; and U.S. Pat. No. 5,644,048), peptide nucleic acid or PNA (Egholm, *Nature,* 3685:566-568, 1993; and U.S. Pat. No. 6,656,687), phosphoramide (Beaucage, *Methods Mol. Biol.* 20:33-61, 1993), phosphorodithioate (Capaldi et al., *Nucleic Acids Res.,* 28:E40, 2000). Other oligonucleotide analogs include, but are not limited to, morpholino (Summerton, *Biochim. Biophys. Acta,* 1489: 141-158, 1999), locked oligonucleotides (Wahlestedt wt al., *Proc. Natl. Acad. Sci. USA,* 97:5633-5638, 2000), peptidic nucleic adds or PNA (Nielsen et al., 1993; Hyrup and Nielsen, 1996) or 2-o-(2-methoxy)ethyl modified 5' and 3' end oligonucleotides (McKay et al., *Biol. Chem.,* 274: 1715-1722, 1999). All of the preceding publications are hereby expressly incorporated by reference.

Further, any of the inhibitory nucleic acids disclosed herein may additionally contain any combination of deoxyribo- and/or ribonucleotides, as well as any combination of natural and/or synthetic bases, including uracil, adenine, thymine, cytosine, guanine, inosine, xathanine hypoxathanine, isocytosine, isoguanine, etc.

The inhibitory nucleic acids discussed herein can include one or more modified base moiety such as, but not limited to, 5-fluorouracil, 5-bromouracil, 5-chlorouracil, 5-Iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxy acetic acid methylester, uracil-5-oxyacetic acid (v), 5-methyl-2-thiouracil, 3-(3-amino-3-N2-carboxypropyl)uracil, (acp3)w, and/or 2,6-diaminopurine.

Inhibitory nucleic acids contemplated within the scope of the present invention can also have one or more modified sugar moiety such as, but not limited to, arabinose, 2-fluoroarabinose, xylulose, and hexose. The inhibitory nucleic acids of the present invention should be at least ten nucleotides in length, and may range from 10 to about 50 nucleotides in length, such as 15, 20, 30, 35, 40, 45, or 50 nucleotides in length, inclusive, including any values falling in between these numbers.

E. Diagnostic Methods

Provided herein are methods for identifying a subject who would benefit from treatment with a CAPN9 and/or CAPNS2 inhibitor. The method is performed by assaying for the presence of a CAPN9 and/or CAPNS2 mRNA or protein in a biological sample obtained from the subject, wherein the presence of CAPN9 and/or CAPNS2 mRNA or protein in the biological sample identifies the subject as benefiting from treatment with a CAPN9 and/or CAPNS2 inhibitor. Any assay known in the art can be used to detect the presence of a CAPN9 and/or CAPNS2 mRNA or protein in the biological sample, including those assays described herein. The biological sample can be obtained from the subject by any means known in the art (such as, but not limited to, needle or core biopsy, fine needle aspiration, tumor resection, or from serum) and can be processed for analysis by any means known in the art (such as, but not limited to, fixation, embedding in paraffin, or freezing). In some embodiments, the sample contains one or more epithelial, endothelial, fibroblast, or myofibroblast cells. In another embodiment, the subject is diagnosed with or thought to have one or more diseases associated with myofibroblast differentiation, such as any of those described herein.

Also provided herein are methods for determining if a subject diagnosed with one or more diseases associated with myofibroblast differentiation (such as any of those described herein) is responding to administration of and/or treatment with a CAPN9 and/or CAPNS2 inhibitor. The method is performed by determining if the expression level or activity of CAPN9 and/or CAPNS2 is modulated in a biological sample obtained from the subject following administration of and/or treatment with the CAPN9 and/or CAPNS2 inhibitor, wherein the subject is responding to treatment if the activity or expression level of CAPN9 and/or CAPNS2 in the biological sample is modulated. The expression level or activity of CAPN9 and/or CAPNS2 can be assessed using any means known in the art, including those described herein. Further, modulation of the activity or expression levels of one or more proteins expressed by a cell which directly or indirectly interact with, or whose expression or activity is influenced by, the expression level and/or activity of CAPN9 and/or CAPNS2 (such as, but not limited to, smooth muscle actin (α-SMA), calcineurin, cleaved calcineurin, constitutively active calcineurin, cleaved and constitutively active calcineurin, calpastatin, E-cadherin, vimentin, collagen, heat shock protein 47 (Hsp47), TRPM7, and/or one or more matrix metalloproteinases) can also be assessed to determine whether the subject is responding to administration of and/or treatment with a CAPN9 and/or CAPNS2 inhibitor by conventional means known in the art (such as those described herein).

Further provided herein are methods for identifying whether a subject diagnosed with one or more diseases associated with myofibroblast differentiation will benefit from treatment with a calcineurin inhibitor. The method is performed by assaying for the presence of a CAPN9 and/or CAPNS2 mRNA and/or cleaved calcineurin and/or constitutively active calcineurin and/or cleaved and/or constitutively active calcineurin or protein in a biological sample obtained from the subject, wherein the presence of CAPN9 and/or CAPNS2 mRNA and/or cleaved calcineurin and/or constitutively active calcineurin and/or cleaved and/or constitutively active calcineurin or protein in the biological sample identifies the subject as benefiting from treatment with a calcineurin inhibitor. Any assay known in the art can be used to detect the presence of a CAPN9 and/or CAPNS2 mRNA or protein in the biological sample, including those described herein. The biological sample can be obtained from the subject by any means known in the art (such as, but not limited to, needle or core biopsy, fine needle aspiration, tumor resection, or isolated from serum) and can be processed for analysis by any means known in the art (such as, but not limited to, fixation, being embedded in paraffin, or freezing). In some embodiments, the sample contains one or more epithelial, endothelial, fibroblast, or myofibroblast cells. In another embodiment, the subject is diagnosed with or thought to have one or more diseases associated with myofibroblast differentiation, such as any of those described herein.

F. Methods for Identifying an Agent Capable of Inhibiting of a TRP Calcium Channel Provided herein are methods for identifying an agent capable of inhibiting a TRP calcium channel, wherein inhibition of the TRP calcium channel prevents myofibroblast differentiation. The method is performed by contacting a cell with the agent, wherein the cell expresses (i) CAPN9 and/or CAPNS2 and (ii) a TRP calcium channel and then identifying whether the agent prevents myofibroblast differentiation. The TRP calcium channel can be a TRPM calcium channel, for example, any of TRPM1, TRPM2, TRPM3, TRPM4, TRPM5, TRPM6, TRPM7 and/or TRPM8. The agent can alter the expression levels of activity of a TRP calcium channel, such as preventing its transcription or translation, or by functionally blocking its ability to mediate calcium influx into the cell. Whether the agent prevents myofibroblast differentiation can be assessed by, for example, determining if the agent alters the activity or expression level of CAPN9 and/or CAPNS2. Additionally, myofibroblast differentiation can be assessed by determining the activity or expression levels of one or more proteins expressed by a cell which directly or indirectly interact with, or whose expression or activity is influenced by, the expression level and/or activity of CAPN9 and/or CAPNS2 (such as, but not limited to, smooth muscle actin (α-SMA), vimentin, calcineurin, cleaved calcineurin, constitutively active calcineurin, cleaved, constitutively active calcineurin, calpastatin, E-cadherin, collagen, and/or one or more matrix metalloproteinases). The agent can be, without limitation, any of an antibody or fragment thereof, a small molecule chemical compound, a non-antibody peptide, or an inhibitory nucleic acid, such as any of those described herein.

It should be understood that the following examples should not be construed as being limiting to the particular methodology, protocols, and compositions, etc., described herein and, as such, can vary. The following terms used herein are for the purpose of describing particular embodiments only, and are not intended to limit the scope of the embodiments disclosed herein.

EXAMPLES

The following Examples have been included to provide guidance to one of ordinary skill in the art for practicing representative embodiments. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Summary:

Expression profiling studies associate enhanced expression/activity of the calpain family of cysteine proteases with multiple genetic or environmentally-induced TGFβ-related disease processes including fibrosis and tumor metastasis. The underlying mechanistic connection (if any) remains unknown. We reasoned that this association might relate to TGFβ-induced mesenchymal transition, the process by which cells of epithelial or endothelial origin lose polarity and cell adhesion and adopt an invasive character and fibrotic synthetic repertoire (EpMT). This hypothesis was tested in NMuMG epithelial cells which show striking EpMT within 2 days of TGFβ1 administration, as evidenced by downregulation of E-cadherin, transition from a cortical to a stress fiber distribution of F-actin, and upregulation of α-smooth muscle actin, collagen, and matrix metalloproteinases. As described below, concomitant treatment with a broad inhibitor of TGFβ signaling (SB431542) prevented EpMT in association with attenuation of intracellular TGFβ1 signal propagation (phosphorylation of Smad2/3). In contrast, inhibition of calpain activity (as evidenced by failed cleavage of the natural calpain substrate FLNA) with the broad-spectrum calpain inhibitors MDL-28170 or calpeptin abrogated EpMT despite maintenance of the pSmad2/3 response. Furthermore, robust EpMT inhibition was achieved using either 2-aminoethoxydiphenyl borate (2-APB) (a non-specific inhibitor reported to prevent the TRPM7-mediated calcium influx needed for calpain activation), NS8593 (a TRPM7 specific inhibitor that is reported to prevent the TRPM7-mediated calcium influx needed for calpain activation) or overexpression of calpastatin, a naturally-occurring and highly specific dimeric calpain inhibitor. Among dimeric calpains, the CAPN1 and CAPN2 large subunits and CAPNS1 small subunit show broad expression, however siRNA-mediated silencing of these specific isoforms failed to suppress EpMT. In contrast, we show that the relatively obscure CAPN9 and CAPNS2 subunits only show physiologic expression in the GI tract and skin, respectively, but are potently induced by TGFβ1 in both epithelial and endothelial cells; siRNA-mediated silencing of either abrogated EpMT in culture systems. Identical provocations prevented EnMT in endothelial cell lines, FMT in fibroblast cell lines, and also showed the capacity to reverse an established mesenchymal phenotype (MET) in differentiated myofibroblasts. Taken together, these data suggest that calpain inhibition is an attractive therapeutic strategy for multiple TGFβ pathologies and lend optimism that CAPN9/S2 inhibition will have a greater influence on pathologic vs. physiologic events and will therefore exhibit a favorable tolerance profile.

Example 1: Targeting Calpains as a Novel Strategy Towards Inhibition of EpMT It has been discovered that small molecule pan-calpain inhibitors, such as MDL-28170, antagonize TGFβ1-induced EpMT as measured by αSMA expression in Namru Mouse Mammary Gland Epithelial cells (NMuMG) and Marine-Darby Canine Kidney Epithelial Cells (MDCK), demonstrating for the first time that calpain enzymatic activity is necessary for TGFβ-induced EpMT (FIG. 1A, FIG. 1B, FIG. 1C, FIG. 1D, FIG. 1E, and FIG. 1F). Calpain inhibition was found not to affect early TGFβ1 signaling events such as the accumulation of phospho-SMAD2, suggesting that calpains are a downstream event during the induction of EpMT and that this type of inhibition may not affect upstream physiological signaling (FIG. 1A and FIG. 1B). Calpain inhibition was also found to suppress TGFβ-induced expression of genes commonly and functionally associated with fibrosis, such as collagen 1A1, vimentin and matrix metalloproteinase 2/9 (FIG. 1C). A profound decrease in E-cadherin, a cell surface protein highly expressed by epithelial cells, was observed by immunofluorescence upon stimulation with TGFβ but was prevented by treatment with calpain inhibitor MDL-28170 (FIG. 1D). TGFβ1 also induced reorganization of the actin cytoskeleton from a cortical arrangement in epithelial cells to long parallel stress fibers that are indicative of a mesenchymal phenotype and was blocked by calpain inhibitor MDL-28170 (FIG. 1D). The small molecule calpain inhibitor MDL-28170 also suppresses TGFβ-induced EpMT in MDCK cells as measured from αSMA expression by western blot (FIG. 1E) and quantified western blot data of αSMA in biological replicates. (FIG. 1F).

As a control, NMuMG cells treated with TGFβ along with the TGFβ receptor kinase inhibitor SB431542, did not show TGFβ-dependent phosphorylation of SMAD2, increased αSMA expression, or calpain activity (FIG. 1G, FIG. 1H). If TGFβ-induced calpain activity is necessary to maintain myofibroblast differentiation, suppression of calpain activity after pre-establishment of myofibroblast differentiation should be sufficient for mesenchymal-to-epithelial transition and provide evidence supporting reversal of a disease state. NMuMG cells, pretreated with TGFβ for 72 h to establish myofibroblast differentiation, when then treated with calpain inhibitor MDL-28170 along with continued presence of TGFβ1, decreased expression of αSMA at 48 h and 72 h post-induction of EMT (FIG. 1I, FIG. 1J), reacquired expression of the epithelial marker E-cadherin at 48 h and 72 h post-induction of EpMT (FIG. 1K) and reorganized their actin cytoskeleton from stress fibers to cortical actin indicative of a non-motile epithelial phenotype at 48 h and 72 h post-induction of EpMT (FIG. 1K).

It was further shown that the small molecule calpain inhibitor calpeptin suppresses TGFβ-induced EpMT in NMuMG cells as measured from αSMA (FIG. 2A and FIG. 2B). Calpeptin suppressed TGFβ-induced calpain activity (as measured by cleavage of Filamin A, a known calpain substrate) without significantly affecting TGFβ-induced phosphorylation of SMAD2 (FIG. 2A).

In addition, it was demonstrated that overexpression of the endogenous calpain inhibitor, calpastatin, also antagonizes TGFβ1-induced EpMT. Calpastatin is the most specific inhibitor of calpains (several orders above MDL-28170) and it exclusively targets CAPN1, CAPN2, and CAPN9 which are heterodimerized with a small regulatory subunit CAPNS1 or, as predicted, with CAPNS2 and referred to as dimeric calpains. In order to overexpress calpastatin, NMuMG epithelial cells were transfected with a bicistronic vector that codes for mouse calpastatin, followed by an Internal Ribosome Entry Sequence, and Green Fluorescent Protein such that exogenously expressed calpastatin levels are proportional to GFP. Calpastatin expressing cells had virtually no αSMA protein after treatment with TGFβ1 when compared to TGFβ1 treated control samples transfected with an empty vector (FIG. 3A and FIG. 3B). Overexpression of calpastatin suppressed TGFβ-induced calpain activity (as measured by cleavage of Filamin A, a known calpain substrate) without affecting TGFβ-induced phosphorylation of SMAD2. The effect of calpastatin expression on inhibition of TGFβ1-induced αSMA was more potent compared to MDL-28170 and also indicates that inhibition of these dimeric calpain isoforms is sufficient for potent inhibition of EpMT.

Example 2: Isoform-Specific Targeting of Calpains to Minimize Side Effects

There are many possible calpain isoforms that may be responsible for EpMT. However, it was found that the specific knockdown of CAPN9 or CAPNS2 by siRNA is sufficient for inhibiting TGFβ1-induced EpMT and thus indicates that it is CAPN9/CAPNS2 which are critical for this process (FIG. 4A and FIG. 4B). Additionally, it was shown that TGFβ1 induces expression of both these isoforms suggesting a pathological event is directly being opposed.

Targeted knockdown of ubiquitously expressed CAPN1, CAPN2, and CAPNS1 by siRNA failed to suppress TGFβ1-induced EpMT, showing that these common ubiquitously expressed isoforms do not play a significant role in TGFβ1-induced EpMT (FIG. 5A, FIG. 5B, and FIG. 5C). These findings suggest a drug that specifically targets CAPN9/CAPNS2 may have fewer side effects compared to a non-specific pan-calpain inhibitor. Additionally, CAPNS1 knockout mice have been shown to be embryonic lethal suggesting inhibition of this isoform may disrupt normal physiological function and have deleterious effects.

It has been shown that CAPN9 expression is limited to the stomach/gastrointestinal tract (as previously described) and CAPNS2 expression is limited to the skin (not previously described) by quantitative PCR, suggesting that side effects from inhibition of these isoforms would be limited to their respective organs of physiological expression (FIG. 6A and FIG. 6B). As was previously demonstrated, TGFβ induces de novo expression of CAPN9 and CAPNS2 (FIG. 4A and FIG. 4B) such that specific inhibition of these isoforms in vivo will primarily affect fibrotic tissues with high TGFβ signaling. Furthermore, homozygous CAPN9 knockout mice are viable and only differ from wild type mice by exhibiting increased sensitivity to ethanol-induced gastritis.

Example 3: Calpain Inhibition Prevents Formation of Myofibroblasts from Various Cell Types Myofibroblasts can derive from cell types other than those of epithelial origin, including endothelial cells and fibroblasts. Despite these various possible sources of TGFβ-induced myofibroblasts, it was found that calpain inhibition was able to block myofibroblast transition in a broad range of cell types. siRNA mediated knockdown of CAPNS2 inhibits TGFβ1-induced EnMT in PAVEC as measured from gene expression of αSMA, vimentin, E-cadherin, MMP2 and MMP9 (FIG. 7A) and inhibits morphological changes associated with EnMT, such as downregulation of E-cadherin/cell-cell adhesion and upregulation of vimentin. (FIG. 7B). Overexpression of calpastatin inhibits TGFβ1-induced EnMT in PAVEC as measured from gene expression of αSMA, vimentin, E-cadherin, MMP2 and MMP9 (FIG. 7C) and inhibits morphological changes associated with EnMT, such as downregulation of E-cadherin/cell-cell adhesion and upregulation of vimentin. (FIG. 7D).

Resident fibroblasts have also been described to undergo transformation in the presence of high TGFβ. Using Primary Normal Human Lung Fibroblasts (NHLF), it was shown that treatment with calpain inhibitor MDL-28170 (FIG. 8A and FIG. 8B) or siRNA mediated knockdown of CAPNS2 (FIG. 8C) can inhibit TGFβ1-induced FMT as measured by αSMA.

Example 4: In Vitro Inhibition of TRPM7 Inhibits TGFβ1-Induced αSMA Expression and Fibroblast-to-Myofibroblast Transition (FMT)

Treatment of NMuMG cells with the non-specific TRPM7 inhibitor 2-APB was able to inhibit TGFβ1-induced αSMA expression at high doses (FIG. 9A and FIG. 9B). The TRPM7 inhibitor suppressed TGFβ1-induced calpain activity (as measured by cleavage of Filamin A, a known calpain substrate) without significantly affecting TGFβ-induced phosphorylation of SMAD2, as measured by western blot (FIG. 9A and FIG. 9B). Commercially available TRPM7-specific inhibitor NS8593, which is reported to be more potent and less toxic (Chubanov et al., 2012), was also tested. It was found that in NMuMG cells, NS8593 was able to potently inhibit αSMA expression (FIG. 9C and FIG. 9D). NS8593 also suppressed TGFβ1-induced calpain activity without significantly affecting TGFβ-induced phosphorylation of SMAD2 at 72 h (FIG. 9C and FIG. 9D). NS8593 was also able to suppress the Fibroblast-to-Myofibroblast transition (FMT) as well using NHLF cells (FIG. 10A and FIG. 10B).

Example 5: In Vitro Inhibition of Calcineurin Inhibits TGFβ-Induced αSMA Expression Previous reports have shown that calcineurin (a phosphatase) can be cleaved by calpains in such a way as to remove the auto-inhibitory region of calcineurin, thereby causing its constitutive activation. It was reasoned that CAPN9/CAPNS2 activity could cause increased levels of the constitutively active form of calcineurin. It was found that treatment with TGFβ1 induced cleavage of calcineurin into the constitutively active form, by probing with an antibody that recognized the N-terminus of calcineurin (FIG. 11A and FIG. 11B). Knockdown of CAPN9 by siRNA was able to prevent this cleavage event, suggesting that the activity of CAPN9/CAPNS2 is responsible. To assess the relevance of calcineurin activity on EMT, a known calcineurin inhibitor, FK506 (tacrolimus), was used. FK506 was able to potently suppress TGFβ1-induced αSMA expression, although it was not able to completely suppress it (FIG. 12). Calcineurin inhibitors, such as FK506, are a drug of last resort, used for patients who are getting organ transplants. They are considered highly immunosuppressive and have the side effect of being nephrotoxic. In contrast, knockout of CAPN9 does not appear to have these negative effects.

In vivo inhibition of CAPNS2 and CAPN9 prevents bleomycin-induced lung fibrosis: To demonstrate the in vivo applicability of calpains as a target for fibrotic disease, a mouse model of intratracheal bleomycin-induced lung fibrosis was used for beneficial intervention with siRNA targeting CAPNS2. Bleomycin is an antibiotic known to cause lung fibrosis, which is associated with increased TGFβ signaling and EMT. Treatment with CAPNS2 siRNA was able to inhibit bleomycin-induced fibrosis as assessed by levels of collagen protein in the lung (FIG. 13A and FIG. 13B) and by histological changes (FIG. 13C). This shows that a small molecule inhibitor targeting CAPN9/CAPNS2 is a viable therapy for fibrotic diseases.

Lungs from wild-type mice treated with systemic bleomycin showed significant subplural fibrosis, as evidenced by Masson Trichrome Staining and histological grading by Ashcroft scores (FIG. 14A and FIG. 14B). Lungs from CAPN9 knockout mice (Hata et al., 2010) treated with systemic bleomycin showed little to no fibrosis and were indistinguishable from controls. Further, CAPN9 deficient mice treated with systemic bleomycin had significantly less lung fibrosis compared to WT mice treated with systemic bleomycin as assessed by picrosirius red staining that was histologically graded by Ashcroft scores (FIG. 14C) as well as significantly less infiltrating cells compared to wild-type mice treated with systemic bleomycin (FIG. 14D and FIG. 14E). Additionally, CAPN9 deficient mice treated with systemic bleomycin did not develop an accumulation and/or proliferation of αSMA-positive pro-fibrotic myofibroblasts, compared to wild-type mice (FIG. 14F; Tiled 10×, 10× and 20× magnifications). These mice also had significantly less lung collagen content, as measured by hydroxyproline levels, compared to wild-type mice treated with systemic bleomycin, (FIG. 14G). FIG. 14H shows wild-type mice treated with systemic bleomycin had induced, high levels of CAPN9 gene expression in the lung, as measured by quantitative PCR, compared to wild-type mice treated with saline and FIG. 14I shows CAPN9 deficient mice treated with systemic bleomycin had reduced dermal fibrosis, as determined by clinical skin stiffness assessment. FIG. 14J is a Kaplan-Meier plot of survival over time and shows CAPN9 deficient mice treated with bleomycin had improved survival compared to wild-type mice treated with bleomycin.

CAPN9 deficient mice were also shown to be resistant to carbon tetrachloride-induced liver fibrosis. FIG. 15A and FIG. 15B show that CAPN9 deficient mice treated with carbon tetrachloride had significantly less liver fibrosis compared to wild-type mice treated with bleomycin as assessed by masson trichrome stained liver sections and histological grading by Ashcroft scores. CAPN9 deficient mice treated with carbon tetrachloride also had significantly less lung fibrosis compared to wild-type mice treated with carbon tetrachloride as assessed by histological grading of picrosirius red sections from Ashcroft scores (FIG. 15C).

Conclusion:
Current therapies for organ fibrosis are palliative at best and not curative in nature, despite the great need, and thus rely on unsustainable high-risk organ transplants. Perhaps equal or greater in need are patients afflicted with potentially metastatic cancers. Although numerous attempts have been made to intensely study TGFβ inhibitors as a therapy, the side effects and inherent limitations have overshadowed much of the potential benefits. The presently disclosed subject matter provides the targeting of CAPN9/CAPNS2 as a strategy towards the treatment of—diseases associated with myofibroblast differentiation and addresses a major need for severely afflicted patients with currently limited options.

Example 6: Biochemical Assays for Calpain 9 Inhibition

This Example describes an assay to identify calpain 9 inhibitors.

Human recombinant mini-CAPN9 was expressed in *E. coli* and purified as described in Davis, T. L., et al. (2007) *J Mol Biol* 366(1): 216-229.

All enzyme reactions are run at ambient temperature (~25° C.) in black 384 well assay plates. Inhibitors solutions in DMSO are typically semi-log serially diluted prior to further dilution in assay buffer (Tris-HCl 20 mM, KCl 100 mM, BSA 0.1%, 1 mM DTT). Calpain enzyme stocks are diluted in assay buffer without Ca (II) just prior to use (1 µM) and incubated with serially diluted test compounds at 2× concentrations in the assay plate for 10 min.

After the compound preincubation, the FLIPR liquid handler is used to initiate the reaction by adding a 2× mix of substrate (1 µM Calpain FRET peptide substrate (5-FAM/QXL 520) Anaspec (Catalog# AS-72149)) and Ca (II) (10 mM). Reactions are measured using a FLIPR Tetra reader (Molecular Devices Inc).

Slopes (reaction rates) are calculated within the 0-2 min interval using the ScreenWorks software (Molecular Devices Inc). Slopes are plotted versus test compound concentration to obtain dose-response curves. IC50 values are obtained using 4 parameter logistic fitting. Results as well as compounds tested are shown in Table 1.

TABLE 1

| Molecule | Name | CAPN9 (µM) |
|---|---|---|
| 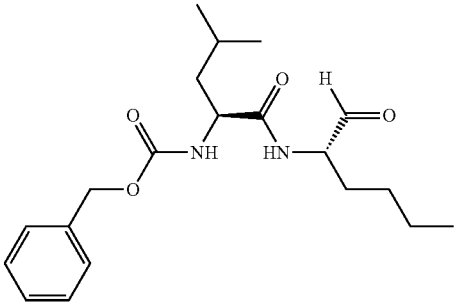 [SMILES: CCCC[C@@H](C=O)NC(=O)[C@H](CC(C)C)NC(=O)OCc1ccccc1] | Calpeptin | 2.84 |
| 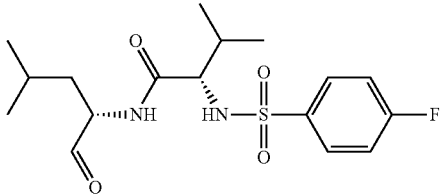 [SMILES: CC(C)C[C@@H](C=O)NC(=O)[C@@H](NS(=O)(=O)c1ccc(F)cc1)C(C)C] | Calpain Inhibitor IV SJA-6017 | 2.23 |
| 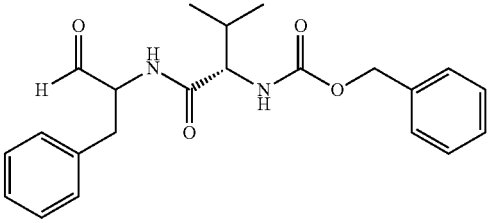 [SMILES: CC(C)[C@H](NC(=O)OCc1ccccc1)C(=O)NC(C=O)Cc1ccccc1] | MDL-28170 | 1.61 |
| 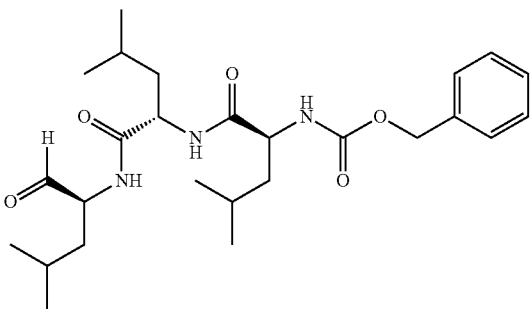 [SMILES: CC(C)C[C@@H](C=O)NC(=O)[C@H](CC(C)C)NC(=O)[C@H](CC(C)C)NC(=O)OCc1ccccc1] | MG-132 | 9.88 |

TABLE 1-continued
| Molecule | Name | CAPN9 (μM) |
|---|---|---|
| 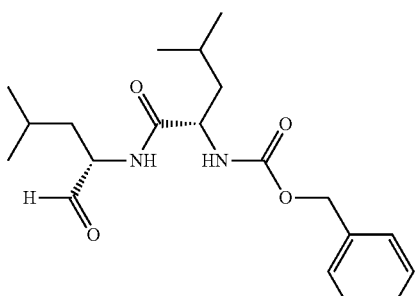 | Z-Leu-Leu-CHO | 2.35 |
| 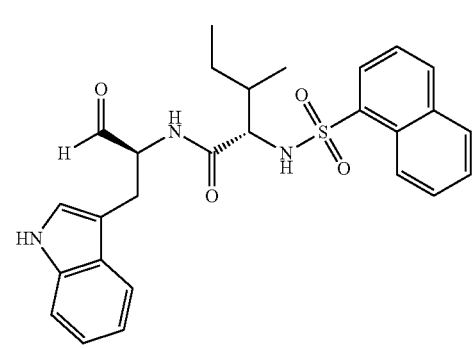 [SMILES: CCC(C)[C@H](NS(=O)(=O)c1cccc2ccccc12)C(=O)N[C@H](C=O)Cc1c[nH]c2ccccc12] | NapSul-Ile-Trp-CHO | 6.25 |
| 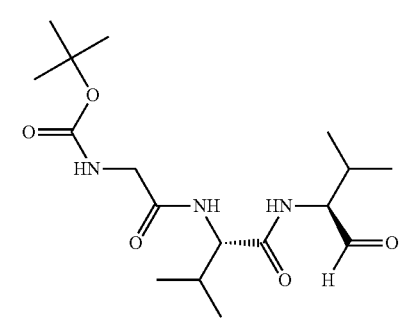 [SMILES: CC(C)[C@H](NC(=O)CNC(=O)OC(C)(C)C)C(=O)N[C@H](C=O)C(C)C] | Boc-Gly-Val-Val-CHO | 6.68 |
| 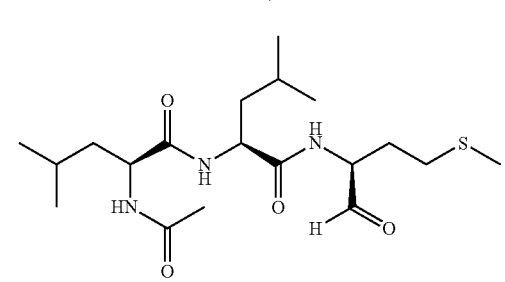 | Calpain Inhibitor II (ALLM) | 3.32 |
| 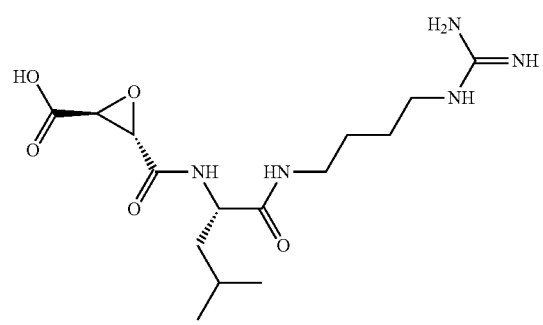 [SMILES: CC(C)C[C@H](NC(=O)[C@H]1O[C@@H]1C(=O)O)C(=O)NCCCCNC(=N)N] | E-64 | 11.58 |

TABLE 1-continued

| Molecule | Name | CAPN9 (μM) |
|---|---|---|
| | E-64-C | 35.83 |
| | Z-VAD-FMK | 100.00 |
| | Z-FA-FMK | 100.00 |
| | E-64-d Aloxistatin | 100.00 |
| | 5-Nitroisatin | 42.29 |
| | Leupeptin Hemisulfate | 9.24 |

Example 7: Identification of Subjects Who would Benefit from Treatment with a CAPN9 and/or CAPNS2 Inhibitor In this Example, differential expression of CAPN9 and/or CAPNS2 protein is determined in the cells derived from core biopsy samples obtained from subjects diagnosed with breast cancer. Samples are obtained from subjects prior to treatment with any anticancer therapy. Protein is isolated from the samples and expression of CAPN9 and/or CAPNS2 protein is assessed via Western blot. Subjects whose samples are positive for CAPN9 and/or CAPNS2 protein expression are identified as benefiting from treatment with a CAPN9 and/or CAPNS2 inhibitor.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Branton M. H., TGF-β and fibrosis. *Microbes Infect.* 1(15), 1349-1365 (1999).

Chubanov et al. "Natural and synthetic modulators of SK (K(ca)2) potassium channels inhibit magnesium-dependent activity of the kinase-coupled cation channel TRPM7." *Br J Pharmacol* 166(4): 1357-1376 (2012).

Friedman S. L., Therapy for fibrotic diseases: nearing the starting line. *Sci. Transl. Med.* 5, 167 (2013).

Gooch et al., "Involvement of calcineurin in transforming growth factor-beta-mediated regulation of extracellular matrix accumulation. *J. Biol Chem.* 279(15), 15561-70 (2004).

Hata S., Calpain 8/nCL-2 and calpain 9/nCL-4 constitute an active protease complex, G-calpain, involved in gastric mucosal defense. *PLoS Genet.* 6(7) (2010).

Lamouille S, Molecular mechanisms of epithelial-mesenchymal transition. *Nat. Rev. Mol. Cell. Bio.* 15, 178-196 (2014).

Leask A. TGF-β Signaling and the fibrotic response. *FASEB J.* 18(7), 816-827 (2004).

Lee et al. (2014) "Bleomycin delivery by osmotic minipump: similarity to human scleroderma interstitial lung disease." *Am J Physiol Lung Cell Mol Physiol* 306(8): L736-748.

Mani S., The epithelia-mesenchymal transition generates cells with properties of stem cells. *Cell.* 122(4), 704-715 (2008).

Miyazono K., Transforming growth factor-β signaling in epithelial-mesenchymal transition and progression of cancer. *Proc. Jpn. Acad. Ser. B. Phys. Bio. Sci.* 85(8), 314-23 (2009).

Padua D., Roles of TGF-β in metastasis. *Cell Research.* 19, 89-102 (2009).

Peng R., Bleomycin induces molecular changes directly relevant to ideopathic pulmonary fibrosis: A model for "active" disease. *PLOS One.* 8(4) e59348 (2013).

Savary K., Role of TGF-β signaling in EMT, cancer progression and metastasis. *Drug Discovery Today: Disease Models.* 8(2-3), 121-126 (2011).

Schad E., A novel human small subunit of calpains. *Biochem. J.* 362, 383-8 (2002).

Singh A., EMT, cancer stem cells and drug resistance: an emerging axis of evil in the war on cancer. *Oncogene.* 29(34), 4741-4751 (2010).

Suzuki K. Structure, activity, and biology of calpain. *Diabetes.* 53 Suppl 1:S12-8 (2004).

Wu Z., Detection of epithelial to mesenchymal transition in airways of a bleomycin induced pulmonary fibrosis model derived from an α-smooth muscle actin-cre transgenic mouse. *Respir. Res.* 8(1) (2007).

Wynn T. A., Cellular and molecular mechanisms of fibrosis. *J. Pathol.* 214, 199-210 (2008).

Zimmerman U. J., The calpain small subunit gene is essential: its inactivation results in embryonic lethality. *IUBMB Life.* 50(1), 63-8 (2000).

We claim:

1. A method of treating a fibrotic disease associated with myofibroblast differentiation in a subject in need thereof comprising:
   assaying for the presence of calpain-9 (CAPN9) in a biological sample obtained from the subject;
   identifying the subject having an elevated level of CAPN9 relative to a healthy subject; and
   administering to the identified subject a therapeutically effective amount of at least one small molecule chemical compound that inhibits CAPN9,
   wherein the fibrotic disease is liver fibrosis or lung fibrosis.

2. The method of claim 1, wherein the subject is a human.

3. The method of claim 2, wherein the subject is suffering from liver fibrosis.

4. The method of claim 2, wherein the subject is suffering from lung fibrosis.

5. The method of claim 2, wherein the subject is suffering from lung fibrosis resulting from an infection.

6. A method of treating liver fibrosis in a human subject in need thereof comprising:
   assaying for the presence of calpain-9 (CAPN9) in a biological sample obtained from the human subject;
   identifying the human subject having an elevated level of CAPN9 relative to a healthy human subject; and
   administering to the identified human subject a therapeutically effective amount of at least one small molecule chemical compound that inhibits CAPN9.

7. A method of treating lung fibrosis in a human subject in need thereof comprising:
   assaying for the presence of calpain-9 (CAPN9) in a biological sample obtained from the human subject;
   identifying the human subject having an elevated level of CAPN9 relative to a healthy human subject; and
   administering to the identified human subject a therapeutically effective amount of at least one small molecule chemical compound that inhibits CAPN9.

8. The method of claim 7, wherein the subject is suffering from lung fibrosis resulting from an infection.

* * * * *